United States Patent [19]
Tobin et al.

[11] Patent Number: 5,998,366
[45] Date of Patent: Dec. 7, 1999

[54] METHOD FOR AMELIORATING GLUTAMIC ACID DECARBOXYLASE ASSOCIATED AUTOIMMUNE DISORDERS

[75] Inventors: Allan J. Tobin, Los Angeles; Mark G. Erlander, Tarzana; Daniel L. Kaufman, Santa Monica, all of Calif.

[73] Assignee: The Regents of the University of California, Oakland, Calif.

[21] Appl. No.: 08/827,618

[22] Filed: Apr. 9, 1997

Related U.S. Application Data

[60] Division of application No. 08/485,725, Jun. 7, 1995, which is a continuation-in-part of application No. 07/716,909, Jun. 18, 1991, abandoned, which is a continuation-in-part of application No. 07/586,536, Sep. 21, 1990, abandoned.

[51] Int. Cl.[6] .............................. C12N 9/00; C07K 14/00
[52] U.S. Cl. .............................. 514/12; 514/14; 514/15; 514/16; 514/17; 530/330; 530/329; 530/328; 530/327; 435/183; 435/232; 424/94.5; 424/94.1
[58] Field of Search ........................... 514/2, 12, 14, 514/15, 16, 17; 435/232, 183; 530/330, 329, 328, 327; 424/94.5, 94.1

[56] References Cited

U.S. PATENT DOCUMENTS

| | | | |
|---|---|---|---|
| 4,487,830 | 12/1984 | Coates et al. | 435/7.23 |
| 4,624,926 | 11/1986 | Inouye et al. | 435/252.33 |
| 4,751,181 | 6/1988 | Keene | 435/69.3 |
| 5,200,318 | 4/1993 | Rabin | 435/7.21 |
| 5,512,447 | 4/1996 | Baekkeskov | 435/7.4 |
| 5,645,998 | 7/1997 | Atkinson et al. | 435/7.4 |

FOREIGN PATENT DOCUMENTS

| | | |
|---|---|---|
| 03 831 29 | 2/1990 | European Pat. Off. |
| 90/07117 | 6/1990 | WIPO |
| 90/10449 | 9/1990 | WIPO |
| 92/06105 | 4/1992 | WIPO |
| 92/14485 | 9/1992 | WIPO |
| 92/20811 | 9/1992 | WIPO |

OTHER PUBLICATIONS

Baekkeskov et al., "Revelation of Specificity of 64K Autoantibodies in IDDM Serums by High–Resolution 2–D Gel Electrophoresis," *Diabetes*, 38:1133–1141 (1989).
Wraith et al., "Antigen Recognition in Autoimmune Encephalomyelitis and the Potential for Peptide–Mediated Immunotherapy," *Cell*, 59:247–255 (1989).
Gerling et al., "Effect of Coxsackievirus B4 Infection in Mice on Expression of 64,000–M Autoantigen and Glucose Sensitivity of Islets Before Development of . . . ," *Diabetes*, 37:1419–1425 (1988).
Dryberg, "Molecular Mimicry and Diabetes," *Current Topics in Microbiology & Immun.*, 145:118–125 (1989).
Julien et al., "Rat Brain Glutamic Acid Decarboxylase Sequence Deduced from a Cloned cDNA," *J. Of Neurochemistry*, 54:703–705 (1990).
Schwimmbeck et al., "Molecular Mimicry and Myasthenia Gravis," *J. Clin. Invest.* 84:1174–1180 (1989).
Todd et al., "A Molecular Basis for Genetic Susceptibility to Insulin–Dependent Diabetes Mellitus," *TIG*, 4:129–134 (1988).
Chang and Gottlieb, "Characterization of the Proteins Purified with Monoclonal Antibodies to Glutamic Acid Decarboxylase," *J. Of Neuroscience*, 6:2123–2130 (1988).
Legay et al., "Evidence for Two Distinct Forms of Native Glutamic Acid Decarboxylase in Rat Brain Soluble Extract: An Immunoblotting Study," *J. Of Neurochemistry*, 48:1022–1026 (1987).
Julien et al., "Molecular Cloning, Expression and in situ Hybridization of Rat Brain Glutamic Acid Decarboxylase Messenger RNA," *Neuroscience Letters*, 73:173–180 (1987).
Baekkeskov et al., "Identification of the 64K Autoantigen in Insulin–Dependent Diabetes as the GABA–Synthesizing Enzyme Glumatic Acid Decarboxylase," *Nature*, 347:151–156 (1990).
Michelesen et al., "Cloning, Characterization, and Autoimmune Recognition of Rat Islet Glutamci Acid Decarboxylase in Insulin–Dependent Diabetes Mellitus," *PNAS USA*, 88:8754–8758 (1991).
Solimena et al., "Autoantibodies to GABA–$^{ergic}$ Neurons and Pancreatic Beta Cells in Stiffman Syndrom," *N. Engl. J. Med.*, 322:1555–1560 (1990).
Kobayashi et al., "Glutamic Acid Decarboxylase cDNA: Nucleotide Sequence Encoding an Enzymatically Active Fusion Protein," *J. Of Neuroscience*, 9:2768–2772 (1987).
Atkinson and Maclaren, "What Causes Diabetes?" *Sci. Amer.*, 62–71 (1990).
Baekkeskov et al., "Autoantibodies in Newly Diagnosed Diabetic Children Immunoprecipitate Human Pancreatic Islet Cell Proteins," *Nature*, 298:167–169 (1982).
Baekkeskov et al., "Antibodies to a 64,000 MΓ Human Inslet Cell Antigen Precede the Clinical Onset of Insulin–Dependent Diabetes," *J. Clin. Invest.*, 79;926–934 (1987).

(List continued on next page.)

*Primary Examiner*—Karen Cochrane Carlson
*Attorney, Agent, or Firm*—Richard F. Trecartin; Flehr Hohbach Test Albritton & Herbert LLP

[57] ABSTRACT

Isolated polypeptides useful in ameliorating GAD–associated autoimmune disease as well as diagnostic and therapeutic methods of using the peptides are disclosed.

36 Claims, 15 Drawing Sheets

OTHER PUBLICATIONS

Christie et al., "Cellular and Subcelluar Localization of an MΓ 64,000 Protein Autoantigen in Insulin–Dependent Diabetes," *J. Biol. Chem.*, 265:376–381 (1990).

Atkinson et al., "64,000 MΓ Autoantibodies as Predictors of Insulin–Dependent Diabetes," *The Lancet*, 335:1357–1360 (1990).

Ziegler et al., "Predicting Type 1 Diabetes," *Diabetes Care*, 13:762–775 (1990).

Kaufman et al., "Brain Glutamate Decaroxylase Cloned in λgt–11: Fusion Protein Produces T–Aminobutyric Acid," *Science*, 232:1138–1140 (1986).

Wyborski et al., "Characterization of a cDNA Coding for Rat Glutamic Acid Decarboxylase," *Molecular Brain Research*, 8:193–198 (1990).

Katarova et al., "Molecular Identification of the 62 kd Form of Glutamic Acid Decarboxylase from the Mouse," *European J. Of Neuroscience*, 2:190–202 (1990).

Persson et al., "Expression of the Neurotransmitter–Synthesizing Enzyme Glutamic Acid Decarboxylase in Male Germ Cells," *Molecular and Cellular Biology*, 10:4701–4711 (1990).

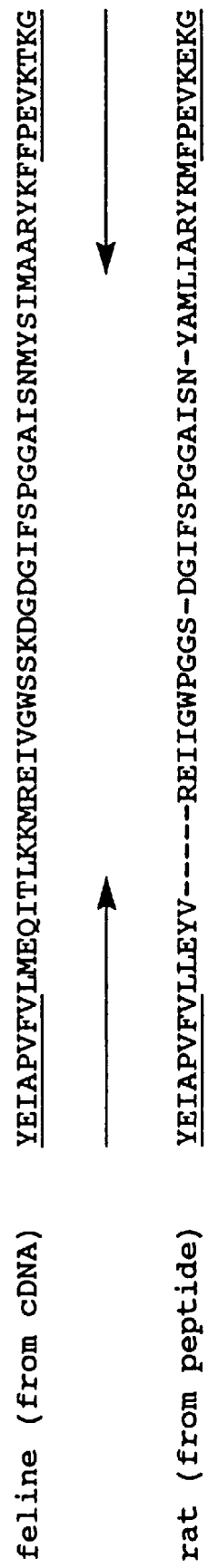
FIG._1

```
GGGCGTGCGGGGTCGAGCCGAAGCAGCTTGCCCGCAGCCACTCGGAGGCGACCAGCCA
                                          10                                    30                                      50
                   M  A  S  P  G  S  G  F  W  S  F  G  S  E  D  G
GACTAGCAGAACCATGGCATCTCCGGGCTCTGGCTTTTGGTCCTTCGGATCTGAAGATG
          70                                     90                                    110
 S  G  D  P  E  N  P  G  T  A  R  A  W  C  Q  V  A  Q  K  F
GCTCTGGGGATCCTGAGAACCCGGGAACAGCAGAGAGCCTGGTGCCAGGTGGCCCAAAAGT
                       130                                    150                                    170
 T  G  G  I  G  N  K  L  C  A  L  L  Y  G  D  S  E  K  P  A
TCACGGGCGGGCATCGGAAACAAGCTATGCGCTCTGCTCTACGGAGACTCTGAGAAGCCAG
         190                                    210                                   230
 E  S  G  G  S  V  T  S  R  A  T  R  K  V  A  C  T  C  D
CAGAGAGCGGGGGGAGCGTGACCTCGCGGGCCACTCGGAAGGTCGCTGCACTTGTG
                       250                                    270                                    290
 Q  K  P  C  S  C  P  K  G  D  V  N  Y  A  L  L  H  A  T  D
ACCAAAAACCCCTGCAGCTGCCCCAAGGAGATGTCAATTATGCACTTCTCCACGCAACAG
         310                                    330                                   350
 L  L  P  A  C  E  G  E  R  P  T  L  A  F  L  Q  D  V  M  N
ACCTGCTGCCAGCCTGTGAAGGAGAAAGGCCCACTCTGCATTTCTGCAAGATGTAATGA
                       370                                    390                                    410
 I  L  Q  Y  V  V  K  S  F  D  R  S  T  K  V  I  D  F  H
ACATTTTGCTTCAGTACGTGGTGAAAGTTTTGATAGATCAACTAAAGTGATTGATTTCC
         430                                    450                                    470
 Y  P  N  E  L  L  Q  E  Y  N  W  E  L  A  D  Q  P  Q  N  L
ATTACCCCAATGAGCTTCTTCAAGAGTATAATTGGGAATTGGCAGACCAACCGCAAAATC
                       490                                    510                                    530
 E  E  I  L  T  H  C  Q  T  T  L  K  Y  A  I  K  T  G  H  P
TGGAGGAAATTTTGACGCACTGCCAAACTACTCTAAAATATGCGATTAAAACAGGGCATC
         550                                    570                                   590
 R  Y  F  N  Q  L  S  T  G  L  D  M  V  G  L  A  D  W  L
CCCGATATTTTAATCAGCTGTCTACCGGATTGGATATGGTTGGATTAGCAGATTGGT
                       610                                    630                                    650
 T  S  T  A  N  T  N  M  F  T  Y  E  I  A  P  V  F  V  L  L
TGACATCAACAGCAAACACGAACATGTTTACCTATGAGATCGCCCCTGTATTTGTACTAC
```

FIG._2A

```
     E   Y   V   T   L   K   K   M   R   E   I   I   G   W   P   G   G   S   G   D
TGGAATATGTGACACTAAAGAAGATGAGGGAAATCATTGGCCAGGAGGCTCTGGCG
      670                690                710
                                                770
     G   I   F   S   P   G   G   A   I   S   N   M   Y   A   M   L   I   A   R   Y
ATGGAATCTTTTCCTGGTGCCATCTCCAACATGTACGCCATGCTCATTGCCCGCT
      730                750
                                                830
     K   M   F   P   E   V   K   E   K   G   M   A   A   V   P   R   L   I   A   F
ATAAGATGTTCCAGAAGTCAAGGAAAAGGGGATGGCGGCTGTGCCCAGGCTCATCGCAT
      790                810
                                                890
     T   S   E   H   S   H   F   S   L   K   K   G   A   A   A   L   G   I   G   T
TCACGTCAGAGCATAGTCACTTTTCTCAAGAAGGGAGCTGCAGCTTGGGGATCGGAA
      850                870
                                                950
     D   S   V   I   L   I   K   C   D   E   R   G   K   M   I   P   S   D   L   E
CAGACAGCGTGATTCTGATTAAATGTGATGAGAGGGGAAAATGATCCCATCTGACCTTG
      910                930
                                                1010
     R   R   I   L   E   V   K   Q   K   G   F   V   P   F   L   V   S   A   T   A
AAAGAAGAATCCTTGAAGTCAAACAGAAAGGATTTGTCCTTTCCTGGTGAGTGCCACAG
      970                990
                                                1070
     G   T   T   V   Y   G   A   F   D   P   L   L   A   V   A   D   I   C   K   K
CTGGAACCACTGTGTACGGGGCTTTTGATCCTCTCTTGGCTGTAGCTGACATCTGCAAAA
      1030                1050
                                                1130
     Y   K   I   W   M   H   V   D   A   W   G   G   L   L   M   S   R   K
AATATAAGATCTGGATGCATGTGGATGCTGGGGGTCTGCTGATGTCTCGA
      1090                1110
                                                1190
     H   K   W   K   L   N   G   V   E   R   A   N   S   V   T   W   N   P   H   K
AACACAAGTGGAAGCTGAACGGGGTGGAGAGGGCCAACTCTGTGACATGGAATCCCACA
      1150                1170
                                                1250
     M   M   G   V   P   L   Q   C   S   A   L   L   V   R   E   E   G   L   M   Q
AGATGATGGGTGTCCCCTTGCAATGTTCGGCTCTCCTGGTCAGAGAGGAGGACTGATGC
      1210                1230
```

FIG._2B

```
                    1270               1290                1310
      S   C   N   Q   M   H   A   S   Y   L   F   Q   Q   D   K   H   Y   D   L   S
      AGAGCTGCAACCAGATGCATGCTTCCTACCTCTTTCAGCAAGATAAGCACTATGACCTGT
                   1330                1350                 1370
      Y   D   T   G   D   K   A   L   Q   C   G   R   H   V   D   V   F   K   L   W
      CCTATGACACGGGAGACAAGGCCCTGCAGTGTGGACGCCACGTGGATGTCTTTAAATTAT
                   1390                1410                 1430
      L   M   W   R   A   K   G   T   G   F   E   A   H   I   D   K   C   L   E
      GGCTCATGTGGAGAGCAAAGGGGACTACTGGATTTGAAGCTCACATTGATAAGTGTTTGG
                   1450                1470                 1490
      L   A   E   Y   L   Y   N   I   I   K   N   R   E   G   Y   E   M   V   F   D
      AGCTGGCAGAGTATTTATACAATATCATTAAAAACCGAGAAGGATATGAAATGGTGTTCG
                   1510                1530                 1550
      G   K   P   Q   H   T   N   V   C   F   W   F   V   P   P   S   L   R   V   L
      ATGGGAAGCCTCAGCACACAAATGTCTGCTTCTGGTTTGTACCTCCTAGTTTGCGAGTTC
                   1570                1590                 1610
      E   D   N   E   E   R   M   S   R   L   S   K   V   A   P   V   I   K   A   R
      TGGAAGACAATGAAGAGAGAATGAGCCGCCTCTCAAAGGTGGCCCAGTGATTAAAGCCA
                   1630                1650                 1670
      M   M   E   Y   G   T   T   M   V   S   Y   Q   P   L   G   D   K   V   N   F
      GAATGATGGAGTATGGGACCACAATGGTCAGCTACCAACCCTTAGGAGATAAGGTCAACT
                   1690                1710                 1730
      F   R   M   V   I   S   N   P   A   T   H   Q   D   I   D   F   L   I   E
      TCTTCCGCATGGTCATCTCAAACCCTGCAGCAACTCACCAAGACATTGACTTCCTCATTG
                   1750                1770                 1790
      E   I   E   R   L   G   Q   D   L   *
      AAGAAATCGAACGCCTGGGACAAGATTTGTAATCACTTGCTCACCAAACTTTCAGTTCT
                   1810                1830                 1850
      CTAGGTAGACAGCTAAGTTGTCACAACTGTAAATGTATTTGTAGTTTGTTCCAGAGT
                   1870                1890                 1910
      AATTCTATTCTATATCGTGGTGTCACAGTAGAGTCCAGTTTAAAA
                   1930                1950
```

FIG._2C

```
                                                        M   A   S
AGCTCGCCCCGCAGCTCGCACTCGCAGGCGACCTGCTCCAGTCTCCAAAGCCGATGGCATC
                                    30                    50
  P   G   S   G   F   W   S   F   G   S   E   D   G   S   G   D   S   E   N   P
TCCGGGCTCTGGCTCTTTGGTCTTTCGGGTCTTGGGTCGAAGATGGCTCTGGGGATTCCGAGAATCC
        70                    90                    110
  G   T   A   R   A   W   C   Q   V   A   Q   K   F   T   G   G   I   G   N   K
CGGCACAGAGCGCGGCAGAGCCTGGTGTGCCAAGTGGCTCAGAAGTTCACGGCGGCATCGGAAACAA
            130                   150                   170
  L   C   A   L   L   Y   G   D   A   E   K   P   A   E   S   G   G   S   Q   P
ACTGTGCGCCCTGCTCTACGGAGACGCCGAGAAGCCGGAGAGCGGGGAGCCAACC
            190                   210                   230
  P   R   A   A   R   K   A   A   C   D   Q   K   P   C   S   C   S
CCCGCGGGCCGCCGCAAGGCCGCCTGCGACCAGAAGCCCTGCAGCTGCTC
            250                   270                   290
  K   V   D   V   N   Y   A   F   L   H   A   T   D   L   L   P   A   C   D   G
CAAAGTGGATGTCAACTACGCGTTTCTCCATGCAACAGACCTGCTGCCGGCGTGTGATGG
            310                   330                   350
  E   R   P   T   L   A   F   L   Q   D   V   M   N   I   L   L   Q   Y   V   V
AGAAAGGCCCACTTTGGCGTTTCTGCAAGATGTTATGAACATTTTACTTCAGTATGTGGT
            370                   390                   410
  K   S   F   D   R   S   T   K   V   I   D   F   H   Y   P   N   E   L   L   Q
GAAAAGTTTCGATAGATCAACCAAAGTGATTGATTTCCATTATCCTAATGAGCTTCTCCA
            430                   450                   470
  E   Y   N   W   E   L   A   D   Q   P   Q   N   L   E   E   I   L   M   H   C
AGAATATAATTGGGAATTGGCAGACCAACCACAAAATTTGGAGGAAATTTTGATGCATTG
            490                   510                   530
  Q   T   T   L   K   Y   A   I   K   T   G   H   P   R   Y   F   N   Q   L   S
CCAAACAACTCTAAAATATGCAATTAAAACAGGGCATCCTAGATACTTCAATCAACTTTC
            550                   570                   590
  T   G   L   D   M   V   G   L   A   D   W   L   T   S   T   A   N   T   N
TACTGGTTTGGATATGGTTGGATTAGCAGACTGGCTGACATCAACAGCAAATACTAA
```

FIG._3A

```
                                610                            630                                    650
          M  F  T  Y  E  I  A  P  V  F  V  L  L  E  Y  V  T  L  K  K
         CATGTTCACCTATGAAATTGCTCCAGTGTTTGTGCTTTTGGAATATGTCACACTAAAGAA
                              670                            690                                710
          M  R  E  I  I  G  W  P  G  G  S  G  D  G  I  F  S  P  G  G
         AATGAGAGAAATCATTGGCTGGCCAGGGGGCTCTGGCGATGGGATATTTTCTCCGGTGG
                             730                            750                                770
          A  I  S  N  M  Y  A  M  M  I  A  R  F  K  M  F  P  E  V  K
         CGCCATATCTAACATGTATGCCATGATGATCGCACGCTTTAAGATGTTCCAGAAGTCAA
                            790                           810                              830
          E  K  G  M  A  A  L  P  R  L  I  A  F  T  S  E  H  S  H  F
         GGAGAAAGGAATGGCTGCTCTGCCTCGGCTCATTGCCTTCACGTCTGAACATAGTCATTT
                           850                           870                              890
          S  L  K  K  G  A  A  A  L  G  I  G  T  D  S  V  L  L  I  K
         TTCTCTCAAGAAGGGAGCTGCAGCCTTAGGGATTGGAACAGACAGCGTGATTCTGATTAA
                          910                           930                               950
          C  D  E  R  G  K  M  I  P  S  D  L  E  R  R  I  L  E  A  K
         ATGTGATGAGAGAGGGAAAATGATTCCATCTGATCTTGAAAGAAGGATTCTTGAAGCCAA
                         970                           990                               1010
          Q  K  G  F  V  P  F  L  V  S  A  T  A  G  T  T  V  Y  G  A
         ACAGAAAGGGTTTGTTCCTTTCCTCGTGAGTGCCACAGCTGGAACCACCGTGTACGGAGC
                       1030                         1050                             1070
          F  D  P  L  L  A  V  A  D  I  C  K  K  Y  K  I  W  M  H  V
         ATTTGACCCCCTCTTAGCTGTGCTGACATTGCAAAAGTATAAGATCTGGATGCATGT
                      1090                          1110                           1130
          D  A  W  G  G  G  L  L  M  S  R  K  H  K  W  K  L  S  G
         GGATGCAGCTTGGGGTGGGGGATTACTGATGTCCCGAAAACAAGTGGAAACTGAGTGG
                     1150                          1170                            1190
          V  E  R  A  N  S  V  T  W  N  P  H  K  M  M  G  V  P  L  Q
         CGTGGAGAGGGCCAACTCTGTGACGTGGAATCCACACAAGATGATGGGAGTCCCTTTGCA
```

FIG.─3B

```
                  1210                    1230                    1250
             C  S  A  L  L  V  R  E  E  G  L  M  Q  N  C  N  Q  M  H  A
             GTGCTCTGCTCCTCCTGGTTAGAGAAGAGGGATTGATGCAGAATTGCAACCAAATGCATGC
                       1270                    1290                    1310
             S  Y  L  F  Q  Q  D  K  H  Y  D  L  S  Y  D  T  G  D  K  A
             CTCCTACCTCTTTCAGCAAGATAAACATTATGACCTGTCCTATGACACTGGAGACAAGGC
                       1330                    1350                    1370
             L  Q  C  G  R  H  V  D  V  F  K  L  W  L  M  W  R  A  K  G
             CTTACAGTGCGGACGCCACGTTGATGTTTTTAAACTATGGCTGATGTGGAGGGCAAAGGG
                       1390                    1410                    1430
             T  T  G  F  F  E  A  H  V  D  K  C  L  E  L  A  E  Y  L  Y  N
             GACTACCGGGTTTGAAGCGCATGTTGATAAATGTTTGGAGTTGGCAGAGTATTATACAA
                       1450                    1470                    1490
             I  I  K  N  R  E  G  Y  E  M  V  F  D  G  K  P  Q  H  T  N
             CATCATAAAAAACCGAGAAGGATATGAGATGGTGTTTGATGGGAAGCCTCAGCACACAAA
```

FIG._3C

```
           V  C  F  W  Y  I  P  P  S  L  R  T  L  E  D  N  E  E  R  M
          TGTCTGCTTCTGGTACATTCCTCCAAGCTTGCGTACTCTGGAAGACAATGAAGAGAGAAT
             1570              1590              1610
           S  R  L  S  K  V  A  P  V  I  K  A  R  M  M  E  Y  G  T  T
          GAGTCGCCTCTCGAAGGTGGCTCCAGTGGCTTAAAGCCAGAATGATGGAGTATGGAACCAC
             1630              1650              1670
           M  V  S  Y  Q  P  L  G  D  K  V  N  F  F  R  M  V  I  S  N
          AATGGTCAGCTACCAACCCTTGGGAGACAAGGTCAATTTCTTCCGCATGGTCATCTCAAA
             1690              1710              1730
           P  A  A  T  H  Q  D  I  D  F  L  I  E  E  I  E  R  L  G  Q
          CCCAGCGGCAACTCACCAAGACATTGACTTCCTGATTGAAGAAATAGAACGCCTTGGACA
             1750              1770              1790
           D  L  *
          AGATTTATATAACCTTGCTCACCAGCTGTTCCACTTCTCTAGGTAGACAATTAAGTTG
             1810              1830              1850
          TCACAAACTGTGTGAATGTATTTGTAGTTTGTTGTTCCAAGTAAATCTATTTCTATATTGTG
             1870              1890              1910
          GTGTCAAAGTAGAGTTTAAAATTAAACAAAAAAGACATTGCTCCTTTAAAGTCCTTT
             1930              1950              1970
          CTTAAGTTTAGAATACCTCTCTAAGAATTCGTGACAAAGGCTATGTTCTAATCAATAAG
             1990              2010              2030
          GAAAGCTTAAAATTGTTATAAATACTTCCCTTACTTTTAATATAGTGTGCAAAGCAAAC
             2050              2070              2090
```

FIG._3D

```
GAP WEIGHT: 3.000   LENGTH WEIGHT: 0.100   QUALITY: 856.2   RATIO: 1.464
PERCENT SIMILARITY: 97.436   4817, PEP HGT2.PEP
AVERAGE MATCH: 0.540   AVERAGE MISMATCH: -0.396   LENGTH: 585   GAPS: 0
PERCENT IDENTITY: 96.068   AUGUST 22, 1990 08:20 **

1  MASPGSGFWSFGSEDGSGDPENPGTARAWCQVAQKFTGGIGNKLCALLYG   50
     |||||||||||||||||||| ||||||||||||||||||||||||||||||
  1  MASPGSGFWSFGSEDGSGDSENPGTARAWCQVAQKFTGGIGNKLCALLYG   50

51  DSEKPAESGGSVTSRAATRKVACTCDQKPCSCPKGDVNYALLHATDLLPA  100
     | :|||||||| :|| |||:| | ||||||:|  |||||| |||||||||
 51  DAEKPAESGGSQPPRAAARKAACACDQKPCSCSKVDVNYAFLHATDLLPA  100

101  CEGERPTLAFLQDVMNILLQYVVKSFDRSTKVIDFHYPNELLQEYNWELA  150
     | ||||||||||||||||||||||||||||||||||||||||||||||||
101  CDGERPTLAFLQDVMNILLQYVVKSFDRSTKVIDFHYPNELLQEYNWELA  150

151  DQPQNLEEILTHCQTTLKYAIKTGHPRYFNQLSTGLDMVGLAADWLTSTA  200
     |||||||| :|||||||||||||||||||||||||||||||||||||||
151  DQPQNLEEILMHCQTTLKYAIKTGHPRYFNQLSTGLDMVGLAADWLTSTA  200

201  NTNMFTYEIAPVFVLLEYVTLKKMREIIGWPGGSGDGIFSPGGAISNMYA  250
     |||||||||||||||||||||||||||||||||||||||||||||||||
201  NTNMFTYEIAPVFVLLEYVTLKKMREIIGWPGGSGDGIFSPGGAISNMYA  250

251  MLIARYKMFPEVKEKGMAAVPRLLIAFTSEHSHFSLKKGAAALGIGTDSVI  300
     | :||| ||||||||||||| |||||||||||||||||||||||||||||
251  MMIARFKMFPEVKEKGMAALPRLLIAFTSEHSHFSLKKGAAALGIGTDSVI  300

301  LIKCDERGKMIPSDLERRILEVKQKGFVPFLVSATAGTTVYGAFDPLLAV  350
     |||||||||||||||||||| ||:|||||||||||||||||||||||||
301  LIKCDERGKMIPSDLERRILEAKQKGFVPFLVSATAGTTVYGAFDPLLAV  350

351  ADICKKYKIWMHVDAAWGGGLLMSRKHKWKLNGVERANSVTWNPHKMMGV  400
     ||||||||||||||||||||||||||||||||||||||||||||:|||
351  ADICKKYKIWMHVDAAWGGGLLMSRKHKWKLSGVERANSVTWNPHKMMGV  400
```

FIG._4A

```
401  PLQCSALLVREEGLMQSCNQMHASYLFQQDKHYDLSYDTGDKALQCGRHV  450
     |||||||||||||||| |||||||||||||||||||||||||||||||||
401  PLQCSALLVREEGLMQNCNQMHASYLFQQDKHYDLSYDTGDKALQCGRHV  450

451  DVFKLWLMWRAKGTTGFEAHIDKCLELAEYLYNIIKNREGYEMVFDGKPQ  500
     |||||||||||||||||||:::||||||||||||||||||||||||||:
451  DVFKLWLMWRAKGTTGFEAHVDKCLELAEYLYNIIKNREGYEMVFDGKPQ  500

501  HTNVCFWFVPPSLRVLEDNEERMSRLSKVAPVIKARMMEYGTTMVSYQPL  550
     |||||||:|||||:||||||||||||||||||||||||||||||||||||
501  HTNVCFWYIPPSLRTLEDNEERMSRLSKVAPVIKARMMEYGTTMVSYQPL  550

551  GDKVNFFRMVISNPAATHQDIDFLIEEIERLGQDL  585
     ||||||||||||||||||||||||||||||||||
551  GDKVNFFRMVISNPAATHQDIDFLIEEIERLGQDL  585
```

FIG._4B

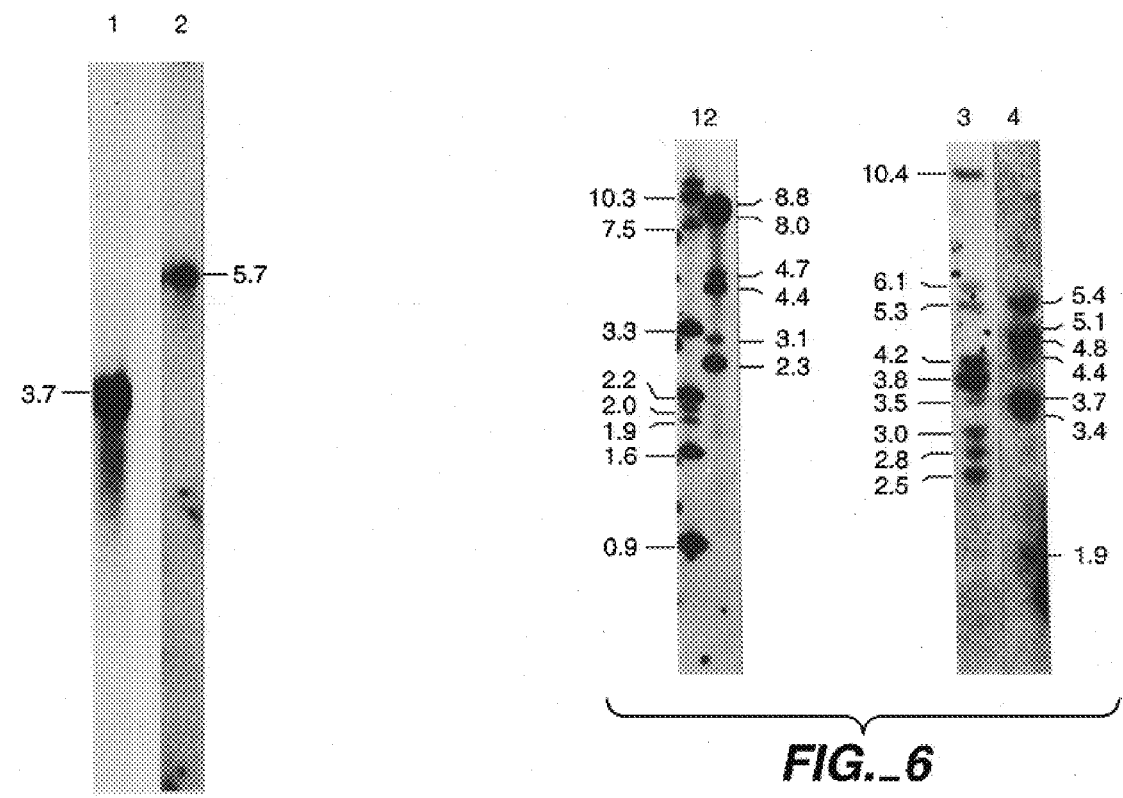
FIG._5
FIG._6

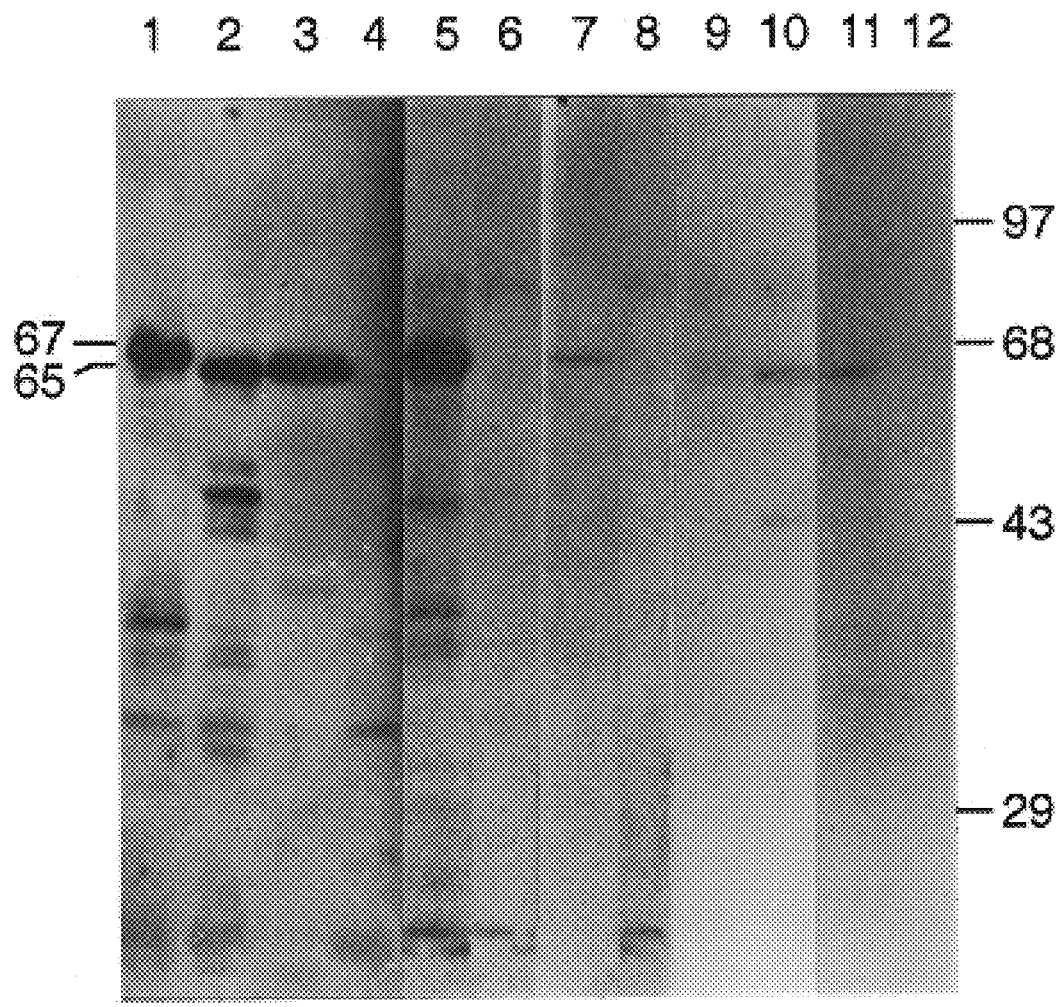
FIG._7

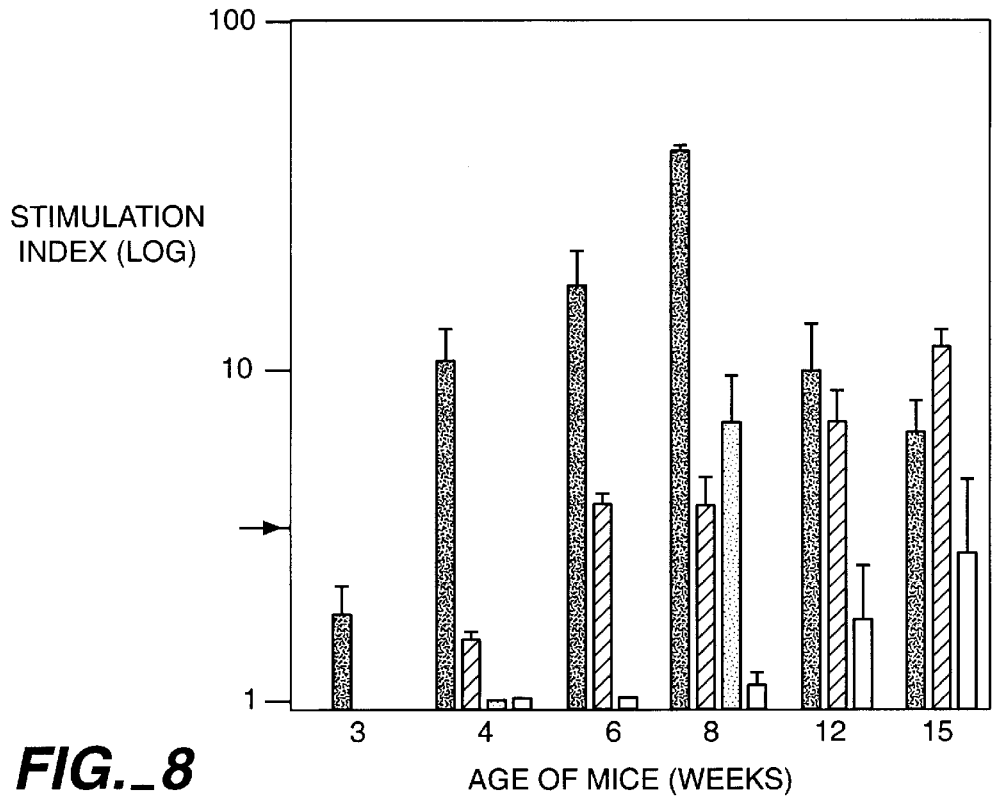
FIG._8
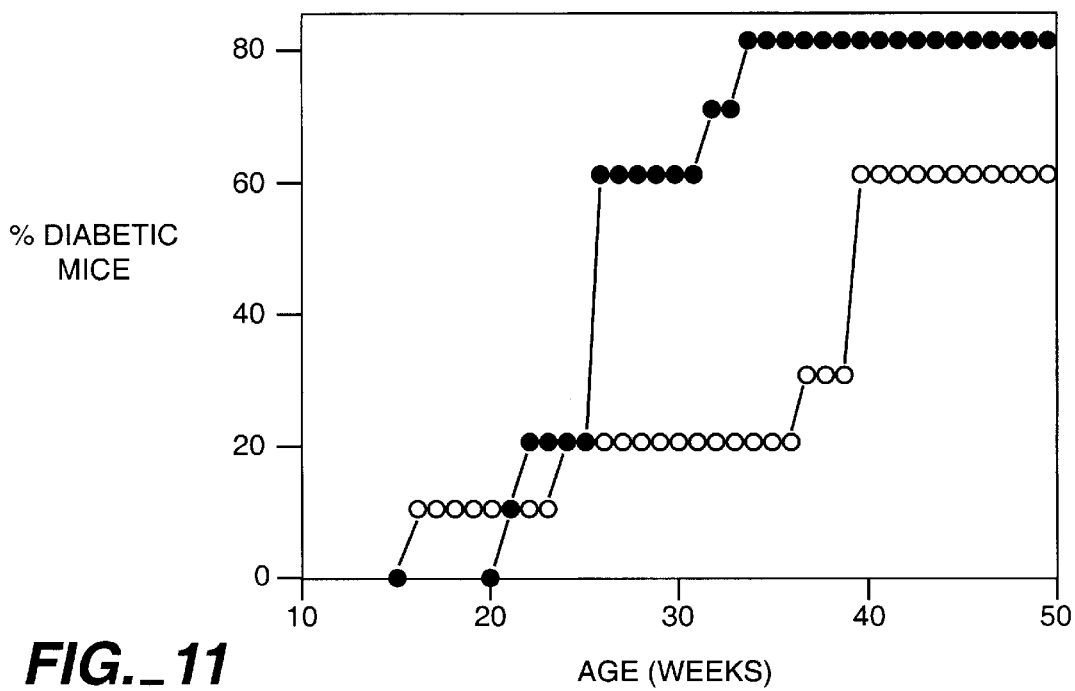
FIG._11

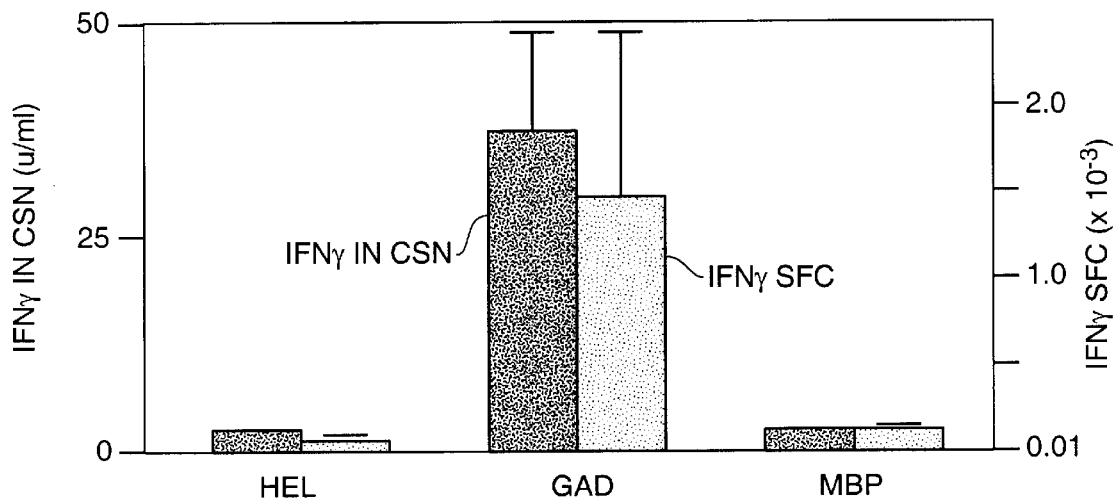
FIG._9A
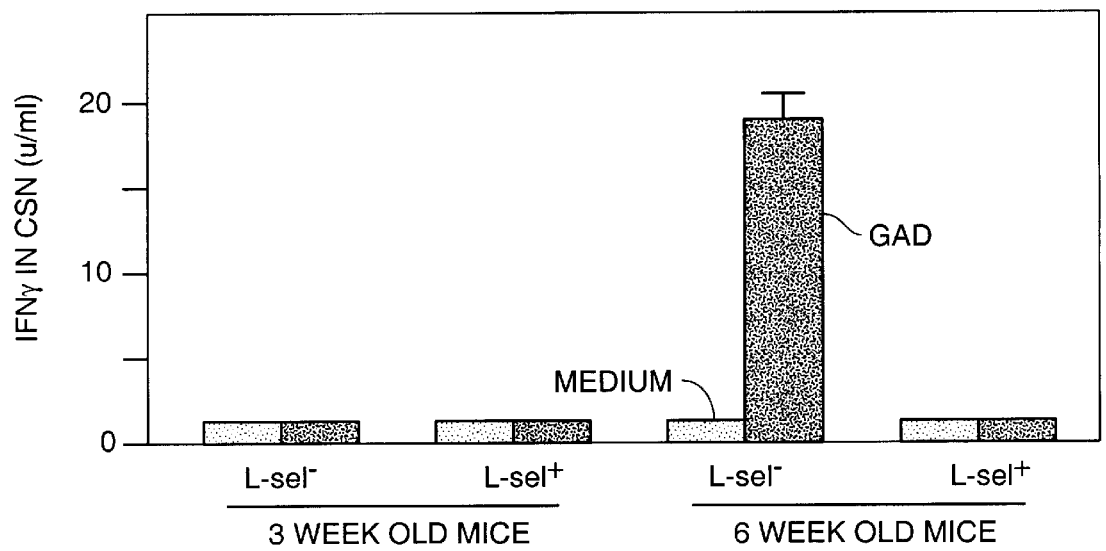
FIG._9B

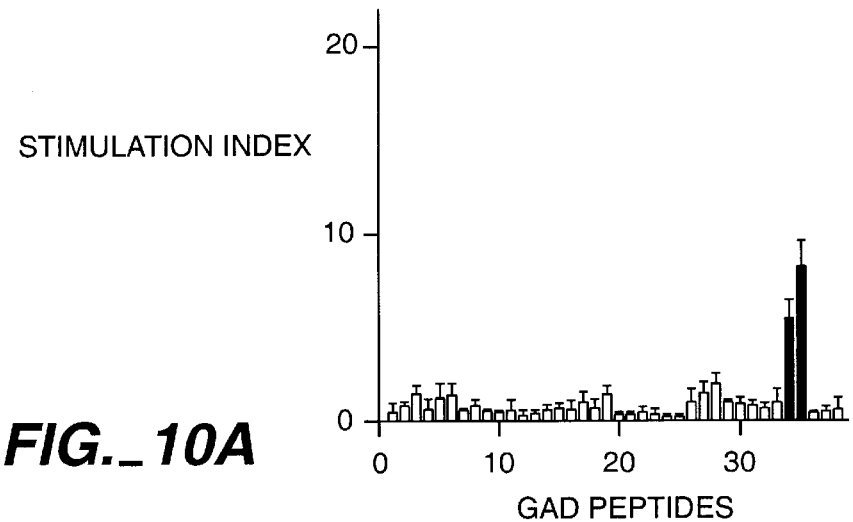
FIG._10A
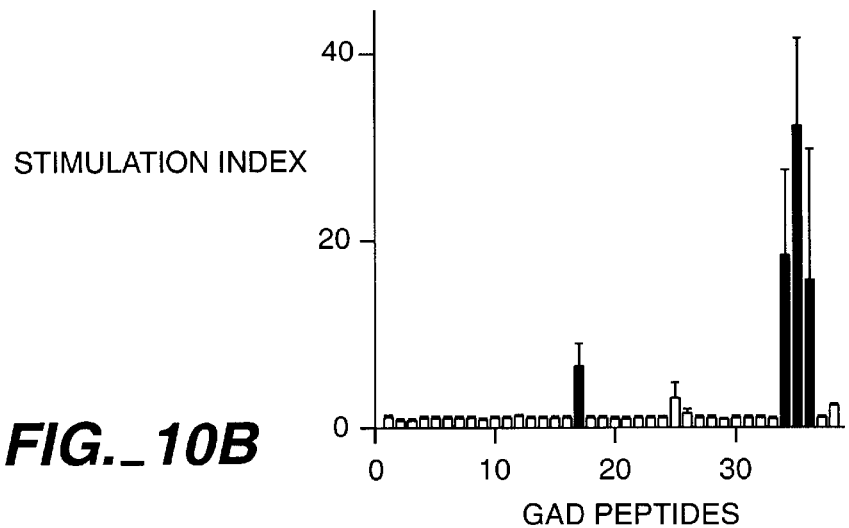
FIG._10B
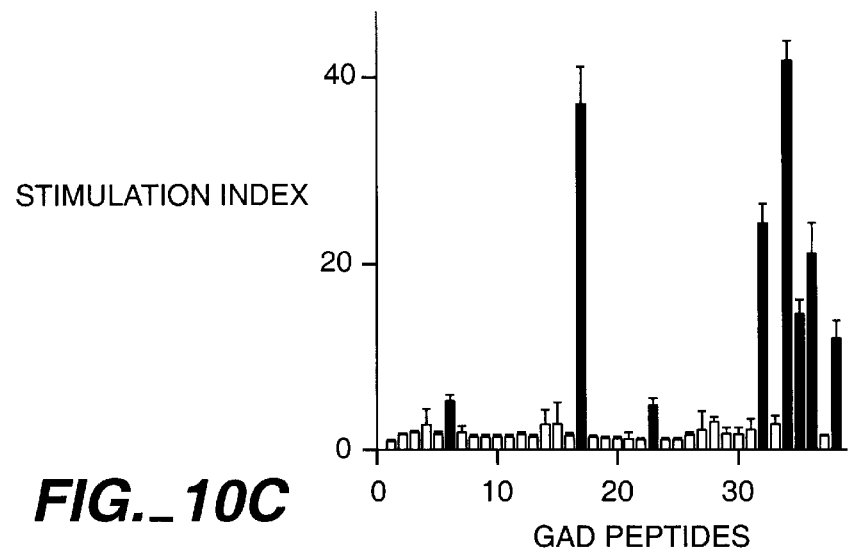
FIG._10C

```
SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Ser Ile Ala Ala Arg Tyr Lys Tyr Phe Pro Glu Val Lys Thr Lys Gly
    1               5                  10                  15

Met Ala Ala Val Pro Lys Leu
                20

(2) INFORMATION FOR SEQ ID NO:2:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Ala Met Met Ile Ala Arg Phe Lys Met Phe Pro Glu Val Lys Glu Lys
    1               5                  10                  15

Gly Met Ala Ala Leu Pro Arg Leu
                20

(2) INFORMATION FOR SEQ ID NO:3:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Phe Ile Glu Trp Leu Lys Val Lys Ile Leu Pro Glu Val Lys Glu Lys
    1               5                  10                  15

His Glu Phe Leu Ser Arg Leu
                20
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Lys Ser Met Cys Pro Gln Ala Gln Leu Lys Val Lys Tyr Leu
 1               5                  10                  15
```

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Ala Arg Phe Lys Met Phe Pro Glu Val Lys Glu Lys Gly Met Ala Ala
 1               5                  10                  15
```

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Lys Pro Cys Ser Cys Ser Lys Val Asp Val Asn Tyr Ala Phe Leu His
 1               5                  10                  15
Ala Thr Asp Leu
            20
```

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Asn Met Tyr Ala Met Met Ile Ala Arg Phe Lys Met Phe Pro Glu Val
 1               5                  10                  15
Lys Glu Lys Gly
            20
```

(2) INFORMATION FOR SEQ ID NO:8:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Thr Ala Gly Thr Thr Val Tyr Gly Ala Phe Asp Pro Leu Leu Ala Val
    1               5                   10                  15

Ala Asp Ile Cys Lys Lys
                20

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Glu Tyr Leu Tyr Asn Ile Ile Lys Asn Arg Glu Gly Tyr Glu Met Val
    1               5                   10                  15

Phe Asp Gly Lys
                20

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Ile Pro Pro Ser Leu Arg Tyr Leu Glu Asp Asn Glu Glu Arg Met Ser
    1               5                   10                  15

Arg Leu Ser Lys
                20

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Ser Arg Leu Ser Lys Val Ala Pro Val Ile Lys Ala Arg Met Met Glu
    1               5                   10                  15

Tyr Gly Thr Thr
                20

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Glu Tyr Gly Thr Thr Met Val Ser Tyr Gln Pro Leu Gly Asp Lys Val

```
                       1               5              10              15

Asn Phe Phe Arg
                     20

(2) INFORMATION FOR SEQ ID NO:13:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:13:

Ala Thr His Gln Asp Ile Asp Phe Leu Ile Glu Glu Ile Glu Arg Leu
     1               5              10                  15

Gly Gln Asp Leu
                 20

(2) INFORMATION FOR SEQ ID NO:14:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:14:

Met Ala Ser Pro Gly Ser Gly Phe Trp Ser Phe Gly Ser Glu Asp Gly
     1               5              10                  15

Ser Gly Asp Ser
                 20

(2) INFORMATION FOR SEQ ID NO:15:

(i) SEQUENCE CHARACTERISTICS:
         (A) LENGTH: 23 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:15:

Gly Ser Gly Asp Ser Glu Asn Pro Gly Thr Ala Arg Ala Trp Cys Gln
     1               5              10                  15

Val Ala Gln Lys Phe Thr Gly
                 20

(2) INFORMATION FOR SEQ ID NO:16:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:16:

Gln Lys Phe Thr Gly Gly Ile Gly Ile Gly Asn Lys Leu Cys Ala Leu
     1               5              10                  15

Leu Tyr Gly Asp
                 20
```

(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Leu Leu Tyr Gly Asp Ala Glu Lys Pro Ala Glu Ser Gly Gly Ser Gln
1               5                  10                  15

Pro Pro Arg Ala
            20
```

(2) INFORMATION FOR SEQ ID NO:18:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Gln Pro Pro Arg Ala Ala Ala Arg Lys Ala Ala Cys Ala Cys Asp Gln
1               5                  10                  15

Lys Pro Cys Ser Cys
            20
```

(2) INFORMATION FOR SEQ ID NO:19:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Lys Pro Cys Ser Cys Ser Lys Val Asp Val Asn Tyr Ala Phe Leu His
1               5                  10                  15

Ala Thr Asp Leu
            20
```

(2) INFORMATION FOR SEQ ID NO:20:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
His Ala Thr Asp Leu Leu Pro Ala Cys Asp Gly Glu Arg Pro Thr Leu
1               5                  10                  15

Ala Phe Leu Gln
            20
```

(2) INFORMATION FOR SEQ ID NO:21:

```
    (i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:21:

Leu Ala Phe Leu Gln Asp Val Met Asn Ile Leu Leu Gln Tyr Val Val
    1               5                   10                  15

Lys Ser Phe Asp Arg Ser
              20

(2) INFORMATION FOR SEQ ID NO:22:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:22:

Ser Phe Asp Arg Ser Thr Lys Val Ile Asp Phe His Tyr Pro Asn Glu
    1               5                   10                  15

Leu Leu Gln Glu
              20

(2) INFORMATION FOR SEQ ID NO:23:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:23:

Glu Leu Leu Gln Glu Tyr Asn Trp Glu Leu Ala Asp Gln Pro Gln Asn
    1               5                   10                  15

Leu Glu Glu Ile Leu Met
              20

(2) INFORMATION FOR SEQ ID NO:24:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:24:

Glu Glu Ile Leu Met His Cys Gln Thr Thr Leu Lys Tyr Ala Ile Lys
    1               5                   10                  15

Thr Gly His Pro
              20

(2) INFORMATION FOR SEQ ID NO:25:

(i) SEQUENCE CHARACTERISTICS:
         (A) LENGTH: 20 amino acids
         (B) TYPE: amino acid
         (C) STRANDEDNESS: single
```

-continued (D) TOPOLOGY: linear (ii) MOLECULE TYPE: peptide (xi) SEQUENCE DESCRIPTION: SEQ ID NO:25:

Lys Tyr Gly His Pro Arg Tyr Phe Asn Gln Leu Ser Thr Gly Leu Asp
   1               5                  10                  15

Met Val Gly Leu
              20

(2) INFORMATION FOR SEQ ID NO:26:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:26:

Asp Met Val Gly Leu Ala Ala Asp Trp Leu Thr Ser Thr Ala Asn Thr
   1               5                  10                  15

Asn Met Phe Thr
              20

(2) INFORMATION FOR SEQ ID NO:27:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:27:

Thr Asn Met Phe Thr Tyr Glu Ile Ala Pro Val Phe Val Leu Leu Glu
   1               5                  10                  15

Tyr Val Thr Leu
              20

(2) INFORMATION FOR SEQ ID NO:28:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:28:

Glu Tyr Val Thr Leu Lys Lys Met Arg Glu Ile Ile Gly Trp Pro Gly
   1               5                  10                  15

Gly Ser Gly Asp
              20

(2) INFORMATION FOR SEQ ID NO:29:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:29:

Gly Gly Ser Gly Asp Gly Ile Phe Ser Pro Gly Ala Ile Ser Asn
    1               5                  10                  15

Met Tyr Ala Met
                20

(2) INFORMATION FOR SEQ ID NO:30:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Asn Met Tyr Ala Met Met Ile Ala Arg Phe Lys Met Phe Pro Glu Val
    1               5                  10                  15

Lys Glu Lys Gly
                20

(2) INFORMATION FOR SEQ ID NO:31:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Pro Glu Val Lys Glu Lys Gly Met Ala Ala Leu Pro Arg Leu Ile Ala
    1               5                  10                  15

Phe Thr Ser Glu
                20

(2) INFORMATION FOR SEQ ID NO:32:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Ala Phe Thr Ser Glu His Ser His Phe Ser Leu Lys Lys Gly Ala Ala
    1               5                  10                  15

Ala Leu Gly Ile
                20

(2) INFORMATION FOR SEQ ID NO:33:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Ala Ala Leu Gly Ile Gly Thr Asp Ser Val Ile Leu Ile Lys Cys Asp
    1               5                  10                  15

Glu Arg Gly Lys
            20

(2) INFORMATION FOR SEQ ID NO:34:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

Asp Glu Arg Gly Lys Met Ile Pro Ser Asp Leu Glu Arg Arg Ile Leu
    1               5                  10                  15

Glu Ala Lys Gln
            20

(2) INFORMATION FOR SEQ ID NO:35:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Leu Glu Ala Lys Gln Lys Gly Phe Val Pro Phe Leu Val Ser Ala Thr
    1               5                  10                  15

Ala Gly Thr Thr
            20

(2) INFORMATION FOR SEQ ID NO:36:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Thr Ala Phe Thr Thr Val Tyr Gly Ala Phe Asp Pro Leu Leu Ala Val
    1               5                  10                  15

Ala Asp Ile Cys Lys Lys
            20

(2) INFORMATION FOR SEQ ID NO:37:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Asp Ile Cys Lys Lys Tyr Lys Ile Trp Met His Val Asp Ala Ala Trp
    1               5                  10                  15

Gly Gly Gly Leu Leu Met Ser
            20

(2) INFORMATION FOR SEQ ID NO:38:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
Gly Leu Leu Met Ser Arg Lys His Lys Trp Lys Leu Ser Gly Val Glu
1               5                  10                  15

Arg Ala Asn Ser
            20
```

(2) INFORMATION FOR SEQ ID NO:39:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Glu Arg Ala Asn Ser Val Thr Trp Asn Pro His Lys Met Met Gly Val
1               5                  10                  15

Pro Leu Gln Cys
            20
```

(2) INFORMATION FOR SEQ ID NO:40:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

```
Val Pro Leu Gln Cys Ser Ala Leu Leu Val Arg Glu Glu Gly Leu Met
1               5                  10                  15

Gln Asn Cys Asn Gln
            20
```

(2) INFORMATION FOR SEQ ID NO:41:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

```
Gln Asn Cys Asn Gln Met His Ala Ser Tyr Leu Phe Gln Gln Asp Lys
1               5                  10                  15

His Tyr Asp Leu
            20
```

(2) INFORMATION FOR SEQ ID NO:42:

(i) SEQUENCE CHARACTERISTICS:

(A) LENGTH: 20 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:42:

Lys His Tyr Asp Leu Ser Tyr Asp Thr Gly Asp Lys Ala Leu Gln Cys
    1               5                   10                  15

Gly Arg His Val
                20

(2) INFORMATION FOR SEQ ID NO:43:

(i) SEQUENCE CHARACTERISTICS:
          (A) LENGTH: 21 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:43:

Cys Gly Arg His Val Asp Val Phe Lys Leu Trp Leu Met Trp Arg Ala
    1               5                   10                  15

Lys Gly Thr Thr Gly
                20

(2) INFORMATION FOR SEQ ID NO:44:

(i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:44:

Lys Gly Thr Thr Gly Phe Glu Ala His Val Asp Lys Cys Leu Glu Leu
    1               5                   10                  15

Ala Glu Tyr Leu Tyr Asn
                20

(2) INFORMATION FOR SEQ ID NO:45:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:45:

Glu Tyr Leu Tyr Asn Ile Ile Lys Asn Arg Glu Gly Tyr Glu Met Val
    1               5                   10                  15

Phe Asp Gly Lys
                20

(2) INFORMATION FOR SEQ ID NO:46:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:46:

Val Phe Asp Gly Lys Pro Gln His Thr Asn Val Cys Phe Trp Tyr Ile
        1               5                  10                  15

Pro Pro Ser Leu
                    20

(2) INFORMATION FOR SEQ ID NO:47:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:47:

Ile Pro Pro Ser Leu Arg Thr Leu Glu Asp Asn Glu Glu Arg Met Ser
        1               5                  10                  15

Arg Leu Ser Lys
                    20

(2) INFORMATION FOR SEQ ID NO:48:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:48:

Ser Arg Leu Ser Lys Val Ala Pro Val Ile Lys Ala Arg Met Met Glu
        1               5                  10                  15

Tyr Gly Thr Thr
                    20

(2) INFORMATION FOR SEQ ID NO:49:

(i) SEQUENCE CHARACTERISTICS:
             (A) LENGTH: 21 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:49:

Glu Tyr Gly Thr Thr Thr Met Val Ser Tyr Gln Pro Leu Gly Asp Lys
        1               5                  10                  15

Val Asn Phe Phe Arg
                    20

(2) INFORMATION FOR SEQ ID NO:50:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:50:

```
Val Asn Phe Phe Arg Met Val Ile Ser Asn Pro Ala Ala Thr His Gln
1               5                   10                  15

Asp Ile Asp Phe
            20
```

(2) INFORMATION FOR SEQ ID NO:51:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

```
Ala Thr His Gln Asp Ile Asp Phe Leu Ile Glu Glu Ile Glu Arg Leu
1               5                   10                  15

Gly Gln Asp Leu
            20
```

(2) INFORMATION FOR SEQ ID NO:52:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

```
Tyr Glu Ile Ala Pro Val Phe Val Leu Met Gln Ile Thr Leu Lys
1               5                   10                  15

Lys Met Arg Glu Ile Val Gly Trp Ser Ser Lys Asp Gly Asp Gly Ile
                20                  25                  30

Phe Ser Pro Gly Gly Ala Ile Ser Asn Met Tyr Ser Ile Met Ala Ala
            35                  40                  45

Arg Tyr Lys Phe Phe Pro Glu Val Lys Thr Lys Gly
50                  55                  60
```

(2) INFORMATION FOR SEQ ID NO:53:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

```
Tyr Glu Ile Ala Pro Val Phe Val Leu Leu Glu Tyr Val Arg Glu Ile
1               5                   10                  15

Ile Gly Trp Pro Gly Gly Ser Asp Gly Ile Phe Ser Pro Gly Gly Ala
            20                  25                  30

Ile Ser Asn Tyr Ala Met Leu Ile Ala Arg Tyr Lys Met Phe Pro Glu
            35                  40                  45

Val Lys Glu Lys Gly
            50
```

(2) INFORMATION FOR SEQ ID NO:54:

(i) SEQUENCE CHARACTERISTICS:

(A) LENGTH: 2026 base pairs
        (B) TYPE: nucleic acid
        (C) STRANDEDNESS: single
        (D) TOPOLOGY: linear (xi) SEQUENCE DESCRIPTION: SEQ ID NO:54:

```
GGGCGTGCGG GGTCGAGCCG AAGCAGCTTG CCCGCAGCCA CTCGGAGGCG ACCAGCGCCA    60
GACTAGCAGA ACCCATGGCA TCTCCGGGCT CTGGCTTTTG GTCCTTCGGA TCTGAAGATG   120
GCTCTGGGGA TCCTGAGAAC CCGGGAACAG CGAGAGCCTG GTGCCAGGTG GCCCAAAAGT   180
TCACGGGCGG CATCGGAAAC AAGCTATGCG CTCTGCTCTA CGGAGACTCT GAGAAGCCAG   240
CAGAGAGCGG CGGGAGCGTG ACCTCGCGGG CCGCCACTCG GAAGGTCGCC TGCACCTGTG   300
ACCAAAAACC CTGCAGCTGC CCCAAAGGAG ATGTCAATTA TGCACTTCTC CACGCAACAG   360
ACCTGCTGCC AGCCTGTGAA GGAGAAAGGC CCACTCTCGC ATTTCTGCAA GATGTAATGA   420
ACATTTTGCT TCAGTACGTG GTGAAAAGTT TTGATAGATC AACTAAAGTG ATTGATTTCC   480
ATTACCCCAA TGAGCTTCTT CAAGAGTATA ATTGGGAATT GGCAGACCAA CCGCAAAATC   540
TGGAGGAAAT TTTGACGCAC TGCCAAACAA CTCTAAAATA TGCGATTAAA ACAGGGCATC   600
CCCGATATTT TAATCAGCTG TCTACCGGAT TGGATATGGT TGGATTAGCA GCAGATTGGT   660
TGACATCAAC AGCAAACACG AACATGTTTA CCTATGAGAT CGCCCCTGTA TTTGTACTAC   720
TGGAATATGT GACACTAAAG AAAATGAGGG AAATCATTGG CTGGCCAGGA GGCTCTGGCG   780
ATGGAATCTT TTCTCCTGGT GGTGCCATCT CCAACATGTA CGCCATGCTC ATTGCCCGCT   840
ATAAGATGTT TCCAGAAGTC AAGGAAAAGG GGATGGCGGC GGTGCCCAGG CTCATCGCAT   900
TCACGTCAGA GCATAGTCAC TTTTCTCTCA AGAAGGGAGC TGCAGCCTTG GGATCGGAA    960
CAGACAGCGT GATTCTGATT AAATGTGATG AGAGAGGGAA AATGATCCCA TCTGACCTTG  1020
AAAGAAGAAT CCTTGAAGTC AAACAGAAAG GATTTGTTCC TTTCCTGGTG AGTGCCACAG  1080
AAAGAAGAAT CCTTGAAGTC AAACAGAAAG GATTTGTTCC TTTCCTGGTG AGTGCCACAG  1140
CTGGAACCAC TGTGTACGGG GCTTTTGATC CTCTCTTGGC TGTAGCTGAC ATCTGCAAAA  1200
AATATAAGAT CTGGATGCAT GTGGATGCTG CTTGGGGTGG AGGGTTACTG ATGTCTCGGA  1260
AACACAAGTG GAAGCTGAAC GGTGTGGAGA GGGCCAACTC TGTGACATGG AATCCCCACA  1320
AGATGATGGG TGTCCCCTTG CAATGTTCGG CTCTCCTGGT CAGAGAGGAG GGACTGATGC  1380
AGAGCTGCAA CCAGATGCAT GCTTCCTACC TCTTTCAGCA AGATAAGCAC TATGACCTGT  1440
CCTATGACAC GGGAGACAAG GCCTTGCAGT GTGGACGCCA CGTCGATGTC TTTAAATTAT  1500
GGCTCATGTG GAGAGCAAAG GGGACTACTG GATTTGAAGC TCACATTGAT AAGTGTTTGG  1560
AGCTGGCAGA GTATTTATAC AATATCATTA AAAACCGAGA AGGATATGAA ATGGTGTTCG  1620
ATGGGAAGCC TCAGCACACA AATGTCTGCT TCTGGTTTGT ACCTCCTAGT TTGCGAGTTC  1680
TGGAAGACAA TGAAGAGAGA ATGAGCCGCC TCTCAAAGGT GGCGCCAGTG ATTAAAGCCA  1740
GAATGATGGA GTATGGGACC ACAATGGTCA GCTACCAACC CTTAGGAGAT AAGGTCAACT  1800
TCTTCCGCAT GGTCATCTCA AACCCTGCAG CAACTCACCA AGACATTGAC TTCCTCATTG  1860
AAGAAATCGA ACGCCTGGGA CAAGATTTGT AATCACTTTG CTCACCAAAC TTTCAGTTCT  1920
CTAGGTAGAC AGCTAAGTTG TCACAAACTG TGTAAATGTA TTTGTAGTTT GTTCCAGAGT  1980
AATTCTATTT CTATATCGTG GTGTCACAGT AGAGTCCAGT TTAAAA             2026
```

(2) INFORMATION FOR SEQ ID NO:55:

(i) SEQUENCE CHARACTERISTICS:
        (A) LENGTH: 605 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:55:

```
Met Ala Ser Pro Gly Ser Gly Phe Trp Ser Phe Gly Ser Glu Asp Gly
 1               5                  10                  15

Ser Gly Asp Pro Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ser Glu Lys Pro Ala Glu Ser Gly Gly Ser Val Thr Ser
50                  55                  60

Arg Ala Ala Thr Arg Lys Val Ala Cys Thr Cys Asp Gln Lys Pro Cys
65                  70                  75                  80

Ser Cys Pro Lys Gly Asp Val Asn Tyr Ala Leu Leu His Ala Thr Asp
                85                  90                  95

Leu Leu Pro Ala Cys Glu Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Thr His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Leu Ile Ala Arg Tyr
                245                 250                 255

Lys Met Phe Pro Glu Val Lys Glu Lys Gly Met Ala Ala Val Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
290                 295                 300

Asp Glu Arg Gly Lys Met Ile Pro Ser Asp Leu Glu Arg Arg Ile Leu
305                 310                 315                 320

Glu Val Lys Gln Lys Gly Phe Val Pro Phe Leu Val Ser Ala Thr Ala
                325                 330                 335

Arg Arg Ile Leu Glu Val Lys Gln Lys Gly Phe Val Pro Phe Leu Val
            340                 345                 350

Ser Ala Thr Ala Gly Thr Thr Val Tyr Gly Ala Phe Asp Pro Leu Leu
        355                 360                 365

Ala Val Ala Asp Ile Cys Lys Lys Tyr Lys Ile Trp Met His Val Asp
370                 375                 380
```

```
Ala Ala Trp Gly Gly Gly Leu Leu Met Ser Arg Lys His Lys Trp Lys
385                 390                 395                 400

Leu Asn Gly Val Glu Arg Ala Asn Ser Val Thr Trp Asn Pro His Lys
            405                 410                 415

Met Met Gly Val Pro Leu Gln Cys Ser Ala Leu Leu Val Arg Glu Glu
            420                 425                 430

Gly Leu Met Gln Ser Cys Asn Gln Met His Ala Ser Tyr Leu Phe Gln
        435                 440                 445

Gln Asp Lys His Tyr Asp Leu Ser Tyr Asp Thr Gly Asp Lys Ala Leu
    450                 455                 460

Gln Cys Gly Arg His Val Asp Val Phe Lys Leu Trp Leu Met Trp Arg
465                 470                 475                 480

Ala Lys Gly Thr Thr Gly Phe Glu Ala His Ile Asp Lys Cys Leu Glu
                485                 490                 495

Leu Ala Glu Tyr Leu Tyr Asn Ile Ile Lys Asn Arg Glu Gly Tyr Glu
            500                 505                 510

Met Val Phe Asp Gly Lys Pro Gln His Thr Asn Val Cys Phe Trp Phe
        515                 520                 525

Val Pro Pro Ser Leu Arg Val Leu Glu Asp Asn Glu Glu Arg Met Ser
    530                 535                 540

Arg Leu Ser Lys Val Ala Pro Val Ile Lys Ala Arg Met Met Glu Tyr
545                 550                 555                 560

Gly Thr Thr Met Val Ser Tyr Gln Pro Leu Gly Asp Lys Val Asn Phe
                565                 570                 575

Phe Arg Met Val Ile Ser Asn Pro Ala Ala Thr His Gln Asp Ile Asp
            580                 585                 590

Phe Leu Ile Glu Glu Ile Glu Arg Leu Gly Gln Asp Leu
        595                 600                 605

(2) INFORMATION FOR SEQ ID NO:56:

(i) SEQUENCE CHARACTERISTICS:
        (A) LENGTH: 2100 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

AGCTCGCCCG CAGCTCGCAC TCGCAGGCGA CCTGCTCCAG TCTCCAAAGC CGATGGCATC      60

TCCGGGCTCT GGCTTTTGGT CTTTCGGGTC GGAAGATGGC TCTGGGGATT CCGAGAATCC     120

CGGCACAGCG CGAGCCTGGT GCCAAGTGGC TCAGAAGTTC ACGGGCGGCA TCGGAAACAA     180

ACTGTGCGCC CTGCTCTACG GAGACGCCGA GAAGCCGGCG GAGAGCGGCG GGAGCCAACC     240

CCCGCGGGCC GCCGCCCGGA AGGCCGCCTG CGCCTGCGAC CAGAAGCCCT GCAGCTGCTC     300

CAAAGTGGAT GTCAACTACG CGTTTCTCCA TGCAACAGAC CTGCTGCCGG CGTGTGATGG     360

AGAAAGGCCC ACTTTGGCGT TTCTGCAAGA TGTTATGAAC ATTTTACTTC AGTATGTGGT     420

GAAAAGTTTC GATAGATCAA CCAAAGTGAT TGATTTCCAT TATCCTAATG AGCTTCTCCA     480

AGAATATAAT TGGGAATTGG CAGACCAACC ACAAAATTTG GAGGAAATTT TGATGCATTG     540

CCAAACAACT CTAAAATATG CAATTAAAAC AGGGCATCCT AGATACTTCA ATCAACTTTC     600

TACTGGTTTG GATATGGTTG GATTAGCAGC AGACTGGCTG ACATCAACAG CAAATACTAA     660

CATGTTCACC TATGAAATTG CTCCAGTATT TGTGCTTTTG GAATATGTCA CACTAAAGAA     720

AATGAGAGAA ATCATTGGCT GGCCAGGGGG CTCTGGCGAT GGGATATTTT CTCCCGGTGG     780
```

```
CGCCATATCT AACATGTATG CCATGATGAT CGCACGCTTT AAGATGTTCC CAGAAGTCAA  840

GGAGAAAGGA ATGGCTGCTC TTCCCAGGCT CATTGCCTTC ACGTCTGAAC ATAGTCATTT  900

TTCTCTCAAG AAGGGAGCTG CAGCCTTAGG GATTGGAACA GACAGCGTGA TTCTGATTAA  960

ATGTGATGAG AGAGGGAAAA TGATTCCATC TGATCTTGAA AGAAGGATTC TTGAAGCCAA 1020

ACAGAAAGGG TTTGTTCCTT TCCTCGTGAG TGCCACAGCT GGAACCACCG TGTACGGAGC 1080

ATTTGACCCC CTCTTAGCTG TCGCTGACAT TTGCAAAAAG TATAAGATCT GGATGCATGT 1140

GGATGCAGCT TGGGGTGGGG GATTACTGAT GTCCCGAAAA CACAAGTGGA AACTGAGTGG 1200

CGTGGAGAGG GCCAACTCTG TGACGTGGAA TCCACACAAG ATGATGGGAG TCCCTTTGCA 1260

GTGCTCTGCT CTCCTGGTTA GAGAAGAGGG ATTGATGCAG AATTGCAACC AAATGCATGC 1320

CTCCTACCTC TTTCAGCAAG ATAAACATTA TGACCTGTCC TATGACACTG AGACAAGGC  1380

CTTACAGTGC GGACGCCACG TTGATGTTTT TAAACTATGG CTGATGTGGA GGGCAAAGGG 1440

GACTACCGGG TTTGAAGCGC ATGTTGATAA ATGTTTGGAG TTGGCAGAGT ATTTATACAA 1500

CATCATAAAA AACCGAGAAG GATATGAGAT GGTGTTTGAT GGGAAGCCTC AGCACACAAA 1560

TGTCTGCTTC TGGTACATTC CTCCAAGCTT GCGTACTCTG GAAGACAATG AAGAGAGAAT 1620

GAGTCGCCTC TCGAAGGTGG CTCCAGTGAT TAAAGCCAGA ATGATGGAGT ATGGAACCAC 1680

AATGGTCAGC TACCAACCCT TGGGAGACAA GGTCAATTTC TTCCGCATGG TCATCTCAAA 1740

CCCAGCGGCA ACTCACCAAG ACATTGACTT CCTGATTGAA GAAATAGAAC GCCTTGGACA 1800

AGATTTATAA TAACCTTGCT CACCAAGCTG TTCCACTTCT CTAGGTAGAC AATTAAGTTG 1860

TCACAAACTG TGTGAATGTA TTTGTAGTTT GTTCCAAAGT AAATCTATTT CTATATTGTG 1920

GTGTCAAAGT AGAGTTTAAA AATTAAACAA AAAAGACATT GCTCCTTTTA AAAGTCCTTT 1980

CTTAAGTTTA GAATACCTCT CTAAGAATTC GTGACAAAAG GCTATGTTCT AATCAATAAG 2040

GAAAAGCTTA AAATTGTTAT AAATACTTCC CTTACTTTTA ATATAGTGTG CAAAGCAAAC 2100
```

(2) INFORMATION FOR SEQ ID NO:57:

(i) SEQUENCE CHARACTERISTICS:
        (A) LENGTH: 585 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:57:

```
Met Ala Ser Pro Gly Ser Gly Phe Trp Ser Phe Gly Ser Glu Asp Gly
 1               5                  10                  15

Ser Gly Asp Ser Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
            35                  40                  45

Tyr Gly Asp Ala Glu Lys Pro Ala Glu Ser Gly Gly Ser Gln Pro Pro
        50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
```

```
            115                 120                 125
Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
            195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
                260                 265                 270

Leu Ile Ala Phe Thr Ser Glu His Ser His Phe Ser Leu Lys Lys Gly
            275                 280                 285

Ala Ala Ala Leu Gly Ile Gly Thr Asp Ser Val Ile Leu Ile Lys Cys
            290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
        370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
            435                 440                 445

His Val Asp Val Phe Lys Leu Trp Leu Met Trp Arg Ala Lys Gly Thr
        450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
            485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
        530                 535                 540
```

-continued

```
Val Ser Tyr Gln Pro Leu Gly Asp Lys Val Asn Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585
```

(2) INFORMATION FOR SEQ ID NO:58:

(i) SEQUENCE CHARACTERISTICS:
      (A) LENGTH: 585 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:58:

```
Met Ala Ser Pro Gly Ser Gly Phe Trp Ser Phe Gly Ser Glu Asp Gly
1               5                   10                  15

Ser Gly Asp Pro Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
                35                  40                  45

Tyr Gly Asp Ser Glu Lys Pro Ala Glu Ser Gly Gly Ser Val Thr Ser
50                  55                  60

Arg Ala Thr Arg Lys Val Ala Cys Thr Cys Asp Gln Lys Pro Cys
65                  70                  75                  80

Ser Cys Pro Lys Gly Asp Val Asn Tyr Ala Leu Leu His Ala Thr Asp
                85                  90                  95

Leu Leu Pro Ala Cys Glu Gly Glu Arg Pro Thr Leu Ala Phe Leu Gln
                100                 105                 110

Asp Val Met Asn Ile Leu Leu Gln Tyr Val Val Lys Ser Phe Asp Arg
                115                 120                 125

Ser Thr Lys Val Ile Asp Phe His Tyr Pro Asn Glu Leu Leu Gln Glu
                130                 135                 140

Tyr Asn Trp Glu Leu Ala Asp Gln Pro Gln Asn Leu Glu Glu Ile Leu
145                 150                 155                 160

Thr His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
                180                 185                 190

Ala Asp Trp Leu Thr Ser Thr Ala Asn Thr Asn Met Phe Thr Tyr Glu
                195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Leu Ile Ala Arg Tyr
                245                 250                 255

Lys Met Phe Pro Glu Val Lys Glu Lys Gly Met Ala Ala Val Pro Arg
                260                 265                 270

Leu Ile Ala Phe Thr Ser Glu His Ser His Phe Ser Leu Lys Lys Gly
                275                 280                 285

Ala Ala Ala Leu Gly Ile Gly Thr Asp Ser Val Ile Leu Ile Lys Cys
                290                 295                 300

Asp Glu Arg Gly Lys Met Ile Pro Ser Asp Leu Glu Arg Arg Ile Leu
```

```
              305                 310                 315                 320
    Glu Val Lys Gln Lys Gly Phe Val Pro Phe Leu Val Ser Ala Thr Ala
                    325                 330                 335
    Gly Thr Thr Val Tyr Gly Ala Phe Asp Pro Leu Leu Ala Val Ala Asp
                    340                 345                 350
    Ile Cys Lys Lys Tyr Lys Ile Trp Met His Val Asp Ala Ala Trp Gly
                    355                 360                 365
    Gly Gly Leu Leu Met Ser Arg Lys His Lys Trp Lys Leu Asn Gly Val
                    370                 375                 380
    Glu Arg Ala Asn Ser Val Thr Trp Asn Pro His Lys Met Met Gly Val
    385                 390                 395                 400
    Pro Leu Gln Cys Ser Ala Leu Leu Val Arg Glu Glu Gly Leu Met Gln
                    405                 410                 415
    Ser Cys Asn Gln Met His Ala Ser Tyr Leu Phe Gln Gln Asp Lys His
                    420                 425                 430
    Tyr Asp Leu Ser Tyr Asp Thr Gly Asp Lys Ala Leu Gln Cys Gly Arg
                    435                 440                 445
    His Val Asp Val Phe Lys Leu Trp Leu Met Trp Arg Ala Lys Gly Thr
                    450                 455                 460
    Thr Gly Phe Glu Ala His Ile Asp Lys Cys Leu Glu Leu Ala Glu Tyr
    465                 470                 475                 480
    Leu Tyr Asn Ile Ile Lys Asn Arg Glu Gly Tyr Glu Met Val Phe Asp
                    485                 490                 495
    Gly Lys Pro Gln His Thr Asn Val Cys Phe Trp Phe Val Pro Pro Ser
                    500                 505                 510
    Leu Arg Val Leu Glu Asp Asn Glu Glu Arg Met Ser Arg Leu Ser Lys
                    515                 520                 525
    Val Ala Pro Val Ile Lys Ala Arg Met Met Glu Tyr Gly Thr Thr Met
                    530                 535                 540
    Val Ser Tyr Gln Pro Leu Gly Asp Lys Val Asn Phe Phe Arg Met Val
    545                 550                 555                 560
    Ile Ser Asn Pro Ala Ala Thr His Gln Asp Ile Asp Phe Leu Ile Glu
                    565                 570                 575
    Glu Ile Glu Arg Leu Gly Gln Asp Leu
                    580                 585

(2) INFORMATION FOR SEQ ID NO:59:

(i) SEQUENCE CHARACTERISTICS:
        (A) LENGTH: 585 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

Met Ala Ser Pro Gly Ser Gly Phe Trp Ser Phe Gly Ser Glu Asp Gly
    1               5                   10                  15
    Ser Gly Asp Ser Glu Asn Pro Gly Thr Ala Arg Ala Trp Cys Gln Val
                    20                  25                  30
    Ala Gln Lys Phe Thr Gly Gly Ile Gly Asn Lys Leu Cys Ala Leu Leu
                    35                  40                  45
    Tyr Gly Asp Ala Glu Lys Pro Ala Glu Ser Gly Gly Ser Gln Pro Pro
                    50                  55                  60
    Arg Ala Ala Ala Arg Lys Ala Ala Cys Ala Cys Asp Gln Lys Pro Cys
    65                  70                  75                  80
```

-continued

```
Ser Cys Ser Lys Val Asp Val Asn Tyr Ala Phe Leu His Ala Thr Asp
            85                  90                  95
Leu Leu Pro Ala Cys Asp Gly Glu Arg Pro Thr Leu Ala Phe Leu Gln
            100                 105                 110
Asp Val Met Asn Ile Leu Leu Gln Tyr Val Val Lys Ser Phe Asp Arg
            115                 120                 125
Ser Thr Lys Val Ile Asp Phe His Tyr Pro Asn Glu Leu Leu Gln Glu
            130                 135                 140
Tyr Asn Trp Glu Leu Ala Asp Gln Pro Gln Asn Leu Glu Glu Ile Leu
145                 150                 155                 160
Met His Cys Gln Thr Thr Leu Lys Tyr Ala Ile Lys Thr Gly His Pro
            165                 170                 175
Arg Tyr Phe Asn Gln Leu Ser Thr Gly Leu Asp Met Val Gly Leu Ala
            180                 185                 190
Ala Asp Trp Leu Thr Ser Thr Ala Asn Thr Asn Met Phe Thr Tyr Glu
            195                 200                 205
Ile Ala Pro Val Phe Val Leu Leu Glu Tyr Val Thr Leu Lys Lys Met
            210                 215                 220
Arg Glu Ile Ile Gly Trp Pro Gly Gly Ser Gly Asp Gly Ile Phe Ser
225                 230                 235                 240
Pro Gly Gly Ala Ile Ser Asn Met Tyr Ala Met Met Ile Ala Arg Phe
            245                 250                 255
Lys Met Phe Pro Glu Val Lys Glu Lys Gly Met Ala Ala Leu Pro Arg
            260                 265                 270
Leu Ile Ala Phe Thr Ser Glu His Ser His Phe Ser Leu Lys Lys Gly
            275                 280                 285
Ala Ala Ala Leu Gly Ile Gly Thr Asp Ser Val Ile Leu Ile Lys Cys
            290                 295                 300
Asp Glu Arg Gly Lys Met Ile Pro Ser Asp Leu Glu Arg Arg Ile Leu
305                 310                 315                 320
Glu Ala Lys Gln Lys Gly Phe Val Pro Phe Leu Val Ser Ala Thr Ala
            325                 330                 335
Gly Thr Thr Val Tyr Gly Ala Phe Asp Pro Leu Leu Ala Val Ala Asp
            340                 345                 350
Ile Cys Lys Lys Tyr Lys Ile Trp Met His Val Asp Ala Ala Trp Gly
            355                 360                 365
Gly Gly Leu Leu Met Ser Arg Lys His Lys Trp Lys Leu Ser Gly Val
            370                 375                 380
Glu Arg Ala Asn Ser Val Thr Trp Asn Pro His Lys Met Met Gly Val
385                 390                 395                 400
Pro Leu Gln Cys Ser Ala Leu Leu Val Arg Glu Gly Leu Met Gln
            405                 410                 415
Asn Cys Asn Gln Met His Ala Ser Tyr Leu Phe Gln Gln Asp Lys His
            420                 425                 430
Tyr Asp Leu Ser Tyr Asp Thr Gly Asp Lys Ala Leu Gln Cys Gly Arg
            435                 440                 445
His Val Asp Val Phe Lys Leu Trp Leu Met Trp Arg Ala Lys Gly Thr
            450                 455                 460
Thr Gly Phe Glu Ala His Val Asp Lys Cys Leu Glu Leu Ala Glu Tyr
465                 470                 475                 480
Leu Tyr Asn Ile Ile Lys Asn Arg Glu Gly Tyr Glu Met Val Phe Asp
            485                 490                 495
Gly Lys Pro Gln His Thr Asn Val Cys Phe Trp Tyr Ile Pro Pro Ser
```

-continued

```
                500              505              510
Leu Arg Thr Leu Glu Asp Asn Glu Glu Arg Met Ser Arg Leu Ser Lys
            515              520              525

Val Ala Pro Val Ile Lys Ala Arg Met Met Glu Tyr Gly Thr Thr Met
530              535              540

Val Ser Tyr Gln Pro Leu Gly Asp Lys Val Asn Phe Phe Arg Met Val
545              550              555              560

Ile Ser Asn Pro Ala Ala Thr His Gln Asp Ile Asp Phe Leu Ile Glu
            565              570              575

Glu Ile Glu Arg Leu Gly Gln Asp Leu
            580              585
```

(2) INFORMATION FOR SEQ ID NO:60:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:60:

```
Gln Lys Phe Thr Gly Gly Ile Gly Asn Lys Leu Cys Ala Leu Leu Tyr
1               5                  10                  15

Gly Asp
```

METHOD FOR AMELIORATING GLUTAMIC ACID DECARBOXYLASE ASSOCIATED AUTOIMMUNE DISORDERS

This is a division of application Ser. No. 08/485,725 filed Jun. 7, 1995, which is a continuation-in-part of Ser. No. 07/716,909 filed Jun. 18, 1991, now abandoned, which is a continuation-in-part of Ser. No. 07/586,536 filed Sep. 21, 1990, now abandoned.

The present invention was supported by Grant NS22256 from the National Institutes of Health. The United States Government has certain rights in this invention.

BACKGROUND OF THE INVENTION

1. Field of the Invention

The present invention relates to glutamic acid decarboxylase$_{65}$ (GAD$_{65}$) polypeptides and methods of using GAD$_{65}$ polypeptides diagnostically and therapeutically in autoimmune disease.

2. Description of the Background Art

Insulin-dependent diabetes mellitus (IDDM; type I diabetes) is one of the most common metabolic disorders. In the United States, IDDM affects approximately one in 300 to 400 people, and epidemiological studies suggest that its incidence is increasing. The disease results from the autoimmune destruction of the insulin-producing β-cells of the pancreas. More specifically, the preonset stage is characterized by "insulitis", in which lymphocytes infiltrate the pancreatic islets and selectively destroy the β-cells. Insulitis may be present for many years before the onset of clinical symptoms. The typical IDDM presentation of hyperglycemia appears only after at least 80% of the insulin-producing β-cells are lost. The remaining β-cells are destroyed during the next few years.

Although insulin therapy allows most IDDM patients to lead normal lives, this replacement is imperfect and does not completely restore metabolic homeostasis. Thus, severe complications which result in dysfunctions of the eye, kidney, heart, and other organs are common in IDDM patients undergoing insulin therapy. Because of this, it is highly desirable to extend the latency period and prevent progression (e.g., through administration of immunosuppressant drugs to interfere with the autoimmune process and insulin to achieve better control of the effects of sustained hypoglycemia) between the start of β-cell destruction and the actual requirement of insulin replacement (i.e., when 80% of the β-cells are destroyed). Therefore, a diagnostic test which determines the beginning of β-cell destruction would allow the clinician to administer immunosuppressant drugs (Silverstein, et al., *New England Journal of Medicine*, 319:599–604, 1988) or prophylactic insulin therapy (Keller, et al., *Lancet*, 341:927, 1993) to extend this latency period and thus significantly delay the onset of insulin replacement side effects.

Many IDDM patients have sera which contain antibodies to a 64 kD molecule (Baekkeskov, et al., *J.Clin.Invest.*, 79:926–934, 1987; Atkinson, et al., *Lancet*, 335:1357–1360, 1990), to islet cell cytoplasmic (ICA) molecules or islet cell surface (ICSA) molecules (Bottazzo, et al, *Lancet*, 1:668–672, 1980), or to insulin (Palmer, et al., *Science*, 222:1137–1139, 1983; Atkinson, et al., *Diabetes*, 35:894–898, 1986). Atkinson and coworkers (Atkinson, et al., *Lancet*, 335:1357–1360, 1990) have demonstrated that the presence of antibodies to the 64 kD molecule in human sera appears to be the earliest and most reliable indicator that onset of IDDM symptoms will eventually occur.

Recently, Baekkeskov and coworkers established that the 64 kD molecule and glutamic acid decarboxylase (GAD) have several antigenic epitopes in common and thus they may be identical or very similar molecules. Although this identification is an important finding, the use of this information as a diagnostic tool for predicting IDDM is quite cumbersome and limited unless knowledge of the molecular biology of GAD is known. Studies by Kaufman, et al., (*J. Clin. Invest.*, 8:283, 1992) established that the 64 kD molecule was intact GAD$_{65}$. Consequently, the cloning and subsequent production of large quantities of GAD$_{65}$ or a GAD molecule which is antigenically substantially identical to the GAD$_{65}$ molecule or fragments of the GAD$_{65}$ molecule, both of which can be easily purified, will allow the development of a diagnostic kit designed to predict IDDM as well as effective therapeutic modalities. The present invention provides a means for accomplishing these results.

SUMMARY OF THE INVENTION

The present invention arose out of the discovery that recombinant DNA technology could be used to produce eukaryotic GAD$_{65}$ polypeptide and that GAD$_{65}$ polypeptide could be used in the diagnosis and therapy of patients with autoimmune disease. Particularly relevant is the use of eukaryotic GAD$_{65}$ polypeptide in the diagnosis and therapy of patients having, or at risk of having, GAD-associated autoimmune disorders such as insulin-dependent diabetes mellitus (IDDM) or stiff man disease.

A major advantage of the present invention is that it provides the art with a ready source of eukaryotic GAD$_{65}$ polypeptide corresponding to that purified from natural sources, while avoiding the problems associated with the isolation of naturally occurring eukaryotic GAD$_{65}$ polypeptide when separating it from other eukaryotic non-GAD$_{65}$ polypeptides. This absence of other eukaryotic non-GAD$_{65}$ polypeptides is significant in that it allows the development of test systems which will only detect antibodies specifically reactive with GAD$_{65}$ polypeptides.

Another advantage of providing eukaryotic GAD$_{65}$ polypeptide in host cells is that by so doing, it is possible to obtain much larger quantities of the polypeptide than are currently practicably available from natural sources. As a consequence, not only is it possible to use the polypeptide of the invention to more accurately classify and treat patients with such autoimmune diseases as IDDM, but it is also now possible to provide commercially useful quantities of GAD polypeptide for use in diagnostic systems and pharmaceutical compositions.

DESCRIPTION OF THE DRAWINGS

FIG. 1 Cloning strategy for obtaining GAD$_{65}$ and GAD$_{67}$ specific cDNA probes.

FIG. 2 DNA sequence and corresponding amino acid sequence for rat GAD$_{65}$.

FIG. 3 DNA sequence and corresponding amino acid sequence for human GAD$_{65}$.

FIG. 4 Comparison of rat GAD$_{65}$ and human GAD$_{65}$ amino acid sequences.

FIG. 5 GAD$_{65}$ and GAD$_{67}$ cDNAs hybridize to different size RNAs.

FIG. 6 Southern blots hybridized with cDNA probes specific for GAD$_{65}$ and GAD$_{67}$.

FIG. 7 Immunological identification of GAD$_{65}$ and GAD$_{67}$.

FIG. 8 Proliferative T-cell responses of NOD mice to β cell antigens.

FIG. 9 Characterization of GAD specific T-cell response of NOD mice as primed Th1 cells by enhanced clonal size (a) and cell surface markers (b) and IFNγ secretion.

FIG. 10 Intramolecular spreading of T-cell autoimmunity within the GAD molecule.

FIG. 11 Delay of onset of IDDM following immunization with $GAD_{65}$.

DETAILED DESCRIPTION OF THE INVENTION

The present invention relates to the manipulation of genetic materials by recombinant DNA procedures which make possible the production of polypeptides possessing part or all of the primary structural conformation for one or more of the epitopes for binding autoantibodies to glutamic acid decarboxylase$_{65}$ ($GAD_{65}$) and for polypeptides that bind to MHC receptors to block T-cell recognition. These polypeptides are highly useful for the immunological detection of autoantibodies reactive with them, since such autoantibodies are pre-diagnostic and indicative of autoimmune diseases such as insulin dependent diabetes mellitus and "stiff man" syndrome. These polypeptides can also be used for purposes of screening drugs, such as those that alter GAD function, and for generation of polyclonal and monoclonal antibodies which, in turn, can be used diagnostically to detect $GAD_{65}$.

The development of specific DNA sequences encoding eukaryotic $GAD_{65}$ polypeptide for splicing into DNA vectors can be accomplished using a variety of techniques. For example, alternative methods which can be employed include (1) the isolation of a double stranded DNA sequence from the genomic DNA of the eukaryote; (2) the chemical manufacture of a DNA sequence to provide the necessary codons for the polypeptide of interest; and (3) the in vitro synthesis of a double stranded DNA sequence by reverse transcription of mRNA isolated from a eukaryotic donor cell. In the latter case, a double stranded DNA complement of mRNA is eventually formed which is generally referred to as CDNA.

The manufacture of DNA sequences is frequently the method of choice when the entire sequence of amino acid residues of the desired polypeptide product is known. When the entire sequence of amino acid residues of the desired polypeptide is not known, the direct manufacture of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double stranded DNA or RNA probe sequences duplicating a sequence putatively present in the target cDNA may be employed in DNA/DNA hybridization procedures which are carried out on cloned copies of the cDNA which have been denatured into a single stranded form (Jay, et al., *Nucleic Acid Research*, 11:2325, 1983).

Hybridization procedures are useful for the screening of recombinant clones by using labeled mixed synthetic oligonucleotide probes wherein each is potentially the complete complement of a specific DNA sequence in the hybridization sample which includes a heterogeneous mixture of denatured double stranded DNA. For such screening, hybridization is preferably performed on either single stranded DNA or denatured double stranded DNA. These procedures are particularly useful in the detection of cDNA clones derived from sources where an extremely low amount of mRNA sequences relating to the polypeptide of interest are present. In other words, by using stringent hybridization conditions directed toward avoidance of non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

In addition, a GAD cDNA library can be screened by injecting the various cDNAs into oocytes, allowing sufficient time for expression of the cDNA gene products to occur, and testing for the presence of the desired cDNA expression product, for example, by using antibody specific for $GAD_{65}$ polypeptide, by using functional assays for $GAD_{65}$ enzymatic activity, or by measuring the ability of the expression product to stimulate pathogenic T-cells.

Alternatively, a cDNA library can be screened indirectly for $GAD_{65}$ peptides having at least one epitope using antibodies to $GAD_{65}$ (Chang and Gottlieb, *J.Neurosci.*, 8:2123, 1988). Such antibodies can be either polyclonally or monoclonally derived and used to detect expression product indicative of the presence of $GAD_{65}$ cDNA. Preferred are antibodies directed to an epitope found in the first 100 amino acids of the N-terminal portion of $GAD_{65}$.

Of the three above-noted methods for developing specific DNA sequences for use in recombinant procedures, the use of genomic DNA isolates, is the least common. This is especially true when it is desirable to obtain the microbial expression of mammalian polypeptides because of the presence of introns.

The present invention provides novel polypeptides of $GAD_{65}$ which have part or all of the primary structural conformation, that is, a continuous sequence of amino acid residues, having at least one epitope for antibodies to $GAD_{65}$ or at least one determinant for T-cell recognition. It is possible to use the polypeptide fragments of the invention rather than intact GAD to detect autoantibodies to GAD. The term "polypeptide," as applied to GAD polypeptide, includes any sequence of amino acids having an epitope for autoantibodies to GAD or binds to a T-cell MHC receptor.

Thus, the polypeptide fragments of GAD encompassed by the invention possess a biological activity such as the ability to induce and/or bind autoantibodies to GAD, bind to T-cell MHC receptors (especially receptors on pathogenic T-cells) and the like.

The polypeptides resulting from microbial expression of the DNA sequences of the invention or from other synthetic techniques, such as solid-phase peptide synthesis, can be further characterized by their freedom from association with other eukaryotic polypeptides or other contaminants which might otherwise be associated with GAD in its natural cellular environment or in such extracellular fluids as plasma or urine.

Studies by the present inventors unequivocally establish that $GAD_{67}$ and $GAD_{67}$ are encoded by distinct genes and are not produced, for example, by post-transcriptional or post-translational modification of a common genomic sequence. Evidence proving that $GAD_{65}$ and $GAD_{65}$ are encoded by different genes include: (a) the largest contiguous sequence of exact identity between $GAD_{65}$ and $GAD_{67}$ cDNAs is only 17 nucleotides in length, (b) cDNAs from $GAD_{65}$ and $GAD_{67}$ do not cross hybridize with each other's or with each other's mRNA under low stringency conditions (2.0×SSC, 0.01% SDS, 23° C.), and (c) $GAD_{65}$ and $GAD_{67}$ cDNAs do not cross hybridize with isolated genomic clones encoding $GAD_{67}$ and $GAD_{65}$, respectively.

The term "host" includes not only prokaryotes, but also such eukaryotes as yeast, filamentous fungi, plant and animal cells, as well as insect cells which can replicate and express an intron-free DNA sequence of eukaryotic $GAD_{65}$. However, prokaryotes are preferred as the host organism for screening purposes while eukaryotic cells, especially insect cells, are preferred for expression.

The term "prokaryotes" includes all bacteria which can be transformed or transfected with the gene for the expression of $GAD_{65}$. Prokaryotic hosts may include gram negative as well as gram positive bacteria such as, for example, *E. coli, S. typhimurium, Serratia marcescens* and *Bacillus subtilis*.

A recombinant DNA molecule coding for the $GAD_{65}$ polypeptides can be used to transform or transfect the host using any of the techniques commonly known to those of ordinary skill in the art. Especially preferred is the use of a plasmid or a virus containing the $GAD_{65}$ coding sequence for purposes of prokaryotic transformation or transfection, respectively. Alternatively, liposomes containing the DNA of interest can be used to obtain expression in the host (Zhu, et al., *Science*, 261:209, 1993)

Methods for preparing fused, operably linked genes and expressing them in bacteria are well-known in the art (Maniatis, et al., *Molecular Cloning: A Laboratory Manual*, Cold Spring Harbor Laboratory, Cold Spring Harbor, N.Y., 1989). The genetic constructs and methods described therein can be utilized for expression of $GAD_{65}$ in prokaryotic hosts.

In general, expression vectors containing promotor sequences which facilitate the efficient transcription of the inserted eukaryotic genetic sequence are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The polypeptides of the invention can then be isolated from the grown medium, cellular lysates, or cellular membrane fractions.

The isolation and purification of the expressed polypeptdes of the invention may be by any conventional means such as, for example, preparative chromatographic separations and immunological separations such as those involving the use of monoclonal or polyclonal antibody.

By having provided the sequence of amino acid residues of $GAD_{65}$, the present invention provides for the manufacture of DNA sequences which code for the host expression of polypeptide analogs or derivatives of $GAD_{65}$ which differ from naturally-occurring forms in terms of the identity or location of one or more amino acid residues and which share some or all of the epitopes of naturally-occurring polypeptide forms.

The novel DNA sequences of the invention include all sequences useful in providing the expression in prokaryotic or eukaryotic host cells of polypeptides which have at least a part of the primary structural conformation for one or more epitopes capable of reacting with autoantibodies to $GAD_{65}$ which are comprehended by: (a) the DNA sequence as set forth in FIGS. 2 or 3 or their complementary strands; (b) DNA sequences which hybridize to DNA sequences defined in (a) or fragments thereof; and (c) DNA sequences which, but for the degeneracy of the genetic code, would hybridize to DNA sequences defined in (a) and (b) above. Specifically comprehended in (b) are genomic DNA sequences which encode allelic variant forms of $GAD_{65}$. Part (c) specifically comprehends the manufacture of DNA sequences which encode $GAD_{65}$, $GAD_{65}$ fragments, and $GAD_{65}$ analogs wherein the DNA sequences thereof may incorporate codons which facilitate translation of mRNA in non-vertebrate hosts.

Since the cDNA sequence of the invention encodes essentially the entire human or rat $GAD_{65}$ molecule, it is now a matter of routine to prepare, subclone, and express smaller polypeptide fragments of cDNA from this or a corresponding cDNA sequence which would encode as few as one epitope for autoantibodies to human or rat $GAD_{65}$. The presence of such an epitope on a cloned polypepude can then be confirmed using, for example, serum from a patient with autoantibodies to $GAD_{65}$. An example of such a smaller peptide is the first approximately 100 amino acids from the N-terminus of $GAD_{65}$ (shown in FIG. 3). This amino acid sequence is essentially absent from $GAD_{67}$. Other examples of specific peptides of the invention are shown in Table 7 as well as the approximate carboxy-terminal two-thirds of GAD from about amino acid 224 to about amino acid 585. Especially preferred in the carboxy-terminal two-thirds of GAD is the amino acid segment from about amino acid 224 to about amino acid 398.

The present invention further relates to monoclonal antibodies which are specific for the polypeptides of the invention as well as the diagnostic and therapeutic use of these monoclonal antibodies. This specificity enables the monoclonal antibody, and like monoclonal antibodies with like specificity, to be used to bind the polypeptide of the invention when the polypeptide, or amino acids comprising the polypeptide, are present in specimens or a host, such as a human.

Numerous techniques can be utilized to produce the monoclonal antibodies of the invention without resorting to undue experimentation. To a great extent, the products of such monoclonal antibodies is rendered routine because of the highly defined nature of the polypeptides of the invention. Thus, whether the polypeptides of the invention are used for immunization and/or screening, the very limited number of immunogenic determinants on the polypeptides greatly simplifies the identification of cell lines producing monoclonal antibodies of the invention, for example, by limiting the repertoire of clonal expression possible.

One very useful type of cell line for expression of the monoclonal antibodies of the invention is the hybridoma. The general method used for production of hybridomas producing monoclonal antibody is well known (Kohler and Milstein, *Nature*, 256:495, 1975). The resulting hybridomas were then screened for production of monoclonal antibodies capable of binding to the polypeptides of the invention.

The techniques of sensitization and/or immunization, cell fusion, ascites production, selection of mixed hybridomas, or subcloning of monoclonal hybridomas are generally well known in the art. Attention is directed to Koprowski, et at., U.S. Pat. No. 4,172,124, Koprowski, et al., U.S. Pat. No. 4,196,265, or Douillard, J. Y. and Hoffman, T., *Basic Facts about Hybddomas, in Compendium of Immunology*, Vol. II, L. Schwartz, ed. (1981), which are herein incorporated by reference. In general, the purified peptides can be modified to have a cystine attached at the C-terminus to permit unidirectional attachment of the synthetic peptide to an immunogenic protein through a connecting bridge, for example, maleimidobenzoylated (MB)-keyhole limpet hemocyanin (KLH). Other immunogenic conjugates can also be used, for example, albumin, and the like. The resulting structure may have several peptide structures linked to one molecule of protein.

Somatic cells derived from a host immunized against the synthetic peptides can be obtained by any suitable immunization technique. The host subject is immunized by administering the antigen, usually in the form of a protein conjugate, as indicated above, by any suitable method, preferably by injection, either intraperitoneally, intravenously, subcutaneously, or by intrafoot pad. Adjuvants may be included in the immunization protocol.

The initial immunization with the protein bound antigen can be followed by several booster injections given periodically at intervals of several weeks. The antibody contained in the plasma of each host can then be tested for its reactivity with the immunizing polypeptide of the invention. The host having the highest response is usually most desirable as the donor of the antibody secreting somatic cells used in the production of hybridomas. Alternatively, hyperimmunization can be effected by repeatedly injecting additional amounts of peptide-protein conjugate by intravenous and/or intraperitoneal route.

The isolation of hybridomas producing monoclonal antibodies of the invention can be accomplished using routine screening techniques which permit determination of the elementary reaction pattern of the monoclonal antibody of interest. Thus, if a monoclonal antibody being tested binds with a polypeltide of the invention, then the antibody being tested and the antibody produced by the hybridomas of the invention are equivalent.

Alternatively, since the invention teaches polypeptides or amino acid sequences which are specifically required for binding of the preferred monoclonal antibodies of the invention, it is now possible to use these peptides for purposes of immunization to produce hybridomas which, in turn, produce monoclonal antibodies specific for the polypeptide. This approach has the added advantage of decreasing the repertoire of monoclonal antibodies generated by limiting the number of antigenic determinants presented at immunization by the polypeptide. The monoclonal antibodies produced by this method can be screened for specificity using standard techniques, for example, by binding polypeptide to a microtiter plate and measuring binding of the monoclonal antibody by an ELISA assay.

It is also possible to determine, without undue experimentation, if a monoclonal antibody has the same specificity as a monoclonal antibody of the invention by ascertaining whether the former prevents the latter from binding the polypeptide of the invention. If the monoclonal antibody being tested competes with the monoclonal antibody of the invention, as shown by a decrease in binding by the monoclonal antibody of the invention, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the polypeptide of the invention with which it is normally reactive, and then add the monoclonal antibody being tested to determine if the monoclonal antibody being tested is inhibited in its ability to bind the antigen. If the monoclonal antibody being tested is inhibited then, in all likelihood, it has the same, or a closely related, epitopic specificity as the monoclonal antibody of the invention.

The $GAD_{65}$ of the invention is particularly suited for use in immunoassays in which it can be utilized in liquid phase or bound to a solid phase carrier. In addition, $GAD_{65}$ used in these assays can be detectably labeled in various ways.

Examples of immunoassays which can utilize the $GAD_{65}$ of the invention are competitive and non-competitive immunoassays in either a direct or indirect format. Examples of such immunoassays are the radioimmunoassay (RIA), the sandwich (immunometric assay) and the Western blot assay. Detection of antibodies which bind to the $GAD_{65}$ of the invention can be done utilizing immunoassays which run in either the forward, reverse, or simultaneous modes, including immunohistochemical assays on physiological samples. The concentration of $GAD_{65}$ which is used will vary depending on the type of immunoassay and nature of the detectable label which is used. However, regardless of the type of immunoassay which is used, the concentration of $GAD_{65}$ utilized can be readily determined by one of ordinary skill in the art using routine experimentation.

The GAD and GAD fragments of the invention can be bound to many different carriers and used to detect the presence of antibody specifically reactive with the polypeptide. Alternatively, the carrier-bound GAD and GAD fragments can be used therapeutically for extracorporeal absorption of autoimmune antibodies in patients having, or at risk of having, GAD-associated disorders. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding $GAD_{65}$, or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

Alternatively, the polypeptide of the invention which comprises the GAD enzymatic domain can be used to detect antibodies to GAD by measuring GAD enzymatic activity. For example, $GAD_{65}$ and a specimen suspected of having antibodies to $GAD_{65}$ can be incubated for a period of time and under conditions sufficient to allow binding to occur between $GAD_{65}$ and the antibodies. The reaction product is precipitated and then tested for GAD enzymatic activity.

For purposes of the invention, the antibody which binds to $GAD_{65}$ of the invention may be present in various biological fluids and tissues. Any sample containing a detectable amount of antibodies to $GAD_{65}$ can be used. Normally, a sample is a liquid such as urine, saliva, cerebrospinal fluid, blood, serum and the like, or a solid or semi-solid such as tissue, feces and the like.

The materials for use in the assay of the invention are ideally suited for the preparation of a kit. Such a kit may comprise a carrier means being compartmentalized to receive in close confinement one or more container means such as vials, tubes and the like, each of the container means comprising one of the separate elements to be used in the method. For example, one of the container means may comprise $GAD_{65}$ bound to a carrier. A second container may comprise soluble, detectably-labeled second antibody, in lyophilized form or in solution.

In addition, the carrier means may also contain a plurality of containers each of which comprises different, predetermined amounts of $GAD_{65}$. These latter containers can then be used to prepare a standard curve into which can be interpolated the results obtained from the sample containing the unknown amount of autoantibodies to $GAD_{65}$.

In using the kit all the user has to do is add, to a container, a premeasured amount of a sample containing a measurable, yet unknown amount of autoantibodies to $GAD_{65}$ to be detected, a premeasured amount of carrier-bound $GAD_{65}$ present in the first container, and a premeasured amount of the detectably labeled second antibody present in the second container. Alternatively, the non-detectably labeled $GAD_{65}$ can be provided attached to the container to which the sample and the detectably labeled second antibody are added. After an appropriate time for incubation, an immune complex is formed and is separated from the supematant fluid, and the immune complex or the supematant fluid are detected, as by radioactive counting or addition of an enzyme substrate, and color development.

In an alternative embodiment, a kit comprising the GAD polypeptide of the invention can be used to detect the stage of GAD-associated autoimmune disease in a patient. As further shown herein, Applicants have discovered that certain GAD peptides or fragments are associated with different levels of progression in the autoimmune disease and that the level of disease process can be ascertained by looking at immune cell proliferative response, such as that of the pathogenic T-cell of the patient.

The term "ameliorate" denotes a lessening of the detrimental effect of the autoimmune response in the patient receiving therapy. The term "therapeutically effective" means that the amount of $GAD_{65}$ polypeptide used is of sufficient quantity to ameliorate the cause of disease due to the autoimmune response.

The $GAD_{65}$ polypeptides, including whole $GAD_{65}$, of the invention can be used therapeutically in patients having, or at risk of having, an autoimmune response associated with $GAD_{65}$. Such therapy can be accomplished, for example, by the administration of $GAD_{65}$ polypeptide to induce tolerance to GAD. Such administration can utilize unlabeled as well as labeled $GAD_{65}$ polypeptide. When unlabeled $GAD_{65}$ polypeptide is utilized advantageously, it would be in a form wherein, for example, the $GAD_{65}$ polypeptides are in fragments which are too small to stimulate an immune response, but large enough to bind, or block, the continuance of the autoimmune response. For example, $GAD_{65}$ could be digested enzymatically into epitope-sized peptides (typically 5–12 amino acids in length) and thereby bind to Fab binding portions present in the body fluids, or on the surface of immune cells, of the patient with autoimmune disease. Alternatively, peptides having at least one determinant for binding to T-cell MHC receptor can be similarly produced or chemically synthesized.

Alternatively, the $GAD_{65}$ polypeptides of the invention can be administered labeled with a therapeutic agent. These agents can be coupled either directly or indirectly to the $GAD_{65}$ polypeptides of the invention. One example of indirect coupling is by use of a spacer moiety. These spacer moieties, in turn, can be either insoluble or soluble (Diener, et al., *Science*, 231:148, 1986) and can be selected to enable drug release from the $GAD_{65}$ polypeptide at the target site. Examples of therapeutic agents which can be coupled to the $GAD_{65}$ polypeptides of the invention for immunotherapy are drugs, radioisotopes, lectins, and toxins.

The drugs with which can be conjugated to the $GAD_{65}$ polypeptides of the invention include compounds which are classically referred to as drugs such as mitomycin C, daunorubicin, and vinblastine.

In using radioisotopically conjugated $GAD_{65}$ polypeptides of the invention for immunotherapy, certain isotopes may be more preferable than others depending on such factors as leukocyte distribution as well as stability and emission. Depending on the autoimmune response, some emitters may be preferable to others. In general, $\alpha$ and $\beta$ particle-emitting radioisotopes are preferred in immunotherapy. Preferred are short range, high energy $\alpha$ emitters such as $^{212}Bi$. Examples of radioisotopes which can be bound to the $GAD_{65}$ polypeptides of the invention for therapeutic purposes are $^{125}I$, $^{131}I$, $^{90}Y$, $^{67}Cu$, $^{212}Bi$, $^{211}At$, $^{212}Pb$, $^{47}Sc$, $^{109}Pd$ and $^{188}Re$.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is accomplished by binding the $\alpha$-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by *Corynebacterium diphtheria* which can be used therapeutically. This toxin consists of an $\alpha$ and $\beta$ subunit which under proper conditions can be separated. The toxic A component can be bound to $GAD_{65}$ polypeptide and used for site specific delivery to a leukocyte expressing a receptor for $GAD_{65}$ polypeptide.

Other therapeutic agents which can be coupled to the $GAD_{65}$ polypeptides of the invention, as well as ex vivo and in vivo therapeutic protocols, are known, or can be easily ascertained, by those of ordinary skill in the art.

The present invention also relates to a polypeptide which can be administered therapeutically to ameliorate, or utilized diagnostically to identify, the disease process in patients having, or at risk of having, this disease. The conventional single-letter code used to represent the various amino acids relates as follows:

TABLE 1

| Phe: F | Leu: L | Ile: I | Met: M |
|--------|--------|--------|--------|
| Val: V | Ser: S | Pro: P | Thr: T |
| Ala: A | Tyr: Y | His: H | Gln: Q |
| Asn: N | Lys: K | Asp: D | Glu: E |
| Cys: C | Trp: W | Arg: R | Gly: G |

A polypeptide sequence of the invention was identified by comparing the amino acid sequences of human $GAD_{65}$, human $GAD_{67}$, and the P2-C protein of the picornavirus, coxsackie virus. The P2-C polynucleotide plays a role in the virus membrane bound replication complex. These analyses established the presence of an extensive sequence similarity between both $GAD_{65}$ molecules and the coxsackie virus. A core polypeptide of six contiguous amino acid residues of the $GAD_{65}$ and P2-C polypeptide are identical in amino acid sequence. Indeed, of the 24 amino acids in the polypeptide, 19 are identical or conserved. In addition, there also exists a high charge density and the presence of a proline residue which would render this region highly antigenic (see Table 2).

TABLE 2

COMPARISON OF AMINO ACID SEQUENCES

| Protein | | Amino Acid Sequence |
|---|---|---|
| Human GAD$_{67}$ | SEQ ID NO:01 | $_{258}$S I M A A R Y K Y F P E V K T K G M A A V P K L$_{281}$ |
| Human GAD$_{65}$ | SEQ ID NO:02 | $_{250}$A M M I A R F K M F P E V K E K G M A A L P R L$_{273}$ |
| Coxsackie Virus P2-C | SEQ ID NO:03 | $_{28}$F I E W L K V K I L P E V K E K H E F — L S R L$_{50}$ |

The solid line encloses identical amino acids whereas the dashed line encloses amino acid residues with similar charge, polarity, or hydrophobicity.

In Table 2, the solid line encloses identical amino acids whereas the dashed line encloses amino acid residues with similar charge, polarity, or hydrophobicity.

The discovery of this common polypeptide region supports an etiologic role for "molecular mimicry" in the precipitation of diabetes. Thus, where a patient genetically susceptible to IDDM is infected by a coxsackie virus, the immune response to the similar GAD sequence in the patient's β-cells. The immunological response is maintained by the antigenically similar GAD polypeptides resulting in the eventual destruction of the β-cells and the subsequent presentation of IDDM.

At present, it is believed that the destruction of pancreatic β-cells in IDDM is mediated by a cellular autoimmune response. As described herein, a polypeptide of the invention can ameliorate the autoimmune response to GAD. Because of the complexity of autoimmune disease, it is possible to is envision numerous possible therapeutic modalities which would allow the polypeptides of the invention to be used to ameliorate such diseases. In one embodiment, it appears that the polypeptides of the invention can be utilized to block recognition by a specific T cell receptor (TCR) or an MHC receptor presenting an autoimmune antigen on the surface of an antigen presenting cell (APC). The inhibition of such recognition might occur, for example, by providing the patient with the polypeptide of the invention which, in turn, can displace the autoimmune antigen being presented in the antigen-cleft of the MHC receptor. However, although not wanting to be bound to a particular theory, it is believed that the polypeptides of the invention probably act to induce or restore a tolerogenic state by direct interaction with the appropriate TCR on the surface of a GAD specific pathogenic T-cell. This latter therapeutic approach of direct interaction with the TCR is supported by the examples and suggests that suppression of the autoimmune response can be achieved through induction of high-zone tolerance by use of high concentrations of polypeptide, preferably soluble. Another possible mechanism is that the polypeptide of the invention may play a role in anergizing pathogenic T cells by binding to the T cell MHC receptor, thereby preventing the appropriate costimulatory signal.

Alternatively, the polypeptides of the invention could be used to stimulate a T-suppressor cell population in order to restore self-recognition and, thereby, ameliorate the autoimmune disease. Stimulation of T-suppressor cell populations could be achieved, for example, by use of a bi-specific antibody having one variable region specific for an epitope present on the autoimmune antigen residing in the cleft of the MHCII receptor and, a second variable region specific for an epitope present on the CD8$^+$ receptor. The production of antibody specific for the polypeptide of the invention is a matter of routine to those of skill in the art, as is the preparation of bi-specific antibodies having specificity for 2 or more epitopes.

Polypeptide analogs of the present invention may be designed which will compete for recognition of self-antigens at the level of antigen presentation or induce anergy in T cells, due to a lack of a costimulatory signal. Since MHC molecules contain a single peptide binding site, it is possible to design polypeptides which will bind with high affinity to disease-associated MHC molecules, but will not activate disease-causing T-helper cells. Such polypeptides act as antagonists for self-antigen recognition. In the present invention, support for this mechanism is found in the examples, especially Example 7. Precedent for such an approach arises from observation that a mouse lysozyme polypeptide, itself non-immunogenic, can compete for MHC binding with an immunogenic polypeptide from hen-egg white lysozyme and thereby reduce T cell activation by that polypeptide (Adorini, et al., *Nature*, 334:623–625, 1988) as well as studies using T-cell receptor peptides to block formation of complex between T-cells, autoantigen and MHC (Howell, et al., *Science*, 246:668, 1989). Similarly, such a therapeutic approach for screening effective polypeptide analogs has been utilized in such autoimmune diseases as experimental autoimmune encephalomyelitis (EAE) (Wraith, et al., *Cell*, 59:248, 1989; Urban, et al., *Cell*, 59:257, 1989).

The single-letter symbols used to represent the amino acid residues in the polypeptides of the present invention are those symbols commonly used in the art. The peptides of the invention include not only the natural amino acid sequences, but also peptides which are analogs, chemical derivatives, or salts thereof. The term "analog" or "conservative variation" refers to any polypeptide having a substantially identical amino acid sequence to a polypeptide provided herein and in which one or more amino acids have been substituted with chemically similar amino acids. For example, one polar amino acid, such as glycine or serine, may be substituted for another polar amino acid; or one acidic amino acid, such as aspartic acid may be substituted for another acidic amino acid, such as glutamic acid; or a basic amino acid, such as lysine, arginine, or histidine may be substituted for another basic amino acid; or a non-polar amino acid such as alanine, leucine, or isoleucine may be substituted for another non-polar amino acid.

The term "analog" or "conservative variation" also means any polypeptide which has one or more amino acids deleted from or added to a polypeptide of the present invention, but which still retains a substantial amino acid sequence homology to such peptide. A substantial sequence homology is any homology greater than 70%, preferably at least about 80%, and more preferably at least about 90%. The term "fragment" also means any shorter version of the polypeptides identified herein having at least 6 amino acid residues, wherein the fragment possesses biological activity, or is a fragment capable of inhibiting the stimulation of T-cells by a stimulating polypeptide fragment or substantially full-length molecule.

The term "chemical derivative" means any polypeptide derived from a polypeptide of the present invention and in which one or more amino acids have been chemically derivatized by reaction of the functional side groups of amino acid residues present in the polypeptide. Thus, a "chemical derivative" is a polypeptide that is derived from the sequences or polypeptides identified herein by one or more chemical steps. Such derivatized molecules include, for example, those molecules in which free amino groups have been derivatized to form amine hydrochlorides, P-toluene sulfoamides, benzoxycarboamides, T-butyloxycarboamides, thiourethane-type derivatives, trifluoroacetylamides, chloroacetamides, or formamides. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those polypeptides which contain one or more naturally occurring amino acids derivatives of the 20 standard amino acids. For example, 4-hydroxyproline may be substituted for proline; 5-hydroxylysine may be substituted for lysine; 3-methylhistidine may be substituted for histidine; homoserine may be substituted for serine, and ornithine may be substituted for lysine.

It should be understood that the present invention is not limited to the illustrative polypeptides depicted in Table 2 and Table 9, instead, a polypeptide falling within the scope of this invention may extend outside of, or comprise less than, the region between amino acid 28 and amino acid 50 of coxsackie virus P2-C, or between amino acid 250 and amino acid 273 of $GAD_{65}$, or between amino acid 258 and amino acid 281 of $GAD_{67}$, as well as the region between amino acid 78 and amino acid 97, or between amino acid 247 and amino acid 266, or between amino acid 335 and amino acid 356, or between amino acid 479 and amino acid 498, or between amino acid 509 and amino acid 528, or between amino acid 524 and amino acid 543, or between amino acid 539 and amino acid 556, or between amino acid 564 and amino acid 583 of $GAD_{65}$, as long as a substantial part of a given polypeptide is characterized by an amino acid sequence from that region, or segments or combinations thereof, and the polypeptide demonstrates the desired immunological or biological activity against autoimmune disease. In addition, polypeptides according to this invention include those having amino acid sequences which are longer or shorter in length than those of the polypeptides illustrated in Table 2 and Table 9, or which comprise segments or combinations thereof, as long as such polypeptides consist substantially of the region between the amino acids illustrated in Table 2 and Table 9 and demonstrate immunological or biological activity. All polypeptides of the invention should not stimulate or enhance the autoimmune disease.

Accordingly, it should be understood that the specific selection of any one polypeptide within the polypeptides of the invention does not involve undue experimentation. Such a selection may be carried out by taking a number of polypeptides and testing them for their immunological and biological activity in ameliorating the autoimmune disease or for detecting antibody. The NOD mouse represents an excellent and well characterized model for screening polypeptides of the invention capable of ameliorating or preventing diabetes. Example 7 illustrates an acceptable procedure for routine screening of candidate polypeptides with biologic activity.

The polypeptides according to the present invention may be prepared by recombinant techniques or by conventional synthesis using known polypeptide synthetic methods, including synthesis on a solid support. An example of a suitable solid phase synthetic technique is that described by Merriweather (*J.Am.Chem.Soc.*, 85:2149, 1963). Other polypeptide synthetic techniques may be found, for example, in Bodanszky, et al., *Peptide Synthesis*, John Wiley & Sons, 2d ed., 1976, as well as other references known to those skilled in the art. A summary of polypeptide synthesis techniques can be found in Stewart, et al., *Solid Phase Peptide Synthesis*, Pierce Chemical Company, Inc., Rockford, Ill., 1984. The synthesis of polypeptides by solution methods may also be used, for example, as described in *The Proteins*, Vol. II, 3d ed., Neurath, et al., eds., 105, Academic Press, New York, N.Y., 1976. Appropriate protective groups for use in such synthesis can be found in the above references as well as in J. McOmie, *Protective Groups in Organic Chemistry*, Plenum Press, New York, N.Y., 1973.

The polypeptides of the invention may also be prepared in an appropriate host transformed with DNA sequences that code for the desired polypeptide. For example, a polypeptide may be prepared by the fermentation of appropriate hosts that have been transformed with and which express a DNA sequence encoding the polypeptide. Alternatively, a DNA sequence encoding several of the polypeptides of this invention may be linked together and those sequences may then be used to transform an appropriate host to permit the expression of polypeptides involved in the autoimmune disease.

The dosage ranges for the administration of the GAD polypeptides of the invention are those large enough to produce the desired effect in which the symptoms or cellular destruction of the autoimmune response are ameliorated. The dosage should not be so large as to cause adverse side effects, such as unwanted cross-reactions, anaphylactic reactions, and the like. Generally, the dosage will vary with the age, condition, sex, and extent of the disease in the patient and can be determined by one of skill in the art. The dosage can be adjusted by the individual physician in the event of any counterindications. Dosage can vary from about 0.1 $mg/m^2$ to about 2000 $mg/m^2$, preferably about 0.1 $mg/m^2$ to about 500 $mg/m^2$/dose, in one or more dose administrations daily, for one or several days.

The GAD polypeptides of the invention can be administered parenterally by injection or by gradual perfusion over time. The GAD polypeptides of the invention can be administered intravenously, intraperitoneally, intramuscularly, subcutaneously, intracavity, transdermally, intranasally, or enterally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the $GAD_{65}$ polypeptides of the invention, the medicament being used for therapy of autoimmune response to $GAD_{65}$.

The above disclosure generally describes the present invention. A more complete understanding can be obtained by reference to the following specific examples which are provided herein for purposes of illustration only and are not intended to limit the scope of the invention.

EXAMPLE 1

CLONING AND EXPRESSION OF $GAD_{65}$

A. RECOMBINANT DNA PROCEDURES

In order to obtain cDNA probes specific for $GAD_{65}$ and $GAD_{67}$, total RNA was extracted from adult rat brain by guanidine isothiocyanate-cesium gradient using the method of Chirgwin, et al. (*Biochemistry*, 18:5294, 1979). Poly (A) RNA was purified on oligo dT cellulose, using the protocol by Bethesda Research Laboratories (BRL). First strand synthesis was performed by using MMLV-reverse transcrptase (BRL), with conditions suggested, except that poly $d(N_6)$-mers (Pharmacia) were used as primers. This cDNA-RNA mixture was heat inactivated at 65° C. for 15 min and stored at −20° C. For PCR, 1/50 of the sample was added to the 100 µl reaction. Degenerate oligonucleotides were synthesized (Applied Biosystems) to encode the underlined common amino acid sequences of feline (from cDNA) (Kobayashi, et al., *J.Neurosci.*, 7:2768, 1987) and rat (from peptides) (Chang and Gottlieb, *J.Neurosci.*, 8:2123, 1988) GAD (FIG. 1). The 5'-end sequence of each degenerate oligonucleotide contained one strand of the DNA sequence recognized by either SstI and HindIII (5' oligo) or SstI and SstII (3'-end oligo). These primers were used for selective amplification by polymerase chain reaction of the generated cDNA template as described by Gould, et al. (*Proc.Natl.Acad.Sci.,USA*, 86:1934, 1989). PCR products were subcloned into HindIII/SstI double digested Bluescript SK vector (Stratagene), transformed into DH5 (BRL), and plated by standard methods (Maniatis, et al., *Molecular Cloning: A Laboratory Manual*, Cold Spring Harbor Laboratory, Cold Spring Harbor, N.Y., 1989).

Colony hybridization was done with an 5'-$^{32}$P end labeled oligonucleotide specific to feline $GAD_{67}$ (Kobayashi, et al., *J.Neurosci.*, 7:2768, 1987). End labeling of oligonucleotide, hybridization conditions, and washing conditions were done as described (Wallace, et al., in *Guide to Molecular Cloning Techniques*; Berger, et al., Eds. in *Methods of Enzymology*; Abelson, et al., Eds. *Academic Press, Inc.*, San Diego, 432–442, 1987), except that the nitrocellulose filters were washed at 50° C. for 15 min. Colonies which were positive and negative in the hybridization were individually picked and grown overnight in Terrific Broth (Tartof, et al., Focus, 9:12, 1987). DNA was isolated using a boiling method (Maniatis, et al., *Molecular Cloning: A Laboratory Manual*, Cold Spring Harbor Laboratory, Cold Spring Harbor, N.Y., 1989) and templates were denatured by 0.2N NaOH and purified by Sephacryl S400 spun columns (Pharmacia). Sequencing of denatured double stranded template was by the chain-termination method (Sanger, et al., *Proc.Natl.Acad.Sci.,USA*, 74:5463, 1977) using the T7-sequencing kit (Pharmacia).

As shown in FIG. 1, PCR-generated rat $GAD_{65}$ and $GAD_{67}$ cDNAs were used as probes to screen a lambda ZAP (Stratagene) rat hippocampus library provided by S. Heinemann (Salk Institute) by standard techniques (Maniatis, et al., *Molecular Cloning: A Laboratory Manual*, Cold Spring Harbor Laboratory, Cold Spring Harbor, N.Y., 1989). A 2400 nucleotide $GAD_{65}$ cDNA (the largest clone) was isolated and subcloned by "zapping" as described by Stratagene. When a rat $GAD_{67}$ cDNA was obtained which was smaller than a 3.2 kb rat $GAD_{67}$ cDNA clone already on hand, the larger cDNA was sequenced. Exo III deletions (Henikoff, Gene, 28:351, 1984) were made in both directions for $GAD_{65}$ and $GAD_{67}$ and templates were prepared and sequenced as described above. Anchored PCR (Frohman, et al., *Proc.Natl.Acad.Sci.,USA*, 85:8998, 1988) was done to clone the remaining 5'-ends of $GAD_{65}$ and $GAD_{67}$ mRNAs which were not represented in the original cDNA clones isolated in the library screening. Sequencing of these clones revealed that neither $GAD_{65}$ nor $GAD_{67}$ mRNAs contained any further initiation codons (AUGs) in frame with the previously designated initiation codons of the original cDNA clones.

EXAMPLE 2

CHARACTERIZATION OF CLONED $GAD_{65}$

A. NORTHERN BLOT HYBRIDIZATION

Two PCR-derived cDNA probes were hybridized to Northern blots containing rat brain RNA in order to determine whether the $GAD_{67}$ and $GAD_{65}$ cDNAs were derived from two different mRNAs. RNA was extracted as described in Example 1. Poly (A) RNA was separated by electrophoresis in formaldehyde and transferred onto Biotrans (ICN) membranes, and hybridization was performed as described by Well, et al. (*J.Neurosci.*, 16:311, 1986), except that 100 µl/ml of poly (A) was added. Probes were labeled to approximately $10^9$ dpm/µg by the oligolabeling procedure of Feinberg and Vogelstein (*Anal.Biochem.*, 132:6, 1983). Identical results were subsequently obtained with full-length clones of $GAD_{65}$ and $GAD_{67}$ cDNAs.

As shown in FIG. 5, lanes 1 and 2 contain 1 µg of poly (A) selected RNA extracted from rat cerebellum. Lane 1 was hybridized to a cDNA probe for the rat cognate of feline $GAD_{67}$ (Kobayashi, et al., *J.Neurosci.*, 7:2768, 1987) and lane 2 with a cDNA probe for the rat peptide sequence (which corresponds to $GAD_{65}$).

The cDNA probe for the rat peptide sequence hybridized to a 5.7 kb RNA, while the cDNA probe for the rat cognate of feline $GAD_{67}$ cDNA, hybridized to a 3.7 kb RNA. This demonstrates that $GAD_{65}$ and $GAD_{67}$ are not derived from the same mRNA.

B. GENOMIC HYBRIDIZATION OF $GAD_{67}$ AND $GAD_{65}$

In order to investigate the possibilty that $GAD_{67}$ and $GAD_{65}$ arise from separate genes, cDNAs of both $GAD_{67}$ and $GAD_{65}$ were hybridized to DNA blots containing genomic DNA.

For Southern blots, genomic DNA was extracted from rat liver as described (Kaiser, et al., in *DNA Cloning*, vol.I, A Practical Approach, D. M. Glover ed., IRL Press, Oxford, pp. 38–40, 1985). DNA (10 µg/sample) was digested to completion with EcoRI and HindIII using conditions recommended by the suppliers (BRL, Gaithersburg, Md.). DNA fragments were separated by electrophoresis at 1.5 v/cm for 16 hrs in 0.8% agarose. The DNA was then transferred to Zeta-Probe membranes (Bio-Rad), hybridized, and washed, as described by Gatti, et al. (*Biotechniques*, 2:148, 1984), except that 5 µg/ml Carnation dried milk was substituted for Denhardt's solution. Probes for Southern blots were labeled as described in Example 1, above.

As shown in FIG. 6, genomic DNA digested with HindIII and EcoRI are in lanes 1 and 3 and lanes 2 and 4, respectively. $GAD_{67}$ cDNA was hybridized to lanes 1 and 2, whereas $GAD_{65}$ cDNA was hybridized to lanes 3 and 4. Numbers along the side of the gel are the DNA fragment sizes in kilobases.

This data shows that the two cDNAs hybridize to genomic fragments of different sizes. In addition, the greatest contiguous stretch of identical nucleotide sequence of $GAD_{65}$ and $GAD_{67}$ cDNAs is only 17 nucleotide bases in length. Thus, $GAD_{67}$ and $GAD_{65}$ are encoded by two distinct genes.

C. ENZYMATIC COMPARISON OF $GAD_{67}$ AND $GAD_{65}$

Studies were done comparing the effect of PLP on the activity of $GAD_{67}$ and $GAD_{65}$. In so doing, both cDNAs were subcloned into vectors that allowed their expression in bacteria (Studier, et al., *J.Mol.Biol.*, 189:113, 1986). Overexpression of "fusionless" $GAD_{65}$ and $GAD_{67}$ was accomplished by subcloning $GAD_{65}$ cDNA into the NcoI site of pET-8c and $GAD_{67}$ cDNA into the NheI site of pET-5c vectors (Studier, et al., *J.Mol.Biol.*, 189:113, 1986).

To obtain compatible sticky ends for correct in-frame subcloning of both cDNAs, selective amplification was performed by PCR using conditions suggested by United States Biochemical (USB), with 200 μM dNTPs and 1.5 mM $MgCl_2$ in the mixture and annealing at 55° C. with 20 cycles to decrease infidelity of AmpliTAQ (USB). Primers specific for $GAD_{65}$ and $GAD_{67}$ contained one DNA strand of the NcoI and SpeI recognition sites, respectively. Since there is a NheI restriction site within the coding region of $GAD_{67}$, SpeI (which is compatible with NheI) was used.

PCR products were subcloned into their respective pET vectors, transformed into DH5 and plated as described (Maniatis, et al., *Molecular Cloning: A Laboratory Manual*, Cold Spring Harbor Laboratory, Cold Spring Harbor, N.Y., 1989). Colonies were picked and grown overnight in LB broth with 50 μg/ml ampicillin. Subclones with correct orientation were transformed into BL21 (DE3) strain (Studier, et al., *J.Mol.Biol.*, 189:113, 1986) for overexpression. As a negative control, the pET-8C vector with no insert was transformed and subsequently induced. Single colonies were picked, grown, induced by 1 mM isopropyl-B-D-thiogalacto-pyranoside (IPTG), and analyzed on SDS-PAGE gels as described (Sambrook, et al., *Molecular Cloning a Laboratory Manual*, Cold Spring Harbor Laboratory Press, Cold Spring Harbor, 17.15–17.16, 1989).

To measure GAD activity, we induced 10 ml cultures of bacteria at $OD_{600}$-0.5 with 1 mM IPTG. Two hours after induction, bacteria was spun down and resuspended and sonicated in 1 ml of homogenizing buffer (1 mM phenylmethylsulfonyl fluoride (PMSF), 1 mM 2-aminoethylisothiouronium bromide (AET), and 60 mM potassium phosphate, pH 7.1). After sonication, cell debris was removed by centrifugation and protein concentration was measured (Bradford, *Anal.Biochem.*, 72:248, 1986) in the supernatant (supernatant was stored in aliquots at −70° C.). Brain homogenates were prepared as described (Legay, et al., *J.Neurochem.*, 46:1478, 1986). GAD activity was measured as described (Krieger, et al., *J.Neurochem.*, 33:299, 1984) with 0.2 mM PLP present or absent and 20 μl of brain homogenate or bacterial lysate in the incubation mixture. Production of $^{14}CO_2$ in bacterial lysates was linear with respect to time of incubation and protein concentration.

TABLE 3

| Source | GAD Specific Activity[a] | | Fold Increase in Induction |
|---|---|---|---|
| | −PLP | +PLP | |
| BL21(DE3) + pET-8c | 12 ± 0.4 | 9 ± 1 | — |
| BL21(DE3) + pET-$GAD_{65}$ | 115 ± 3 | 773 ± 61 | 6.7 |
| BL21(DE3) + pET-$GAD_{67}$ | 160 ± 2 | 389 ± 8 | 2.4 |
| Rat Brain | 131 ± 5 | 216 ± 2 | 1.6 |

[a]cpms of $^{14}CO_2$/μgprotein/hr of triplicates ± S.E.M.

As shown in Table 3, bacterial lysates containing $GAD_{65}$ or $GAD_{67}$ catalyze the conversion of [1-$^{14}$C]-glutamate to GABA and $^{14}CO_2$.

PLP stimulates the enzymatic activity of $GAD_{65}$ more than $GAD_{67}$. This greater stimulation probably reflects the faster cycling of $GAD_{65}$ through the inactivation cycle proposed by Martin and coworkers (Martin, *Cell.Mol.Neurobiol.*, 7:237, 1987). This faster cycling suggests that $GAD_{65}$ contributes more to the pool of apo-GAD that exists in vivo (Miller, et al., *Brain Res.Bull.*, 5(Suppl.2):89, 1980). Thus, in vivo, PLP appears to regulate $GAD_{65}$ activity more than $GAD_{67}$ activity.

$GAD_{65}$ activity in bacterial lysates is similar to the five-fold PLP stimulation of GAD activity found in synaptosomes prepared from rat substantia nigra (Miller, et al., *J.Neurochem.*, 33:533, 1979). Because both GADs are more dependent upon added PLP in bacteria than is the GAD activity in crude rat brain homogenates, the endogenous PLP concentration of bacteria lysates may be less than rat brain homogenates.

D. IMMUNOLOGICAL IDENTIFICATION OF $GAD_{65}$ AND $GAD_{67}$

Rat brain homogenates and bacterial lysates were extracted as described above. Equal volumes of loading buffer were added to each sample as described (Harlow, et al., *Antibodies, A Laboratory Manual*, Cold Spring Harbor Laboratory, Cold Spring Harbor, N.Y., 1988). Proteins were separated by electrophoresis in a 10% acrylamide gel in SDS and electrophoretically transferred to nitrocellulose (Harlow, et al., *Antibodies, A Laboratory Manual*, Cold Spring Harbor Laboratory, Cold Spring Harbor, N.Y., 1988). The unreacted sites were blocked with a phosphate buffered saline (PBS) solution containing 2% bovine serum albumin (fraction V), 1% gelatin, and 1% Triton-X-100 at 42° C. for one hr. After washing, the nitrocellulose filter was then cut into three sections and incubated with the following primary antibodies: lanes 1 to 4 with a 1/2000 dilution of the antiserum of Oertel, et al. (*Neuroscience*, 6:2689, 1981), which recognizes both $GAD_{67}$ and $GAD_{65}$; lanes 5–8 with a 1/2000 dilution of K-2 antiserum, which recognizes only $GAD_{67}$; lanes 9–12 with a 1/2000 dilution of GAD-6 monoclonal antibody, which is specific for $GAD_{65}$ (Chang, et al.,*J.Neurosci.*, 8:2123, 1988). All filters were extensively washed and appropriate secondary antibodies were incubated and washed. Bound antibodies were detected with $^{125}$I-labeled protein A and autoradiography. Each lane contained the following: lanes 1, 5, and 9 are BL21(DE3)+pET-$GAD_{67}$; lanes 2, 6, and 10 are BL21(DE3)+pET-$GAD_{65}$; lanes 3, 7, and 11 are rat brain homogenate; and lanes 4, 8, and 12 are BL21(DE3)+pET-8c.

The immunoblots of bacterially produced $GAD_{65}$ and $GAD_{67}$ demonstrated that $GAD_{65}$ indeed corresponds to the smaller GAD in brain extracts, and $GAD_{67}$ to the larger form (FIG. 7). Previous work has demonstrated the correspondence of $GAD_{67}$ to the larger GAD for feline $GAD_{67}$, and for mouse $GAD_{67}$ (Katarova, et al., *Eur.J.Neurosci.*, 2:190, 1990; 235, 1987). The mobilities of bacterially produced $GAD_{65}$ and $GAD_{67}$ (as detected with the antiserum of Oertel, et al. (*Neuroscience*, 6:2689, 1981) are identical to the immunoreactive doublet seen in rat brain homogenate.

The smaller molecular weight and larger molecular weight forms of GAD in rat brain are thus identical in antigenicity and size to the products of $GAD_{65}$ and $GAD_{67}$ cDNAs, respectively. Consequently, the two GADs in rat brain are $GAD_{65}$ and $GAD_{67}$. From these data it can also be concluded that the molecular identity of the reported PLP-dependent and PLP-independent GADs by Tapia (Bayon, et al., *J.Neurochem.*, 29:519, 1977) are $GAD_{65}$ and $GAD_{67}$, respectively. Martin and coworkers (Spink, et al., *Brain Res.*, 421:235, 1987) have reported the existence of four kinetically different forms of rat brain GAD. However, immunoblotting experiments (with the antisera used here) of these forms have not been reported.

E. DISTRIBUTION OF $GAD_{65}$ and $GAD_{67}$ IN RNAs IN BRAIN TISSUE

Experiments were done to determine the distribution of $GAD_{65}$ and $GAD_{67}$ in RNAs in cerebellum using in situ hybridization.

Transcripts of, respectively, 3.2 kb and 2.3 kb from $GAD_{65}$ and $GAD_{67}$ cDNAs, were radiolabeled with $^{35}S$ according to Wuenschell, et al. (*Proc.Natl.Acad.Sci., USA*, 83:6193, 1986) procedure. Hydrolyzed fragments of 200 bp were hybridized to coronal sections of a rat cerebellum. Animals were anesthetized under halothane and decapitated. The brain was rapidly frozen in dry ice and coronal frozen sections (12 μm) were fixed for 30 min in freshly prepared 4% formaldehyde in phosphate-buffered saline (PBS; 130 mM NaCl, 10 mM Na phosphate, pH 7.0). The tissue was dehydrated through graded ethanol solutions and stored at −70° C.

In order to increase tissue permeability, the sections were submitted to the following pretreatments: rehydration through graded ethanol solutions (5 min each in 95%, 85%, 70%, 50%, and 30% ethanol); PBS (5 min); 0.02N HCl (10 min); PBS (5 min); 0.01% Triton N-101 in PBS (1 min); PBS (2×5 min); 1 μg/ml proteinase K (7.5 min); and glycine (to inhibit proteinase K) in PBS (3×5 min). Proteinase K was digested for 30 min at 37° C. before use. Sections were then incubated at 37° C. in 50% formamide, 750 mM NaCl, 25 mM EDTA, 0.2% SDS, 0.02% BSA, 0.002% Ficoll, 0.02% polyvinylpyrrolidone, 250 μg/ml yeast tRNA, 250 μg/ml poly A, and 25 mM PPES (pH 6.8).

For the hybridization, 100 mM DTT, 10% dextran sulfate, and sense or antisense $^{35}S$-RNA were added to the prehybridization solution. An aliquot (50 μl) of the hybridization solution containing about 3 ng ($10^6$ cpm) of probe (sense or antisense) was added onto the slides. Each slide was coverslipped and incubated for 16 hrs at 50° C., following which the siliconized coverslips were removed by brief washing in 4×SSC (1×SSC–150 mM NaCl, 60 mM Na citrate, pH 7.0).

Sections were then treated with ribonuclease A (50 μg/ml in 0.5M NaCl, 10 mM Na thiosulfate, 1 mM EDTA, 10 mM TrisHCL, pH 8.0) for 20 min at 37° C. and rinsed for 2 hrs at room temperature in 2×SSC, 10 mM Na thiosulfate, for 30 min at 55° C. Sections were dehydrated in ethanol, delipidated in xylene, coated with Kodak NTB2 emulsion and exposed for 10 days at 4° C. The emulsion was developed with Kodak D19, and the tissue counterstained with cresyl violet.

Autoradiographic grains were detected using reflected polarized light and grain numbers, densities, nd cell areas were determined with an Analytic Imaging Concepts image analyzer system. Due to the low background level, the criteria for defining a cell "labeled" was based on the presence of more than 5 clustered grains. The GAD labeled cells were found scattered throughout the brain, enabling the measurement of the number of grains over individual cells. The boundary of the cell and the area covered by a grain allowed the calculation of the number of grains per cell. This analysis was done at a high magnification (800×), using both reflected polarized light and transmitted light to simultaneously visualize the stained cell and the superimposed grains. Numbers are means±S.E.M. of "n" cells.

TABLE 4

| CELL TYPE | GRAINS/CELL | | |
|---|---|---|---|
| | $GAD_{67}$mRNA | $GAD_{65}$mRNA | $GAD_{67}$:$GAD_{65}$ |
| Purkinje | 172 ± 34 (87)[a] | 43 ± 2 (70) | 4.0 |
| Golgi II | 96 ± 8 (80) | 64 ± 9 (65) | 1.5 |
| Basket | 61 ± 12 (102) | 16 ± 1 (57) | 3.8 |
| Stellate | 55 ± 15 (65) | 18 ± 3 (37) | 3.1 |

[a]±S.E.M(n)

In all neuronal types $GAD_{67}$ mRNA levels are greater. The observations with in-situ hybridization are consistent with previous findings (Nitsch, *J.Neurochem.*, 34:822, 1980; Denner, et al., *J.Neurochem.*, 44:957, 1985; Itoh, et al., *Neurochem. Res.* 6:1283, 1981) that the ratio of PLP dependent to independent GAD activities in the cerebellum is one of the lowest in brain regions tested. In addition, as shown in Table 3, the order of amounts for $GAD_{67}$ mRNA is Purkinje>Golgi II>Basket>Stellate cells; in contrast, for $GAD_{65}$ mRNA, this order is Golgi II>Purkinje>Basket>Stellate cells.

The expression of $GAD_{65}$ and $GAD_{67}$ mRNAs thus differs among classes of neurons. The contribution of each to total GAD activity in turn affects how GABA production is regulated. For example, the substantia nigra contains one of the highest ratios of PLP-dependent to PLP-independent GAD activities (Nitsch, *J. Neurochem.*, 34:822, 1980). Increasing GABA concentration in the substantia nigra by local injection of inhibitors of GABA catabolism is especially effective in reducing seizure susceptibility (Gale, *Fed. Proc.*, 44:2414, 1985). Experimental animals undergoing seizures induced by PLP-antagonists may therefore be unable to inhibit seizure propagation because of inhibition of $GAD_{65}$ particularly in nerve terminals within the substantia nigra.

F. SUBCELLULAR LOCATION OF $GAD_{65}$ AND $GAD_{67}$

The distribution of $GAD_{65}$ and $GAD_{67}$ was evaluated in the $S_2$ and synaptosome subcellular fractions. $S_2$ is a high speed supernatant consisting of the cytosol of all cells in the brain, while the synaptosomal fraction consists primarily of nerve endings (Gray, et al., *J. Anat., Lond*, 96:79, 1962). For these studies, whole rat brain fractionation was performed as described by Booth and Clark (Booth, et al., *Biochem. J.*, 176:365, 1978). Protein concentrations were determined by Schaffner and Weissman (Schaffner, et al., *Anal. Biochem.* 56:502, 1973). Samples were prepared as described (Kaiser, et al., *DNA Cloning*, Vol. I, *A Practical Approach*, D. M. Glover ed. (IRL Press, Oxford, 1985, pp. 38–40), and immunoblotting was done as described above using GAD-6 monoclonal antibody and K-2 antiserum. Equal amounts of protein (16 μg) were added to each lane. Autoradiography showed a linear response of increasing amount of $^{125}I$-protein A bound to antibody with protein concentrations of 1, 3, 10, 30, 100 μgs with both K-2 antiserum and GAD-6 monoclonal antibody (data not shown).

The results showed that $GAD_{67}$ was present in equal amounts in both fractions. Since the $S_2$ fraction contains the cytosolic proteins of glial (as well as other non-neuronal) and neuronal cells, the concentration of $GAD_{67}$ must be greater in neuronal cell bodies than in nerve endings. In contrast, the concentration of $GAD_{65}$ was greater in synaptosomes than in $S_2$. These subcellular fractionation experiments suggest that, in contrast to $GAD_{65}$, a much greater fraction of $GAD_{67}$ is present in cell bodies of neurons than in nerve terminals. Thus, subcellular fractionation, like immunohistochemistry, shows that $GAD_{65}$ and $GAD_{67}$ have different subcellular distributions.

In vivo experiments utilizing inhibitors of GABA synthesis and degradation have suggested that the GABA pool in neuronal cell bodies is different from that in the nerve terminals (ladarola, et al., *Mol. Cell. Biochem.*, 39:305, 1981). GABA produced by $GAD_{67}$ may be involved more in cellular metabolism (for example, in the GABA shunt) and in dendrodendritic synapses. The dendrites of granule cells in the olfactory bulb, which form dendrodendritic synapses with mitral dendrites (Shepard, *Physiol. Rev.*, 52:864, 1972) and probably release GABA (McLennan, *Brain Res.*, 29:177–184, 1971), label intensely with K-2 antiserum. While not shown here, it has also been found greater $GAD_{67}$ than $GAD_{65}$ mRNA levels (2–3 fold) in the olfactory bulb. This distribution is consistent with the reported finding that most GAD activity in the olfactory bulb is present in $S_2$ and $P_1$ (crude nuclear pellet) and not in synaptosomes (Quinn, et al., *J. Neurochem.*, 35:583, 1980).

The differing subcellular distributions of $GAD_{65}$ and $GAD_{67}$ could result from cytoskeletal anchoring or from some unknown protein targeting mechanism. Some cytoskeletal proteins have distributions that resemble $GAD_{65}$ and $GAD_{67}$. For example, in cultured sympathetic neurons Peng, et al. (*J Cel. Biol.*, 102:252, 1986), demonstrate that 84% of tau is in axons while 100% of MAP-2 is in cell bodies and dendrites. In addition, 43 kd protein, a cytoskeletal protein, is thought to anchor the acetylcholine receptor to the underlying membrane cytoskeleton (Flucher, et al., *Neuron*, 3:163, 1989).

EXAMPLE 3

DETECTION OF GAD AUTOANTIBODIES IN CLINICAL SPECIMENS

A. MATERIALS AND METHODS

1. Patient Specimens. Sera from four groups of individuals were selected from a previous study by Atkinson and co-workers (Atkinson, et al., *Lancet*, 335:1357–1360, 1990). These groups consisted of: Group (1), 1 new onset IDD patients diagnosed according to the established National Diabetes Data Group (NDDG) criteria (Gleichman, et al., *Diabetes*, 36:578–584, 1987) that had been referred to the University of Florida, Diabetes Clinics; Group (2), 5 randomly selected islet cell cytoplasmic antibody (ICA) negative non-diabetic controls without any known family history of autoimmune disease; Group (3), 13 individuals whose sera had been collected 3 to 66 months prior to their documented clinical onsets of IDD; Group (4), non-diabetic controls and relatives, and those who were studied prior to their onsets of IDD; and Group (5), 3 patients at risk for IDDM, but where onset has not yet occurred. This latter group had been ascertained through ongoing prospective ICA screening studies of more than 5000 first degree relative of IDD probands, and 8200 individuals from the general population (of which 4813 were school children).

2. Islet Cell Autoantibodies. ICA were assayed by indirect immunofluorescence on blood group O cryocut pancreatic (Atkinson, et al., *Lancet*, 335:1357–1360, 1990). All results were interpreted on coded samples, with control negative and positive sera in each batch. The degrees of ICA positivity were analyzed with the guidelines established by the Immunology Diabetes Workshop (IDW) for the standardization of ICA (Gleichman, et al., *Diabetes*, 36:578–584, 1987). All positive sera were titered by end point dilution, and the Juvenile Diabetes Foundation (JDF) units were determined by reference to a standard serum previously calibrated to the international JDF standard of 80 units. In the studies reported here, a positive ICA result was defined by replicate titers of 10 JDF units or greater.

3. HLA DR Typing. HLA DR typing was performed as adapted from the method described by Van Rood and Van Leuwen (*Nature*, 262:795–797, 1976), using DR trays (One Lamda Laboratories, Los Angeles, Calif.).

4. Human Islet Cells. Human pancreatic islets were isolated from cadaveric pancreases and maintained in vitro as previously described (Ricordi, et al., *Diabetes*, 37:413–420, 1988). The islet cells were metabolically labeled with $^{35}S$ methionine (Amersham, Arlington Heights, Ill.) in vitro (95% air/5% $CO_2$).

5. Islet Cell Extractions and Immunoprecipitations. Islet cells were extracted as previously described by Atkinson, et al. (*Lancet*, 335:1357–1360, 1990) with the following modifications. For immunoprecipitation studies, the islet cell lysates were precleared twice by incubation (2 h, 4° C.) with either control, IDD serum (100 μl), or GAD-6 (Chang, et al., *J.Neuro*, 8:2123–2130, 1988) (1 μl in 99 μl of Tris buffer (Atkinson, et al., *Lancet*, 335:1357–1360, 1990) for every 1000 islets. Immune complexes were then absorbed (1 h 4° C.) with an excess of protein A Sepharose CL-4B (Pharmacia, N.J.). Aliquot volumes representing 1000 islet cells containing unbound (precleared) lysate were then incubated (12 h, 4° C.) with either IDD or control sera (25 μl), or GAD-6 (Chang, et al., *J.Neuro*, 8:2123–2130, 1988) (1 μl in 25 μl Tris buffer). Following another incubation with protein A Sepharose CL-4B (1 h, 4° C.), the complexes were then washed 5 times with 50 mM Tris HCL (pH 7.4) with 0.1% SDS, 1.0% Triton X-114, and 2 mM EDTA, and then washed again one time in double distilled water. The protein A Sepharose CL-4B was then boiled in Laemmli sample buffer (Laemmli, *Nature*, 227:680–685, 1970), and the samples were subjected to SDS-PAGE and fluororadiography (Kodak, X-omat AR5) using Enhance (New England Nuclear). Alternatively, the autoradiographs were analyzed by a BETAGEN (Boston, Mass.) analyzer. Both 64 KA positive and negative sera were used in each assay, to serve as interassay controls. All fluororadiographs were analyzed and rated as positive or negative after comparison with the known interassay controls. Positive serum samples were designated as 1 when a sample resulted in immunoprecipitation of a low intensity 64,000 $M_r$ band, 2 if a moderate intensity band was observed and 3 if the intensity of the immunoprecipitated protein was high.

A similar rating procedure was employed for the intensity of bands corresponding to immunoprecipitated $^{35}S$-$GAD_{65}$ and $^{35}S$-$GAD_{67}$.

6. Immunoprecipitations. Immunoprecipitation of bacterial lysates containing $^{35}S$-$GAD_{65}$ or $^{35}S$-$GAD_{67}$, and GAD from human brain homogenate, was completed as described above in immunoprecipitation studies of human islet cell extractions.

7. GAD Assays. Human brain homogenates were incubated with patient sera as described above in human islet cells. After absorption and washes, the protein A agarose slurry was aliquoted into three equal volumes and GAD activity was measured as described (Krieger, et al., *Neurochem.* 33:299, 1984). Briefly, Protein A agarose beads were incubated with (1-$^{14}$C)-glutamate (Amersham) in a designated incubation mixture (Krieger, et al., *J. Neurochem.* 33:299, 1984) and production of $^{14}CO_2$ was quantitated by a liquid scintillation counter.

8. Production of $^{35}$S-GAD$_{65}$ and $^{35}$S-GAD$_{67}$. Rat GAD$_{65}$ and GAD$_{67}$ cDNAs were subcloned into a bacterial expression system as previously described. Labeling of $^{35}$S-GADs was completed by pulsing IPTG induced bacterium (growing in Minimal Media) for 15 minutes with TRAN $^{35}$S-label (ICN). Cultures were then spun down and resuspended and sonicated in 1 ml of homogenizing buffer (1 mM phenylmethylsulfonyl fluoride (PMSF), 1 mM 2-aminoethylisothiouronium Bromide (AET) and 60 mM potassium phosphate, pH 7.1). After sonication, cell debris was removed by centrifugation and protein concentration was measured (Bradford, *Anal.Biochem.*, 72:248, 1986) in the supernatant (supernatant was stored in aliquots at $-70°$ C.).

B. IMMUNOREACTIVITY OF IDDM SPECIMENS

Sera from patients with IDDM were tested for the ability to precipitate GAD from human brain homogenates.

TABLE 5

SERA FROM IDDM PATIENTS IMMUNOPRECIPITATE GAD ACTIVITY

| Patient | IDDM | Pre-IDDM Period[1] [1] | 64K[22] | JDF[33] | GAD Activity[4] [4] cpm's |
|---|---|---|---|---|---|
| DA | *[5] | >24 | 3 | 164 | 13,762 |
| DC | * | >1 | 3 | 20 | 1,719 |
| RS | + | 5 | 3 | 40 | 588 |
| NL | + | 0 | 2 | 80 | 440 |
| DM | * | >1 | 2 | 10 | 184 |
| C | — | na | 0 | 0 | 280 |
| C | — | na | 0 | 0 | 285 |
| C | — | na | 0 | 0 | 325 |
| C | — | na | 0 | 0 | 275 |
| C | — | na | 0 | 0 | 270 |

[1]Expressed as months
[2]64K titers as described in Experimental Methods
[3]The islet cell antibody test as expressd in Juvenile Diabetes Foundation (JDF) units
[4]Not adjusted for background
[5]At risk for diabetes (also, failed glucose test)
na — Not applicable As shown in Table 5, the sera of four (out of five) at risk for IDDM or IDDM patients bound significantly greater amounts of enzymatically active GAD of human brain extracts than sera from control patients. In addition, sera from one of the patients was drawn in a pre-IDDM period, thus autoantibodies to GAD are present prior to the onset of IDDM symptoms (see C below).

Further experiments (results not presented) showed that the sera of two at risk IDDM patients (DA, DC) immunoprecipitated recombinantly produced $^{35}$S-GAD$_{65}$ whereas recombinantly produced $^{35}$S-GAD$_{67}$ was only recognized by sera of patient DA (and to a lesser degree than $^{35}$S-GAD$_{65}$).

Additional studies using patient DA sera showed the presence of antibodies which recognize specific polypeptides produced in human pancreatic islet cells. Electrophoretic analysis of the bound polypeptides demonstrated the presence of autoantibodies to a 64 kD component, as previously shown by others in human IDDM (Baekkeskov, et al., *Nature*, 298:167–169, 1982) and in animal models (Baekkeskov, et al., *Science*, 224:1348–1350, 1984; Atkinson, et al, *Diabetes*, 37:1587–1590, 1988). Prior absorption of these sera with GAD-6 monoclonal, which recognized GAD$_{65}$ but not GAD$_{67}$, or with bacterially produced GAD$_{65}$, abolished the ability of the sera to recognize the 64 kD pancreatic polypeptide. The epitopes recognized by autoantibodies to the 64 kD autoantigen are thus present in GAD$_{65}$, indicating that the 64 kD autoantigen is indeed GAD$_{65}$. In order to investigate the predictive value of GAD$_{65}$, sera drawn from patients prior to onset of clinical manifestation of IDDM were tested for autoantibodies to GAD$_{65}$.

TABLE 6

IDDM PATIENTS ANALYZED FOR AUTOANTIBODIES PRIOR TO THE ONSET OF DISEASE

| Patient | Sex | HLA | Age Onset[1] [1] | Pre-IDD Period[2] [2] | JDF | 64KA[3] [3] | GAD[33]$_{65}$ | GAD[33]$_{67}$ |
|---|---|---|---|---|---|---|---|---|
| TA | M | 3,2 | 17 | 11 | 20 | 2 | 0 | 1 |
| CA | F | 4,5 | 38 | 4 | 0 | 1 | 1 | 0 |
| RA | M | 2,1 | 5 | 34 | 0 | 2 | 1 | 0 |
| TB | M | 2,4 | 11 | 66 | 40 | 1 | 1 | 0 |
| AB | M | N.D. | 23 | 6 | 160 | 3 | 3 | 2 |
| VC | F | 4,6 | 15 | 3 | 40 | 1 | 0 | 1 |
| JD | M | 6,1 | 34 | 25 | 10 | 3 | 1 | 1 |
| DR | F | 3,4 | 14 | 42 | 320 | 2 | 1 | 0 |
| JG | M | 3,3 | 12 | 8 | 40 | 1 | 0 | 0 |
| BR | M | 3,3 | 5 | 9 | 0 | 0 | 1 | 1 |
| KR | F | 4,X | 34 | 14 | 10 | 3 | 2 | 0 |
| JT | F | 4,6 | 7 | 10 | N.D. | 1 | 1 | 1 |

[1]Age of IDDM onset expressed as months
[2]The time interval between sera drawn and IDDM onset expressed as months
[3]1 = lowest; 2 = medium; and 3 = highest band intensities
N.D. — not determined As shown in Table 6, 9 out of 12 specimens (75%) were immunoreactive with $^{35}$S-GAD$_{65}$. In addition, two patients (JA and VC) were immunoreactive to GAD$_{67}$, but not GAD$_{65}$ under these conditions. Therefore, in combination, autoantibodies to GAD$_{65}$ and GAD$_{67}$ were present in 11 out of 12 (91%) of these patients sera. This finding suggests that although autoantibodies to GAD$_{65}$ are more common than autoantibodies to GAD$_{67}$, the use of both recombinant GADs (GAD$_{65}$ and GAD$_{67}$) in an assay would allow for greater predictability of IDDM. Previous tests of these sera (Atkinson, et al., Langet, 335:1357–1360, 1990) demonstrated that 11 out of 12, or 92%, immunoreacted With the $^{35}$S-64 kD molecule from human pancreatic islet cells. The serum which contained detectable autoantibodies to the 64 kD molecule and not GAD$_{65}$ was a serum which contained the lowest titer (or "1") for the 64 kD molecule. Thus, the false negative obtained was due to a lack of sensitivity in this assay. Furthermore, this assay predicted IDDM in one patient (BR) who was negative for 64K These results show that the 64 kD molecule identified in β-cells of human pancreas is identical in size and antigenicity to rat GAD$_{65}$. Furthermore, sera drawn from patients prior to IDDM onset contain autoantibodies to GAD$_{65}$. Consequently, the GAD$_{65}$ recombinant molecule is of great utility as a diagnostic tool for predicting IDDM. The ability of a physician to diagnose IDDM prior to actual symptoms may result in a greater extension of time before insulin therapy is needed. The sensitivity of such immunoassays will improve with the use of a recombinant GAD$_{65}$ of human origin which represents the GAD form present in β-cells of the pancreas.

EXAMPLE 4

IMMUNE PROLIFERATIVE RESPONSE TO POLYPEPTIDE

Polypepudes were synthesized using an automatic instrument (Applied Biosystems) and standard conditions. These polypeptides were then tested to compare their relative ability to stimulate proliferation of splenic lymphocytes and islet infiltrating T lymphocytes (IITLs). In this study, polypeptides derived from the GAD$_{65}$ core sequence and from the homologous region of polio virus were compared. Appropriate cells were cultured for 5 days with the respective polypeptde in the presence of 5×10$^4$ irradiated spleen cells. $^3$H-thymidine was added during the last 16 hours of culture.

tion may be due to a lower frequency of GAD polypeptide specific T cells.

The IITL population, when evaluated in the same manner, showed a marked difference in cell proliferation. In this system, the response to the GAD$_{65}$ polypeptide was 9-fold greater than that of either the culture media or the polio polypeptide. This data strongly suggests that the GAD$_{65}$ is an important antigen for T cell responses in the IITL population. This data suggests that molecular mimicry plays a role in the pathogenesis of diabetes.

EXAMPLE 5

GAD INDUCES PROLIFERATION OF SPLEEN CELLS OF NOD MICE

Proliferative T-cell responses to β-cell antigens (βCA) develop spontaneously in the nonobese diabetic (NOD) mouse model in a defined chronological order. The NOD mouse experimental model is considered the most analogous in vivo system available for studying IDDM in humans. This example describes studies on the antigen-induced blastogenesis of spleen cells from newborn to 5 month old female NOD mice when exposed to GAD and other peptides.

The βCAs tested included one of the two forms of GAD (Kaufman, et al., Science, 232:1138–1140, 1986; Erlander, et al., Neuron, 7:91–100, 1991; Kaufman, et al., Trends in Pharm. Sci. (in press)), (GAD$_{65}$, previously known as the 64K autoantigen (Baekkeskov, et al., Nature, 298: 167–169, 1981; Baekkeskov, et al., Nature, 347:151–156, 1990), carboxypeptidase H (CPH) (Castano, et al., J. Clin. Endoctrinol. Metab., 73:1197–1201, 1991), insulin (Palmer, Predicting IDDM, Diabetes Reviews, 1:104–115, 1993) and a peptide of hsp which has been shown to be the immunodominant determinant recognized by NOD T-cells (Elias, Proc. Natl. Acad. Sci., 88:3088–3091, 1991). GAD in particular, is a good candidate for the initial target antigen in IDDM since autoantibodies to GAD arise early in the natural history of the disease (Baekkeskov, supra; Atkinson, et al., Lancet, 335:1357–1360, 1990; Kaufman, et al., J. Clin. Invest., 89:283–292, 1992). Furthermore, unlike the ubiquitous hsp, GAD is expressed primarily in β-cells and the immunologically privileged central nervous system (CNS) and gonads. As control antigens, irrelevant prototype foreign and self antigens including hen eggwhite lysozyme (HEL), human serum albumin (HSA), E. coli. β-galactosidase (β-gal) and murine myelin basic protein (MBP) were used.

NOD (Taconic farms) and BALB/c mice (Jackson Laboratories) were kept under specific pathogen free con-

TABLE 7

| ANTIGEN | | | AMINO ACID SEQUENCE | $^3$THYMIDINE INCORPORATION (cpm) BY LYMPHOID CELL POPULATION | |
|---|---|---|---|---|---|
| | | | | IITLs[a] | SPLEEN[b] |
| None | | | — | 1,100 | 6,500 |
| Poliovirus | SEQ ID NO:04 | MKSMCPQAQLKVKYL | | 900 | 22,500 |
| GAD$_{65}$ | SEQ ID NO:05 | ARFKMFPEVKEKGMAA | | 9,500 | 23,300 |

[a] islet infiltrating T lymphocytes (3 × 10$^4$ cells/well)
[b] 1 × 10$^5$ cells/well In these studies, there was no significant difference in the proliferative activity of cultures of spleen lymphocytes exposed to either the polio or the GAD$_{65}$ polypeptides. However, both polypeptides stimulated a T cell response which was higher than that found in the media control. The lack of difference in proliferation in the spleen cell populaditions. The mice were sacrificed at the ages indicated and the spleen cells were tested directly ex vivo for their proliferative recall response to antigen. Single cell suspensions of spleen cells were plated at 1×10$^6$ cells per well in 96 well microtiter plates in 200 μl serum free HL-1 medium (Ventrex) that was supplemented with 2 mM glutamine with or without 10 μg/ml antigen (or 7 μM peptide) in triplicate cultures. During the last 16 h of the 72 h culture period, 1 μCi[³H]-thymidine was added per well. Incorporation of label was measured by liquid scintillation counting.

Both human $GAD_{65}$ (Bu, et al., *Proc. Natl. Acad. Sci.*, 89:2115–2119, 1992) and *E. coli* β-gal (control) were purified from recombinant bacteria on the basis of a hexahistidine tag which allows their rapid affinity purification by metal affinity chromatography (Hochuli, et al., *Bio/Technology*, 6:1321–1325, 1988). Bovine CPH was the generous gift of L. Fricker (Albert Einstein Col. Med.) and human insulin was purchased from Eli Lilly.

As illustrated in FIG. 8, while proliferative T-cell responses were not detected at any time point to the control antigens, a response to GAD arose at 4 weeks of age in NOD mice, concurrent with the onset of insulitis in the colony. The blastogenesis induced by GAD increased during the next four weeks and then declined to background levels by week 16. At 6 weeks of age, near the peak of anti-GAD reactivity, T-cell responses to hsp appeared and increased until week 15 and then diminished as well (FIG. 8). In all NOD mice tested, hsp reactivity was preceded by an anti-GAD response, suggesting that the former reactivity developed as a secondary event during the autoimmune process. Similarly, while no response was detected to CPH at 4 weeks of age, a strong anti-CPH response was observed by week 8. In some mice, a weak response to insulin was observed at 12 weeks, which became more prevalent at 15 weeks of age (FIG. 8 and Table 8). None of the antigens induced proliferation in T-cells from age-matched control BALB/c or (NOD×BALB/c) $F_1$ mice, both of which do not develop insulitis or IDDM. T-cell reactivity subsequently arises to other βCAs, consistent with the intermolecular diversification of the autoimmune response. Thus, the autoimmune response to GAD was the first to occur among the autoantigens tested. In view of this, tolerization to GAD should prevent the spread of autoimmunity to other βCAs and insulitis. If this were not the case then tolerization to GAD should have no effect on the response to these other antigens.

Blastogenesis provides an approximation of the relative clonal sizes of antigen-specific CD4+ T-cells (Corradin, et al., *J. Immunol.*, 119:1048–1053, 1977). The data in FIG. 8 shows that GAD reactive T-cells "spontaneously" undergo clonal expansion concurrent with the onset of insulitis. These findings are consistent with an endogenous priming event.

EXAMPLE 6

INDUCTION OF TOLERANCE WITH GAD

This example describes a study which shows that induced tolerance to GAD can ameliorate IDDM.

1. In these experiments female NOD mice were intravenously injected at 3 weeks of age with 50 μg GAD, μ-galactosidase, mycobacterial hsp65 (m-hsp) or 0.1 μg of the immunodominant hsp peptide (hsp-p), in PBS. At 12 weeks of age, mice were examined for insulitis and autoantigen reactive T-cells. At this age both indications are established in untreated NOD mice. Pancreatic tissue sections were stained by immunoperoxidase techniques for insulin and were counterstained with hematoxylin. Insulitis was scored in a blinded manner by examining 54 to 87 islets on 5 interrupted tissue sections from each pancreas. Proliferative splenic T-cell responses induced by various antigens were performed as described above in Example 4. Data in Table 8 are expressed as the average [³H]-thymidine label (cpm) incorporated in triplicate cultures.

TABLE 8A

GAD Induced Tolerance

Spleen Cell Proliferation (SI ± SEM)[b]

| | Insulitis | | | | GAD Peptides | | | hsp | |
|---|---|---|---|---|---|---|---|---|---|
| Treatment | Score[a] | N | β-Gal | GAD | #17 | #34 | #35 | Peptide | CPH |
| Uninjected | 2.4 ± 0.2 | 5 | 1.0 ± 0.2 | <u>9.5 ± 2.1</u> | <u>4.8 ± 0.4</u> | <u>6.0 ± 0.1</u> | <u>2.9 ± 0.2</u> | <u>6.7 ± 1.0</u> | ND[c] |
| β-Gal. | 2.6 ± 0.6 | 5 | 1.1 ± 0.1 | <u>15.4 ± 1.8</u> | <u>5.1 ± 0.6</u> | <u>5.1 ± 0.6</u> | <u>4.0 ± 0.2</u> | <u>6.6 ± 0.5</u> | <u>11.5 ± 0.9</u> |
| GAD | 0.1 ± 0.1 | 8 | 1.1 ± 0.03 | 1.6 ± 0.3 | 1.0 ± 0.05 | 1.2 ± 0.1 | 1.0 ± 0.1 | 1.2 ± 0.1 | 1.1 ± 0.02 |
| hsp-p | 1.7 ± 0.4 | 5 | 1.1 ± 0.05 | <u>5.8 ± 0.2</u> | <u>4.5 ± 0.1</u> | <u>4.1 ± 0.3</u> | <u>4.2 ± 0.1</u> | 1.1 ± 0.04 | <u>4.4 ± 0.2</u> |
| m-hsp | 1.8 ± 0.5 | 5 | 1.0 ± 0.1 | <u>4.2 ± 0.1</u> | <u>3.9 ± 0.1</u> | <u>3.9 ± 0.1</u> | <u>3.4 ± 0.2</u> | 1.0 ± 0.03 | <u>4.3 ± 0.2</u> |

[a]Severity of mononuclear cell infiltration was defined histologically(0 = nolymphocyticinfiltration; 1 = <25%; 2 = 25–50%; 3 = 50–75%; 4 = >75%)(Qin, et al., Immunol., 150:2072–2080, 1992). Score is mean ± SE.
[b]Significant responses noted by solid underline, border line responses noted by double underline.
[c]Not determined.

TABLE 8B

GAD Induced Tolerance

Spleen Cell Proliferation (SI ± SEM)[b]

| Treatment | Insulitis Score[a] | N | β-Gal | GAD | GAD Peptides #17 | #34 | #35 | hsp Peptide | CPH |
|---|---|---|---|---|---|---|---|---|---|
| 11 peptide | ≈2.5 | | 1.0 ± 0.1 | <u>21.1</u> ± 2.2 | <u>13.7</u> ± 1.5 | <u>11.4</u> ± 1.5 | <u>11.3</u> ± 0.7 | <u>13.3</u> ± 0.9 | ND |
| 34/35 peptides (+IFA) | 0.7 ± 0.4 | | 1.0 ± 0.2 | 1.9 ± 1.1 | 2.2 ± 1.2 | 1.1 ± 0.3 | 1.0 ± 0.1 | 1.8 ± 1.1 | ND |
| IFA alone (+IFA) | ≈2.5 | | 1.0 ± 0.1 | <u>8.1</u> ± 0.5 | <u>5.0</u> ± 0.5 | <u>4.8</u> ± 0.5 | <u>4.8</u> ± 0.4 | <u>6.6</u> ± 0.6 | ND |

[a]Severity of mononuclear cell infiltration was defined histologically(0 = nolymphocyticinfiltration; 1 = <25%; 2 = 25–50%; 3 = 50–75%; 4 => 75%)(Qin, et al., Immunol., 150:2072–2080, 1992). Score is mean ± SE.
[b]Significant responses noted by solid underline, border line responses noted by double underline.
[c]Not determined.

TABLE 8C

GAD Induced Tolerance

Spleen Cell Proliferation (SI ± SEM)[b]

| Treatment | Insulitis Score[a] | N | β-Gal | GAD | GAD Peptides #17 | #34 | #35 | hsp Peptide | CPH |
|---|---|---|---|---|---|---|---|---|---|
| 11 peptide | ≈(?) | | 1.4 ± 0.4 | <u>12.1</u> ± 3.5 | <u>6.9</u> ± 0.4 | <u>6.4</u> ± 1.0 | <u>6.8</u> ± 0.3 | <u>8.7</u> ± 0.9 | ND |
| HEL peptide | (?) | | 1.2 ± 0.2 | <u>10.7</u> ± 3.5 | <u>6.4</u> ± 1.4 | <u>5.9</u> ± 1.6 | <u>6.9</u> ± 1.9 | <u>8.0</u> ± 1.8 | ND |
| 34/35 peptides (+IFA) | (?) | | 1.0 ± 0.1 | <u>4.4</u> ± 2.6 | 1.8 ± 1.1 | 1.0 ± 0.1 | 1.1 ± 0.2 | 2.7 ± 1.3 | ND |

[a]Severity of mononuclear cell infiltration was defined histologically(0 = nolymphocyticinfiltration; 1 = <25%; 2 = 25–50%; 3 = 50–75%; 4 => 75%)(Qin, et al., Immunol., 150:2072–2080, 1992). Score is mean ± SE.
[b]Significant responses noted by solid underline, bordeline responses noted by double underline.
[c]Not determined.

Seventy five percent of the GAD treated mice, but none of the controls, showed no T-cell reactivity to GAD (indicating complete tolerization) or to other βCAs. These mice were also completely free of insulitis (score 0.0). If there were another effector T cell population in the islets, specific for an unknown βCA, that preceded the anti-GAD response, the release of cytokines by this population should have promoted T-cell responses to βCAs and insulitis (Sarvetnick, et al., Nature, 346:844, 1990; Heath, et al., Nature, 359:547, 1992). Twenty five percent of the GAD-treated mice were not completely tolerized to GAD, as evidenced by a weak residual GAD reactivity (SI of about 3) and displayed very limited peri-insulitis. In contrast, while tolerization to both of the hsp antigens was complete, these treatments reduced, but did not prevent, the development of T cell responses to other βCAs or insulitis. Thus, while the inactivation of GAD-reactive T cells prevented β cell autoimmunity, hsp tolerization only partially reduced it, as would be expected if a secondary element was removed from the amplifactory cascade.

In ongoing experiments examining the effects of GAD tolerization on diabetes incidence, all of the GAD treated mice (n=17, presently 37 weeks old) have normal glucose levels, while 70% of the mice receiving control antigens developed hyperglycemia by 19 weeks of age (n=20). Five GAD treated mice were sacrificed at 30 weeks of age. All were free of detectable βCA reactive T cells. Of these five animals, four mice were completely free of insulitis and one mouse displayed very limited peri-insulitis. These data show that inactivation of GAD reactive T-cells prevents the long term development of insulitis and diabetes.

2. In a second set of experiments neonatal female NOD mice were injected intraperitoneally IFA with peptide 11, a mixture of peptides 34 and 35 plus IFA, or with IFA alone and at 12 weeks of age the mice were examined for insulitis and autoantigen reactive T-cells as in Example 6.1. Proliferative splenic T-cell responses induced by the various antigens were performed as in Example 4, and data in Table 8B are expressed as the average [$^3$H]-thymidine label (cpm) incorporated in triplicate cultures.

The data in Table 8B show that tolerization with control peptide 11 did not prevent auto antibody response to GAD or to GAD peptides 17, 34 or 35. Nor was response to hsp peptide prevented by tolerization with peptide 11. IFA alone was somewhat effective at suppressing immune response. By contrast, tolerization with the mixture of peptides 34 and 35 suppressed the autoimmune response of spleen cell proliferation to all species tested: β-gal, GAD, GAD peptides 17, 34 and 35, and hsp peptide. In addition, tolerization to GAD peptides 34 and 35 greatly reduces insulitis but does not completely prevent it as whole GAD$_{65}$ does.

3. In a third set of experiments female NOD mice were intravenously injected at three weeks of age with peptide 11

(control), a mixture of peptides 34 and 35 plus IFA, or with HEL peptides and at 12 weeks of age the mice were examined for insulitis and autoantigen reactive T-cells as in Example 6.1. Proliferative splenic T-cell responses induced by the various antigens were performed as in Example 4, and data in Table 8C are expressed as the average [$^3$H]-thymidine label (cpm) incorporated in triplicate cultures.

The data in Table 8C show that tolerization with control peptide 11 did not prevent auto antibody response to GAD, to GAD peptides 17, 34 or 35 or to hsp although the response was not as great as in Example 6.2. Nor was response to hsp peptide prevented by immunization with peptide 11. By contrast, immunization with the mixture of peptides 34 and 35 plus IFA suppressed the autoimmune response of spleen cell proliferation to all species tested: β-gal, GAD, GAD peptides 17, 34 and 35, and hsp peptide.

EXAMPLE 7

CHARACTERIZATION OF GAD-REACTIVE T-CELLS

This example describes studies on GAD-Reactive T-Cells for additional properties that distinguish activated/memory from resting/naive lymphocytes.

In one series of experiments γ interferon (IFNγ) was measured by ELISA in culture supernatants (CSN) of spleen cells of 6–9 week old mice after challenge with GAD or control antigens HEL and MBP. Additionally, the frequency of antigen specific, IFNγ-producing cells was determined by an ELISA spot technique (T. Taguchi, et al., *J. Immunol.*, 145:68–77, 1990). Frequency of antigen-induced, spot forming cells (SFC) among $10^3$ spleen cells is represented in FIG. 9(*a*). Values are the mean+SEM from 5 individual female NOD mice, each tested in triplicate cultures with or without antigen. Results from a single experiment are shown. These are representative of 3 separate experiments.

In performing these experiments, freshly isolated spleen cells were cultured with or without antigen as described in Example 4. CSN were taken after 48 h and the concentration of IFNγ was determined by ELISA (Macy, et al., *FASEB J.*, 3003–3009, 1988). IFNγ specific monoclonal antibody (mAb) R4-6A2 (Pharmingen) was used as the capturing reagent and biotinylated mAb XMG 1.2 (Pharmingen, also specific for IFNγ) was used in conjunction with streptavidin-alkaline phosphatase (Zymed) and p-nitrophenol for detection of bound lymphokine. Recombinant murine IFNγ (Pharmingen) was used as a standard. ELISA spot assays for the detection of antigen-specific, IFNγ-producing cells were performed as described (Taguchi, et al., *J. Immunol.*, 145:68–77, 1990). After a 24 h pre-activation culture of spleen cells with or without antigen, cells were transferred by serial dilution to 96 well microtiter plates (Millipore) that had been precoated with mAb R4-6A2. After 24 h, the cells were removed and IFNγ spots were visualized using XMG 1.2-biotin in conjunction with nitroblue terazolium-bromochloroindolyl phosphate substrate (Sigma). Spots were counted visually and the frequency of antigen specific cells was determined from the difference between the number of spots seen with and without antigen.

As shown in FIG. 9(*a*), when freshly isolated T-cells from 6–9 week old NOD mice were challenged with GAD or control antigens, high concentrations of IFNγ were detected only in cultures containing GAD, suggesting that the GAD specific T-cells had been pre-activated in vivo, since only pre-activated T-cells (Th1) produce IFNγ within 48 hours after antigen recognition (Ehlers, et al., *J. Exp. Med.*, 173:25–36 1991; Croft, et al., *J. Exp. Med.*, 176:1431–1437, 1992). In contrast, T-cells from age matched BALB/c mice did not respond to GAD or to control antigens by IFNγ production (data not shown).

Results of the ELISA spot assay to measure directly the frequency of GAD-specific T-cells showed that while in 6–9 week old NOD mice, T-cells reactive to control antigens constituted approximately 1 in $10^5$ cells in the spleen, the frequency of GAD-reactive T-cells was about two orders of magnitude higher, ranging from 90–291 cells per $10^5$ cells (FIG. 9(*a*), confirming the data obtained by proliferation assays (FIG. 8) that these cells had been clonally expanded in vivo.

In another series of experiments, GAD specific T-cells were characterized for expression of the cell surface marker L-selectin, since murine T-cells convert from an L-selectin$^+$ (L-sel$^+$) to an L-selectin$^-$ (L-sel$^-$) phenotype upon activation (Bradley, et al., *J. immunol.*, 148:324–331, 1992).

To perform these studies, pooled spleen cells from 3 to 4 age matched mice were panned on plates coated with goat-anti-mouse Ig (Zymed) to remove adherent macrophages as well as B cells. Next, CD8+cells were coated with mAb 58.6–72 (ATCC) and removed by panning over plates coated with goat-anti-rat Ig (Zymed). The non-adherent CD4+cell fraction was labeled with anti-L-selectin mAb MEL-14 (ATCC) and panned on goat-anti-rat Ig coated plates. Both the adherent (CD4+L-sel$^+$) and non-adherent (CD4+,L-sel$^-$) fractions were sampled. Purity of the cell fraction was assessed by FACS analysis; cells were >90% CD4+ and >95% enriched for the L-sel$^-$ or L-sel$^+$ phenotype. The purified cell fractions were tested for GAD reactivity by seeding them at 2×$10^5$ cells per well in 96 well microtiter plates with or without antigen. Irradiated (3000 rad), unseparated spleen cells of 3 week old NOD mice were added at 5×$10^5$ cells per well as a source of antigen presenting cells. Supernatants of triplicate cultures were taken 48 h later and their IFNγ content was determined by ELISA.

The results of this study showed that by 2–3 weeks of age, GAD reactive T-cells could not be detected in either the L-sel$^+$ or the L-sel$^-$ population, consistent with a low frequency of antigen reactive precursors at this time point. However, by 6 weeks of age high levels of IFNγ were induced by GAD (but not by control antigens) in the L-sel$^-$ (but not the L-sel$^+$) subpopulation of CD4+ cells (FIG. 9(*b*)).

The increase in clonal size of GAD reactive T-cells, their production of IFNγ and their L-sel$^-$ phenotype provide three independent lines of evidence that a potentially pathogenic (Ando, et al. *Cell Immunol.*, 124:132–143, 1989) Th1 type T-cell response is spontaneously primed to GAD in vivo early in NOD development.

EXAMPLE 8

CHARACTERIZATION OF GAD SPECIFIC T-CELL

DETERMINANT RECOGNITION

The fine specificity of the anti-GAD T-cell response was mapped using a set of 38 peptides (numbered successively from the N-terminus) that were 20–23 amino acids (aa) long and span the entire GAD$_{65}$ (Bu, et al., *Proc. Natl. Acad. Sci.*, 89:2115–2119, 1992) sequence with 5aa overlaps (FIG. 10).

Spleen cells were tested from 4 (FIG. 10*a*), 5 (FIG. 10*b*) and 7 (FIG. 10*c*) week old NOD mice for proliferative responses (as described in Example 4) to the GAD peptides.

Peptides were present in cultures at 7 μM and the label was added during the last 16 hours of a 5-day culture. The peptides were synthesized using standard Fmoc chemistry and purified by reverse phase HPLC (Advanced Chemtech). The sequence of stimulatory peptides are shown below in Table 9.

TABLE 9

| Peptide Number | GAD Region | GAD Region | Amino Acid Sequence |
|---|---|---|---|
| 6 | 78–97 | KPCSCSKVDVNYAFLHATDL | (SEQ ID NO:6) |
| 17 | 247–266 | NMYAMMIARFKMFPEVKEKG | (SEQ ID NO:7) |
| 23 | 335–356 | TAGTTVYGAFDPLLAVADICKK | (SEQ ID NO:8) |
| 32 | 479–498 | EYLYNIIKNREGYEMVFDGK | (SEQ ID NO:9) |
| 34 | 509–528 | IPPSLRTLEDNEERMSRLSK | (SEQ ID NO:10) |
| 35 | 524–543 | SRLSKVAPVIKARMMEYGTT | (SEQ ID NO:11) |
| 36 | 539–558 | EYGTTMVSYQPLGDKVNFFR | (SEQ ID NO:12) |
| 38 | 566–585 | ATHQDIDFLIEEIERLGQDL | (SEQ ID NO:13) |

Murine and human $GAD_{65}$ are 95% identical at the amino acid level (555/585) and are 98% conserved, with most of the differences localized near their N-termini. The underlined amino acid in the stimulatory peptide sequences above are conservatively substituted in murine $GAD_{65}$. In separate experiments, the murine form of key peptides (#17 and #34) were tested and produced similar results.

As shown in FIG. 10, peptides that triggered stimulation indices >3 are indicated as black bars. These peptides did not induce proliferation in T-cells from NOD mice <3 or >16 weeks in age, or from control (BALB/cxNOD)F1 mice (data not shown). The data are represented as the mean SI±standard error calculated from 3–6 individual mice tested twice in each age group. Characteristic results for peptide induced blastogenesis in individual mice are shown in Table 6. The first detectable response, at 4 weeks of age, was confined to the carboxy-terminal region of GAD, and involved two adjacent peptides (aa 509–528 and 524–543, peptides #34 and #35, respectively, FIG. 10*a*). At 5 weeks of age, responses to an additional determinant (aa 247–266, peptide #17, which contains a region of sequence similarity with Coxsackievirus (Kaufman, et al., *J. Clin. Invest.*, 89:283–292, 1992) (FIG. 10*b*) were regularly recorded. During the next two weeks, responses to peptide #17 (aa 247–266) increased and T-cell autoimmunity spread to two additional peptides at the carboxy terminus (aa 479–498 and 539–558; peptides #32 and #36 respectively, FIG. 10*c*). Subsequently, reactivity to the GAD peptides declined (data not shown), paralleling the loss of response to the whole protein (FIG. 8). It is unclear why the initial T-cell response to βCAs fades in NOD mice. Possible explanations include: a) immune regulatory mechanisms; b) exhaustion of the response due to the continuous stimulation by the endogenous antigen; and c) induction of anergy in specific T-cells owing to their recognition of the autoantigen on "non professional" antigen presenting cells such as the β cells themselves (Markmann, et al., *Nature*, 336:476–479, 1988).

The gradual diversification of the primed autoreactive T-cell repertoire that was observed in this naturally occurring autoimmune disease parallels the shifts in T-cell recognition recently observed in experimentally induced autoimmunity to the CNS where autoreactivity spreads both intr- and intermolecularly among CNS proteins (Lehmannn, et al., *Nature*, 358:155–157, 1992; Perry, et al., *J. Neuroimmunol.*, 33:7–15, 1991; Watanabe, et al.,*Nature*, 305:150–153, 1983; Liebert, et al., *J. Neuroimmunol.*, 17:103–118, 1988). Apparently, lymphokine secretion by the first wave of autoantigen specific T-cells in the target organ results in up-regulation of antigen presentation and creates a microenvironment that favors priming of additional autoreactive T-cells (Lehmann, et al., *Immunol Today*, 14:203–208, 1993; Sarvetnick, et al., *Nature*, 346:844–847, 1990; Heath, et al., *Nature*, 359:547–549, 1992). Since hsp reactive CD4+ T-cells are capable of inducing IDDM (Elias, et al., *Proc. Natl. Acad. Sci.*, 87:1576–1580, 1990; Elias, et al., *Proc. Natl. Acad. Sci.*, 88:3088–3091, 1991), their recruitment into the activated T-cell pool, along with T-cells reactive to other βCAs, probably reflects an amplificatory cascade that eventually leads to β cell destruction.

In summary, the data above establish GAD as a critical target antigen in the pathogenesis of IDDM in NOD mice. The results show that T-cell responses to βCAs diversify both intramolecularly and intermolecularly as the disease progresses, consistent with a dynamic autoimmune repertoire (Lehmann, et al., *Immunol.* Today, 14:203–208, 1993). However, interference with the early autoreactive T-cell population can prevent the recruitment of additional autoantigens into the primed repertoire thereby halting a cascade of autoimmune responses that eventually leads to β cell destruction. As a similar autoimmune progression is also likely to occur during the development of human IDDM (Palmer, J. P., Predicting IDDM, *Diabetes Reviews*, 1:14–115, 1993; Atkinson, et al., *Lancet*, 339:458–459, 1992), these findings suggest that peptide-based immunotherapeutic agents would be useful in predicting and ameliorating human IDDM.

EXAMPLE 9

AUTOANTIBODY REACTIVITY WITH GAD FRAGMENTS

This example describes a study which examined the variability in recognition of epitopes in human $GAD_{65}$ polypeptides by IDDM autoantibodies in sera of human patients.

Portions of human $GAD_{65}$ cDNA were amplified by the polymerase chain reaction (PCR; Saiki, et al., *Science*, 239:487, 1988) to produce DNA segments encoding three polypeptide segments: amino acid residues 1–224 (segment A); 224–398 (segment B); and 398–585 (segment C). Each construct also contained a $T_7$ promoter, a consensus sequence for the initiation of translation and an initiating methionine codon (Korak, M., *J. Cell Biol.*, 108:229, 1989). Each PCR product was then trascribed in vitro with $T_7$ RNA polymerase and translated in vitro in a rabbit reticulocyte cell-free system in the presence of $^{35}$S-methionine, using conditions recommended by the supplier (Amersham Corp., Arlington Heights, Ill.). Each test serum (30 μl) was incubated with the resulting $^{35}$S labeled-polypeptides. The bound peptides were isolated with PAS and analyzed by SDS-PAGE in 12% polyaacrylamide and autoradiography.

TABLE 10

IDDM PATIENT SERA REACTIVITY WITH GAD SEGMENTS

| PATIENT | SEGMENT | | |
|---|---|---|---|
| | A | B | C |
| Control (N = 7) | − | − | − |
| 052 | − | + | + |
| 723 | − | − | − |
| 705 | − | + | + |
| UC2 | − | + | + |
| N.L. | − | − | − |
| L.I. | − | − | − |
| T.L. | − | − | − |
| P.T. | − | + | − |
| J.D. | − | − | − |
| B.Y. | − | + | + |
| M.C. | − | − | − |
| R.S. | − | − | − |
| K.O. | − | − | − |
| T.B. | − | − | − |
| S.M. | − | − | − |
| A.W. | − | + | − |
| J.B. | − | + | + |
| J.A. | − | − | − |
| P.C. | − | + | + |
| L.R. | − | − | − |
| J.M. | − | + | − |
| G.A. | − | − | − |

As shown in Table 10, none of the specimens had detectable levels of antibodies to the amino terminal third (segment A) of GAD whereas 9 patients (41%) had antibodies reactive with the middle third (segment B) and 6 patients (27%) had antibodies to the carboxyl-terminal third (segment C) of GAD.

EXAMPLE 10

PREDICTION OF INCIPIENT IDDM BY GAD

EPITOPE RECOGNITION PATTERN

The increasing likelihood of an IDDM interventive therapy and the (recently acknowledged) benefits of managed glucose homeostasis in preventing IDDM associated complications makes the early detection of β cell autoimmunity before clinical IDDM onset and in NIDDM patients (10% of whom eventually convert to IDDM) a crucial goal. Autoanitbodies to GAD may provide the earliest and most reliable marker of impending IDDM among the molecularly defined IDDM associated autoantigens. To determine whether GAD peptides will bind to IDDM associated autoantibodies the following study was conducted.

A set of peptides (20–23 amino acids in length, with 5 aa overlaps) that span the human GAD65 molecule were synthesized to determine whether sera from most individuals at risk, pre-IDDM and with IDDM (in contrast to healthy controls) do in fact produce antibodies that differentially recognize GAD65 linear epitopes distributed throughout the molecule.

Patient sera and most control sera were those used in a previous study (Kaufman, et al., J. Clin. Investigation, supra) All samples were coded and tested in a blind manner. Peptides were synthesized using an automatic instrument (Applied Biosystems, Foster City, Calif.) and standard conditions. Peptides were dissolved in 60 mM sodium bicarbonate buffer (pH 9.6) at 20 ug/ml and 100 ul of each was added to duplicated wells of a 96 well Nunc-Immuno Plate. Peptides were allowed to bind at 4° C. overnight. The plates were then washed three times with PBS+0.1% Tween 20 (wash buffer), after which the plates were pre-absorbed with 3% BSA in sodium bicarbonate buffer for 0.5 hours at 37° C., or at room temperature overnight. The plates were then washed 5 times with the above wash buffer. 100 ul of serum at a 1/300 dilution in PBS+0.1% Tween 20 and 1% BSA was added to each well and antibodies were allowed to bind for 1 hour at 37° C. The plates were washed 5 times with wash buffer. 100 ul of a 1/600 dilution of HRP-goat anti-human IgG (BRL, Gaithersberg, Md.) was added to each well and allowed to bind for 1 hour at 37° C. The plates were then washed 7 times and 100 ul of substrate buffer was added to each well for 30 minutes at room temperature. The color development was measured at 410 nm using an ELISA plate reader (ICN, Biomedicals, Costa Mesa, Calif.). Positive sera were defined as: $OD_{410}$ of the sample/negative control $\geq 3.0$.

The data shown in Table 11 establish that a number of GAD peptides were recognized by patients previously shown to be 64K positive, but not by control sera. Each patient showed a different pattern of GAD epitope recognition. Peptides 20, 21 and 25, were each recognized by 6/8 patients, and none of the controls—with the exception of peptide 25 which was recognized by 1 out of 13 controls. Based on immunoreactivity to 2 of these peptides (#20 and 21) 7/8 (88%) of the patients (and none of the controls) could be identified as possessing GAD autoantibodies. Peptides 3, 6, 22, 25 and 37 were each recognized by only 25–37% of the patients (and none of the control sera),. but taken together, 75% of the patients recognized at least one of these. Peptides 5, 9 and 24 were often positive for immunoreactivity by both control and patient sera.

This level of sensitivity is comparable to the best currently available assays using whole GAD65 purified from brain or recombinant organisms. Besides avoiding laborious antigen purification, peptide based autoantibody screening, together with PCR based HLA typing, may reveal epitope recognition patterns associated with progression or lack of progression to IDDM and its associated complications. Individuals determined to be at high risk could then consider therapeutic intervention.

It should also be noted that the GAD peptides recognized by autoantibodies were different from those recognized by NOD GAD reactive T cells in Example 6.

TABLE 11

EPITOPE RECOGNITION OF HUMAN GAD65 PEPTIDES

| | PEPTIDE | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 |
| Controls | | | | | | | | | | | | | | | | | | | | | | | | | | | | | | | | | | | | | | |
| A.P. | | | | | x | | | | x | | | | | | | | | | | | | | | x | | | | | | | | | | | | | | |
| P.T. | | | | | x | | | | b | | | | | | | | | | | | | | | x | | | | | | | | | | | | | | |
| 5748 | | | | | x | | | | b | | | | | | | | | | | | | | | x | | | | | | | | | | | | | | |
| 5620 | | | | | x | | | | b | | | | | | | | | | | | | | | x | | b | | | | | | | | | | | | |
| 4380 | | | | | x | | | | b | | | | | | | | | | | | | | | x | | | | | | b | | | | | | | | |
| S.M. | | | | | x | | | | x | | | | | | | | | | | | b | | | x | x | | b | | | | | | | | | | | |
| FA8 | | | | | | | | | | | | | | | | | | | | | | | | x | b | | | | | | | | | | | | | |
| FA12 | | | | | b | | | | | | | | | | | | | | | | | | | x | | | | | | | | | | | | | | |
| 1688 | | | | | x | | | | | | | | | | | | | | | | | | | x | | | | | | | | | | | | | | |
| FA9 | | | | | b | | | | | | | | | | | | | | | | | | | x | | | | | | | | | | | | | | |
| H.B | | | | | x | | | | | | | | | | | | | | | | | | | x | | | | | | | | | | | | | | |
| FA2 | | | | | x | | | | | | | | | | | | | | | | | | | x | | | | | | | | | | | | | | |
| FA11 | | | | | | | | | | | | | | | | | | | | | | | | | 1 | | | | | | | | | | | | | |
| IDDM At Risk | | | | | | | | | | | | | | | | | | | | | | | | | | | | | | | | | | | | | | |
| 052 | | b | | | | | | | | | | | | b | b | b | | | x | x | | | | x | b | | | b | x | | b | | | | | | | |
| 825 | | | | | | | | | | | x | | | | | | | | | | x | | | x | x | | | | | | | | | | | | | |
| 356 | | | | | | | | | | | | | | | | | | | | b | | | | x | | | | | | | | | | | | | | |
| L.I. | | | b | | | | | x | | | b | | | | | | | | | | | | | | | | | | | | | b | | | | | | b |

TABLE 11-continued

EPITOPE RECOGNITION OF HUMAN GAD65 PEPTIDES

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|---|---|---|---|---|---|---|---|---|---|---|---|---|---|---|---|---|---|---|
| Pre-IDDM | | | | | | | | | | | | | | | | | | | | | | | | | | | | | | | | | | | | | | |
| J.A. | | | | | | | | | | | | | | | | | | | | | | | | | | | | | | | | | | | | | | |
| 723 | | | x | | x | | | | | | | | | | | | | | | | x | | | x | x | | | | | | | | | | | | | |
| P.T. (1) | | | x | x | x | | | | x | | | | | | | | | | | x | x | | | x | b | | | | x | | | b | b | | | | | |
| P.T. (2) | | | b | | x | b | b | b | b | | | | | | | | | | | x | b | | | x | x | | | | x | | | b | b | b | | | | |
| J.B. (1) | | | b | | x | | b | b | | | b | | | | | | | | | | | | | x | | | | | | | | | | | | | | |
| J.B. (2) | | | x | | x | | b | b | b | | b | | | | | | | | | b | b | | | x | b | | | | b | | | | | | | | | |
| R.S. (1) | | | x | | x | b | b | b | b | | b | | | | | | | | | b | | | | x | x | | | | | | | | | | | | | |
| R.S. (2) | | | | | x | | | | | | x | | | | | | | | | | | | | x | x | | | | | | | | | | | | | |
| B.Y. (1) | | | | | x | | | b | | | b | | | | | | | | | | | | | x | | | | | | | | | | | | | | |
| B.Y. (2) | | | | | b | | | | | | b | | | | | | | | | b | b | | | x | b | | | b | | | | | | | | | | |
| J.B. (1) | b | x | x | | | | | | | | | | | | | | | | | | | | | | | | | | | | | | | | | | | |
| J.B. (2) | | | b | x | x | | b | | | | | | | | | | | | | | | | | | | | x | | | | | | | | | | | |
| At Onset | | | | | | | | | | | | | | | | | | | | | | | | | | | | | | | | | | | | | | |
| 705 | | | x | | x | x | | | x | | | | | | | | | | | x | x | x | x | x | x | | | | x | | | | | | | x | x | b |
| S.H. | | | b | x | x | | | | | | | | | | | | | | | x | x | x | x | x | x | | | | | | | | | | | | | |
| 291 | | | x | | x | | b | | | | | | | | | | | | | x | x | | x | x | x | | x | | | | | b | x | b | | | | x |
| 048 | | | x | | x | | | | x | | | | | | | | | | | x | x | | x | x | x | | | | x | | | x | x | x | | | | |
| | | | 5 | 1 | | 2 | 2 | 2 | 3 | | 2 | | | | | | | | 1 | 7 | 7 | 2 | | | 8 | | 1 | | 4 | | | 1 | 1 | 1 | 1 | 1 | 2 | 1 | x = positive for immunoreactivity as defined by OD/background ≥ 3.0
b = borderline response (OD/background 2.5–2.9).

EXAMPLE 11

GAD IMMUNIZATION PROTECTS NOD MICE FROM IDDM

The availability of cDNAs encoding GAD65 allows the testing of this molecule in new interventive therapies designed to interfere with GAD-specific T cells. Tests were conducted to examine the ability of GAD65 immunization to protect NOD mice at 8 weeks of age, a time at which T cell responses to a number of b cell antigens and insulifis is already well established. If GAD immunotherapy was effective at this stage, it would hold promise for treatment in humans in which the autoimmune process has already been established.

METHODS

Antigens

An IPTG inducible T7 expression vector was used to express both human GAD65 and E. coli b galactosidase (β-gal). In IPTG induced recombinant E. coli, GAD and β-gal constitute about 10–20% of the total bacterial protein. However, almost all of the GAD was in inclusion bodies, which could be isolated and extensively washed to obtain material that is about 80% GAD. We then did affinity purifications of GAD and β-gal on the basis of a hexa-histidine "tag" which was attached to GAD during the subcloning process. These extra histidine residues allow the rapid affinity purification (Novagen) of GAD by metal affinity chromatography (Hochuli, et al., Bio Technology, 6:1321–1325, 1988). The inclusion body material is solubilized in 6M guanidine hydrochloride (GHCL), 10 mm β-mercaptoethanol and 1% triton X-100. After binding to the column, the column was extensively washed with GHCL and 8M urea in phosphate buffers. Only the central peak GAD fraction was utilized for subsequent studies. Human GAD65 shares 96% amino acid sequence identity with murine GAD65, with most of the amino acid differences being conservative substitutions.

The GAD preparation appeared to be free of immunologically detectable contaminants. It also appeared to be free of bacterial contaminants on overloaded silver stained gels. Analysis by a national reference laboratory found <0.06 ng LPS/ug GAD. Human GAD65 did not induce T cell proliferation in <4 or >16 week old NOD or control BALB/c or (NOD/BALB/c) F1 spleen cells. The results using synthetic GAD peptides (FIG. 10) precisely parallel the data using whole recombinant GAD (FIG. 8). Other antigens described herein elsewhere that are not involved in IDDM (such as the beta galactosidase) did not induce NOD T cell responses. After immunizing mice with GAD, we were unable to detect cross reactive T cell responses in recall experiments with other proteins that were purified from recombinant E. coli by the same metal affinity chromatography procedure. Amino acid sequence analysis of GAD and β-gal each gave a single expected amino acid N-terminal sequence. If there had been appreciable endotoxins, heat shock proteins, or other contaminants present in the GAD preparation, spleen, PBMC (Atkinson, et al.), and T cell proliferation responses that were not disease specific would have been expected.

Breeder mice were purchased from Taconic Farms and housed under specific pathogen-free conditions. Only female NOD mice were used in this study. The average age of IDDM onset in unrelated females in the colony was 22 weeks. Insulitis is generally observed beginning at 4 weeks of age. T cell responses to GAD, HSP, CPH were found by 6 weeks in age. The incidence of IDDM in female mice is 70–90% by one year of age.

Immunizations

At 8 weeks of age, 25 ug GAD or control β-gal. was injected intraperftoneally (ip) in 100 ul of incomplete Freunds adjuvant (IFA). Because there may be a requirement for continual antigen presentation (Ramsdell, et al., Science, 257:1130–1133, 1992) mice were treated again every 6 weeks. Urine glucose levels were monitored twice weekly. After observing above normal glucose in urea, blood glucose levels were monitored twice weekly. Two consecutive blood glucose level readings of 300 mg/ml was considered as IDDM onset, after which the mice were sacrificed and spleen cells were tested as described above in Example 6 for evidence of spleen cell proliferation.

Immunization of 8 week old NOD mice produced a clear delay in the onset of IDDM compared to control β-gal immunized mice (FIG. 11). While two of the GAD immunized mice (open circles) developed IDDM at about the normal age of onset (20 weeks), the other 8 GAD immunized mice showed no signs of hyperglycemia until 36 weeks in age. Four of the GAD treated mice developed IDDM between 37 and 40 weeks in age. Four of the GAD treated mice currently remain disease free (at 52 weeks of age). In contrast, the majority of β-gal injected mice (closed circles) had hyperglycemia by 22 weeks of age and 6/10 developed IDDM by 27 weeks in age. At 52 weeks of age, 2 of the β-gal treated mice remain disease free. This experiment shows that GAD immunization significantly delayed (<0.02) or prevented diabetes of NOD mice in which β cell autoimmunity has already significantly progressed.

β cell autoimmunity is already well established at 8 weeks of age, and it is likely to also be in individuals determined to be at risk for IDDM on the basis of circulating autoantibodies. Although the mechanism of this protection is not clear, periodic injections of GAD have a profound moderating effect on the induction of disease.

TABLE 12

AMINO ACID (SEQUENCES FOR GAD65

| | | |
|---|---|---|
| 1 | (SEQ ID NO:14) | MASPGSGFWSFGSEDGSGDS |
| 2 | (SEQ ID NO:15) | GSGDSENPGTARAWCQVAQKFTG |
| 3 | (SEQ ID NO:16) | QKFTGGIGNKLCALLYGD |
| 4 | (SEQ ID NO:17) | LLYGDAEKPAESGGSQPPRA |
| 5 | (SEQ ID NO:18) | QKFTGGIGIGNKLCALLYGD |
| 6 | (SEQ ID NO:19) | KPCSCSKVDVNYAFLHATDL |
| 7 | (SEQ ID NO:20) | HATDLLPACDGERPTLAFLQ |
| 8 | (SEQ ID NO:21) | LAFLQDVMNILLQYVVKSFDRS |
| 9 | (SEQ ID NO:22) | SFDRSTKVIDFHYPNELLQE |
| 10 | (SEQ ID NO:23) | ELLQEYNWELADQPQNLEEILM |
| 11 | (SEQ ID NO:24) | EEILMHCQTTLKYAIKTGHP |
| 12 | (SEQ ID NO:25) | KYGHPRYFNQLSTGLDMVGL |
| 13 | (SEQ ID NO:26) | DMVGLAADWLTSTANTNMFT |
| 14 | (SEQ ID NO:27) | TNMFTYEIAPVFVLLEYVTL |
| 15 | (SEQ ID NO:28) | EYVTLKKMREIIGWPGGSGD |
| 16 | (SEQ ID NO:29) | GGSGDGIFSPGGAISNMYAM |
| 17 | (SEQ ID NO:30) | NMYAMMIARFKMFPEVKEKG |
| 18 | (SEQ ID NO:31) | PEVKEKGMAALPRLIAFTSE |
| 19 | (SEQ ID NO:32) | AFTSEHSHFSLKKGAAALGI |
| 20 | (SEQ ID NO:33) | AALGIGTDSVILIKCDERGK |
| 21 | (SEQ ID NO:34) | DERGKMIPSDLERRILEAKQ |
| 22 | (SEQ ID NO:35) | LEAKQKGFVPFLVSATAGTT |
| 23 | (SEQ ID NO:36) | TAGTTVYGAFDPLLAVADICKK |
| 24 | (SEQ ID NO:37) | DICKKYKIWMHVDAAQGGGLLMS |
| 25 | (SEQ ID NO:38) | GLLMSRKHKWKLSGVERANS |
| 26 | (SEQ ID NO:39) | ERANSVTWNPHKMMGVPLQC |
| 27 | (SEQ ID NO:40) | VPLQCSALLVREEGLMQNCNQ |
| 28 | (SEQ ID NO:41) | QNCNQMHASYLFQQDKHYDL |
| 29 | (SEQ ID NO:42) | KHYDLSYDTGDKALQCGRHV |
| 30 | (SEQ ID NO:43) | CGRHVDVFKLWLMWRAKGTTG |
| 31 | (SEQ ID NO:44) | KGTTGFEAHVDKCLELAEYLYN |
| 32 | (SEQ ID NO:45) | EYLYNIIKNREGYEMVFDGK |
| 33 | (SEQ ID NO:46) | VFDGKPQHTNVCFWYIPPSL |

TABLE 12-continued

AMINO ACID (SEQUENCES FOR GAD65

```
34 (SEQ ID NO:47) IPPSLRTLEDNEERMSRLSK
35 (SEQ ID NO:48) SRLSKVAPVIKARMMEYGTT
36 (SEQ ID NO:49) EYGTTMVSYQPLGDKVNFFR
37 (SEQ ID NO:50) VNFFRMVISNPAATHQDIDF
38 (SEQ ID NO:51) ATHQDIDFLIEEIERLGQDL
```

The invention now being fully described, it will be apparent to one of ordinary skill in the art that many changes and modifications can be made without departing from the scope of the invention.

We claim:

1. A method for ameliorating a GAD-associated autoimmune disorder in a patient having the disorder, said method comprising administering to the patient a GAD$_{65}$ peptide consisting of the amino acid sequence selected from the group consisting of:
KPCSCSKVDVNYAFLHATDL (SEQ ID NO:06);
NMYAMMIARFKMFPEVKEKG (SEQ ID NO:07);
TAGTTVYGAFDPLLAVADICKK (SEQ ID NO:08);
EYLYNIIKNREGYEMVFDGK (SEQ ID NO:09);
IPPSLRYLEDNEERMSRLSK (SEQ ID NO:10);
SRLSKVAPVIKARMMEYGTT (SEQ ID NO:11);
EYGTTMVSYQPLGDKVNFFR (SEQ ID NO:12);
ATHQDIDFLIEEIERLGQDL (SEQ ID NO:13);
QKFTGGIGNKLCALLYGD (SEQ ID NO:60);
LLYGDAEKPAESGGSQPPRA (SEQ ID NO:17);
KPCSCSKVDVNYAFLHATDL (SEQ ID NO:06);
LAFLQDVMNILLQYVVKSFDRS (SEQ ID NO:21);
EEILMHCQTTLKYAIKTGHP (SEQ ID NO:24);
AFTSEHSHFSLKKGAAALGI (SEQ ID NO:32);
AALGIGTDSVILIKCDERGK (SEQ ID NO:33);
DERGKMIPSDLERRILEAKQ (SEQ ID NO:34);
LEAKQKGFVPFLVSATAGTT (SEQ ID NO:35);
GLLMSRKHKWKLSGVERANS (SEQ ID NO:38);
VPLQCSALLVREEGLMQNCNQ (SEQ ID NO:40);
KHYDLSYDTGDKALQCGRHV (SEQ ID NO:42);
IPPSLRTLEDNEERMSRLSK (SEQ ID NO:47);
VNFFRMVISNPAATHQDIDF (SEQ ID NO:50);
amino acids 224–398 of SEQ ID NO:57; and
amino acids 398–585 of SEQ ID NO:57.

2. The method according to claim 1, wherein said peptide consists of the amino acid sequence KPCSCSKVDVNYAFLHATDL (SEQ ID NO:06).

3. The method according to claim 1, wherein said peptide consists of the amino acid sequence NMYAMMIARFKMFPEVKEKG (SEQ ID NO:07).

4. The method according to claim 1, wherein said peptide consists of the amino acid sequence TAGTTVYGAFDPLLAVADICKK (SEQ ID NO:08).

5. The method according to claim 1, wherein said peptide consists of the amino acid sequence EYLYNIIKNREGYEMVFDGK (SEQ ID NO:09).

6. The method according to claim 1, wherein said peptide consists of the amino acid sequence IPPSLRYLEDNEERMSRLSK (SEQ ID NO:10).

7. The method according to claim 1, wherein said peptide consists of the amino acid sequence SRLSKVAPVIKARMMEYGTT (SEQ ID NO:11).

8. The method according to claim 1, wherein said peptide consists of the amino acid sequence EYGTTMVSYQPLGDKVNFFR (SEQ ID NO:12).

9. The method according to claim 1, wherein said peptide consists of the amino acid sequence ATHQDIDFLIEEIERLGQDL (SEQ ID NO:13).

10. The method according to claim 1, wherein said peptide consists of the amino acid sequence QKFTGGIGNKLCALLYGD (SEQ ID NO:60).

11. The method according to claim 1, wherein said peptide consists of the amino acid sequence LLYGDAEKPAESGGSQPPRA (SEQ ID NO:17).

12. The method according to claim 1, wherein said peptide consists of the amino acid sequence KPCSCSKVDVNYAFLHATDL (SEQ ID NO:06).

13. The method according to claim 1, wherein said peptide consists of the amino acid sequence LAFLQDVMNILLQYVVKSFDRS (SEQ ID NO:21).

14. The method according to claim 1, wherein said peptide consists of the amino acid sequence EEILMHCQTTLKYAIKTGHP (SEQ ID NO:24).

15. The method according to claim 1, wherein said peptide consists of the amino acid sequence AFTSEHSHFSLKKGAAALGI (SEQ ID NO:32).

16. The method according to claim 1, wherein said peptide consists of the amino acid sequence AALGIGTDSVILIKCDERGK (SEQ ID NO:33).

17. The method according to claim 1, wherein said peptide consists of the amino acid sequence DERGKMIPSDLERRILEAKQ (SEQ ID NO:34).

18. The method according to claim 1, wherein said peptide consists of the amino acid sequence LEAKQKGFVPFLVSATAGTT (SEQ ID NO:35).

19. The method according to claim 1, wherein said peptide consists of the amino acid sequence GLLMSRKHKWKLSGVERANS (SEQ ID NO:38).

20. The method according to claim 1, wherein said peptide consists of the amino acid sequence VPLQCSALLVREEGLMQNCNQ (SEQ ID NO:40).

21. The method according to claim 1, wherein said peptide consists of the amino acid sequence KHYDLSYDTGDKALQCGRHV (SEQ ID NO:42).

22. The method according to claim 1, wherein said peptide consists of the amino acid sequence IPPSLRTLEDNEERMSRLSK (SEQ ID NO:47).

23. The method according to claim 1, wherein said peptide consists of the amino acid sequence VNFFRMVISNPAATHQDIDF (SEQ ID NO:50).

24. The method according to claim 1, wherein said peptide consists of amino acids 224–398 of SEQ ID NO:57.

25. The method according to claim 1, wherein said peptide consists of amino acids 398–585 of SEQ ID NO:57.

26. A method for ameliorating a GAD-associated autoimmune disorder in a patient having the disorder, which comprises administering to the patient a $GAD_{65}$ peptide which binds to an HLA or autoantibody related to said GAD-associated autoimmune disorder, wherein said peptide is from 5 to 12 amino acids in length consecutively contained within an amino acid sequence selected from the group consisting of:

KPCSCSKVDVNYAFLHATDL (SEQ ID NO:06);
NMYAMMIARFKMFPEVKEKG (SEQ ID NO:07);
TAGTTVYGAFDPLLAVADICKK (SEQ ID NO:08);
EYLYNIIKNREGYEMVFDGK (SEQ ID NO:09);
IPPSLRYLEDNEERMSRLSK (SEQ ID NO:10);
SRLSKVAPVIKARMMEYGTT (SEQ ID NO:11);
EYGTTMVSYQPLGDKVNFFR (SEQ ID NO:12);
ATHQDIDFLIEEIERLGQDL (SEQ ID NO:13);
QKFTGGIGNKLCALLYGD (SEQ ID NO:60);
LLYGDAEKPAESGGSQPPRA (SEQ ID NO:17);
KPCSCSKVDVNYAFLHATDL (SEQ ID NO:06);
LAFLQDVMNILLQYVVKSFDRS (SEQ ID NO:21);
EEILMHCQTTLKYAIKTGHP (SEQ ID NO:24);
AFTSEHSHFSLKKGAAALGI (SEQ ID NO:32);
AALGIGTDSVILIKCDERGK (SEQ ID NO:33);
DERGKMIPSDLERRILEAKQ (SEQ ID NO:34);
LEAKQKGFVPFLVSATAGTT (SEQ ID NO:35);
GLLMSRKHKWKLSGVERANS (SEQ ID NO:38);
VPLQCSALLVREEGLMQNCNQ (SEQ ID NO:40);
KHYDLSYDTGDKALQCGRHV (SEQ ID NO:42);
IPPSLRTLEDNEERMSRLSK (SEQ ID NO:47);
VNFFRMVISNPAATHQDIDF (SEQ ID NO:50);
amino acids 224–398 of SEQ ID NO:57; and
amino acids 398–585 of SEQ ID NO:57.

27. A method for ameliorating a GAD-associated autoimmune disorder in a patient having the disorder, which comprises administering to the patient a $GAD_{65}$ peptide of from 5 to 1 2 amino acids in length consecutively contained within an amino acid sequence selected from the group consisting of:

KPCSCSKVDVNYAFLHATDL (SEQ ID NO:06);
NMYAMMIARFKMFPEVKEKG (SEQ ID NO:07);
TAGTTVYGAFDPLLAVADICKK (SEQ ID NO:08);
EYLYNIIKNREGYEMVFDGK (SEQ ID NO:09);
IPPSLRYLEDNEERMSRLSK (SEQ ID NO:10);
SRLSKVAPVIKARMMEYGTT (SEQ ID NO:11);
EYGTTMVSYQPLGDKVNFFR (SEQ ID NO:12);
ATHQDIDFLIEEIERLGQDL (SEQ ID NO:13);
QKFTGGIGNKLCALLYGD (SEQ ID NO:60);
LLYGDAEKPAESGGSQPPRA (SEQ ID NO:17);
KPCSCSKVDVNYAFLHATDL (SEQ ID NO:06);
LAFLQDVMNILLQYVVKSFDRS (SEQ ID NO:21);
EEILMHCQTTLKYAIKTGHP (SEQ ID NO:24);
AFTSEHSHFSLKKGAAALGI (SEQ ID NO:32);
AALGIGTDSVILIKCDERGK (SEQ ID NO:33);
DERGKMIPSDLERRILEAKQ (SEQ ID NO:34);
LEAKQKGFVPFLVSATAGTT (SEQ ID NO:35);
GLLMSRKHKWKLSGVERANS (SEQ ID NO:38);
VPLQCSALLVREEGLMQNCNQ (SEQ ID NO:40);
KHYDLSYDTGDKALQCGRHV (SEQ ID NO:42);
IPPSLRTLEDNEERMSRLSK (SEQ ID NO:47);
VNFFRMVISNPAATHQDIDF (SEQ ID NO:50);
amino acids 224–398 of SEQ ID NO:57; and
amino acids 398–585 of SEQ ID NO:57.

28. The method according to claim 1, 26 or 27, wherein the disorder is IDDM.

29. The method according to claim 1, 26 or 27, wherein the disorder is stiff man disease.

30. The method according to claim 1, 26 or 27, wherein the administration is enteral.

31. The method according to claim 1, 26 or 27, wherein the administration is oral.

32. The method according to claim 1, 26 or 27, wherein the administration is parenteral.

33. The method according to claim 1, 26 or 27, wherein the administration is by subcutaneous, intramuscular, intraperitoneal, intracavity, transdermal, intranasal, or intravenous injection.

34. The method according to claim 1, 26 or 27, wherein said administration is at a dosage of about 0.01 mg/kg/dose to about 2000 mg/kg/dose.

35. The method according to claim 1, 26 or 27, wherein the peptide is therapeutically labeled.

36. The method according to claim 35, wherein the therapeutic label is selected from the group consisting of a radioisotope, a drug, a lectin, and a toxin.

* * * * *